(12) United States Patent
Sheng et al.

(10) Patent No.: US 12,350,333 B2
(45) Date of Patent: *Jul. 8, 2025

(54) CHECKPOINT REGULATOR ANTAGONISTS

(71) Applicant: Gensun Biopharma Inc., Newbury Park, CA (US)

(72) Inventors: Jackie Z. Sheng, Thousand Oaks, CA (US); Bo Liu, Thousand Oaks, CA (US)

(73) Assignee: Gensun Biopharma Inc., Newbury Park, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 18/053,878

(22) Filed: Nov. 9, 2022

(65) Prior Publication Data

US 2023/0293684 A1    Sep. 21, 2023

Related U.S. Application Data

(63) Continuation of application No. 16/696,253, filed on Nov. 26, 2019, now Pat. No. 11,517,623, which is a continuation of application No. 15/858,963, filed on Dec. 29, 2017, now Pat. No. 10,537,637.

(60) Provisional application No. 62/442,642, filed on Jan. 5, 2017.

(51) Int. Cl.
| | | |
|---|---|---|
| *A61K 39/395* | (2006.01) | |
| *A61K 38/17* | (2006.01) | |
| *A61K 39/00* | (2006.01) | |
| *A61P 35/00* | (2006.01) | |
| *C07K 16/28* | (2006.01) | |

(52) U.S. Cl.
CPC .... *A61K 39/39558* (2013.01); *A61K 38/1774* (2013.01); *A61K 39/0011* (2013.01); *A61P 35/00* (2018.01); *C07K 16/2803* (2013.01); *C07K 16/2818* (2013.01); *A61K 2039/507* (2013.01); *C07K 2317/31* (2013.01); *C07K 2317/33* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,837,243 A | 11/1998 | Deot et al. |
| 5,869,046 A | 2/1999 | Presta et al. |
| 5,922,845 A | 7/1999 | Deo et al. |
| 6,054,297 A | 4/2000 | Carter et al. |
| 6,111,090 A | 8/2000 | Gorman et al. |
| 6,121,022 A | 9/2000 | Presta et al. |
| 6,365,157 B2 | 4/2002 | Rockwell et al. |
| 6,376,653 B1 | 4/2002 | Holmes et al. |
| 6,448,077 B1 | 9/2002 | Rockwell et al. |
| 6,582,959 B2 | 3/2003 | Kitano et al. |
| 6,703,020 B1 | 3/2004 | Thorpe et al. |
| 6,884,879 B1 | 4/2005 | Baca et al. |
| 7,025,962 B1 | 4/2006 | Gorman et al. |
| 7,060,269 B1 | 6/2006 | Baca et al. |
| 7,067,637 B1 | 6/2006 | Hotten et al. |
| 7,138,370 B2 | 11/2006 | Oliner et al. |
| 7,169,901 B2 | 1/2007 | Baca et al. |
| 7,182,135 B2 | 2/2007 | Szarka |
| 7,227,004 B2 | 6/2007 | Kim |
| 7,297,334 B2 | 11/2007 | Baca et al. |
| 7,338,660 B2 | 3/2008 | Bedian et al. |
| 7,365,166 B2 | 4/2008 | Baca et al. |
| 7,494,651 B2 | 2/2009 | Jones et al. |
| 7,498,414 B2 | 3/2009 | Zhu |
| 7,521,053 B2 | 4/2009 | Oliner |
| 7,527,791 B2 | 5/2009 | Adams et al. |
| 7,575,893 B2 | 8/2009 | Simmons |
| 7,579,186 B1 | 8/2009 | Sakamoto et al. |
| 7,618,632 B2 | 11/2009 | Collins et al. |
| 7,619,069 B2 | 11/2009 | Davies et al. |
| 7,658,924 B2 | 2/2010 | Oliner et al. |
| 7,691,977 B2 | 4/2010 | Fuh et al. |
| 7,758,859 B2 | 7/2010 | Fuh et al. |
| 7,811,785 B2 | 10/2010 | Fuh et al. |
| 7,812,135 B2 | 10/2010 | Smith et al. |
| 8,030,025 B2 | 10/2011 | Boone et al. |
| 8,367,805 B2 | 2/2013 | Chamberlain et al. |
| 8,388,967 B2 | 3/2013 | Smith et al. |
| 8,389,692 B2 | 3/2013 | Takayama et al. |

(Continued)

FOREIGN PATENT DOCUMENTS

| | | |
|---|---|---|
| EP | 0090505 | 8/1990 |
| EP | 1866339 | 5/2013 |

(Continued)

OTHER PUBLICATIONS

Johnston R.J. et al., "The immunoreceptor TIGIT Regulates antitumor and antiviral CD8(+) T Cell effector Functions" Dec. 8, 2014, Cancer Cell, vol. 26(6), pp. 923-937.
Joller, N, et al. "Treg Cells Expressing The Coinhibitory Molecule TIGIT Selectively Inhibits Pro inflammatory Th1 and Th17 Cell Response," Immunity, Apr. 17, 2014 vol. 40(4), pp. 569-581.
Ridge, J.P, et al. "A Conditioned Dendritic Cell Can Be a Temporal Bridge Between a CD4+ T-Helper and a T-Killer Cell" Natur, Jun. 4, 1998, 393:474-478.
Communication pursuant to Rule 164(1) EPC, issued in European Application No. 17890428.0, mail date Oct. 19, 2020.
International Search Report and the Written Opinion of the International Searching Authority issued in International Application No. PCT/USI 9/39994, dated Nov. 21, 2019.
International Search Report and the Written Opinion of the International Searching Authority issued in International Application No. PCT/US19/39982, dated Dec. 3, 2019.

(Continued)

*Primary Examiner* — Laura B Goddard
(74) *Attorney, Agent, or Firm* — Michael Ye; Kalos Athena Wang PLLC

(57) ABSTRACT

Checkpoint regulator antagonists that bind specifically to TIGIT, PD-1 and/or PD-L1 are disclosed. Also disclosed are methods of making and using the checkpoint regulator inhibitors, including monospecific, bispecific and trispecific checkpoint regulator antagonists thereof.

16 Claims, 47 Drawing Sheets

Specification includes a Sequence Listing.

(56) References Cited

U.S. PATENT DOCUMENTS

| | | | |
|---|---|---|---|
| 8,475,798 | B2 | 7/2013 | Patti et al. |
| 8,574,577 | B2 | 11/2013 | Barbas, III |
| 8,586,023 | B2 | 11/2013 | Shiku et al. |
| 8,591,886 | B2 | 11/2013 | Ponath et al. |
| 8,992,913 | B2 | 3/2015 | Mader et al. |
| 9,079,965 | B2 | 7/2015 | Zhou et al. |
| 9,200,079 | B2 | 12/2015 | Chamberlain et al. |
| 9,676,863 | B2 | 6/2017 | Lo |
| 9,764,038 | B2 | 9/2017 | Dennler et al. |
| 9,890,204 | B2 | 2/2018 | Brinkmann et al. |
| 9,987,500 | B2 | 6/2018 | Papadopoulos et al. |
| 9,994,632 | B2 | 6/2018 | Kim et al. |
| 10,112,997 | B2 | 10/2018 | Gurney et al. |
| 10,189,902 | B2 | 1/2019 | Maurer et al. |
| 2003/0190317 | A1 | 10/2003 | Baca et al. |
| 2003/0203409 | A1 | 10/2003 | Kim |
| 2003/0206899 | A1 | 11/2003 | Ferrara et al. |
| 2005/0186208 | A1 | 8/2005 | Fyfe et al. |
| 2006/0009360 | A1 | 1/2006 | Pifer et al. |
| 2006/0093600 | A1 | 5/2006 | Bedian et al. |
| 2006/0099150 | A1 | 5/2006 | Houston et al. |
| 2006/0173170 | A1 | 8/2006 | Chamberlain et al. |
| 2006/0280747 | A1 | 12/2006 | Fuh et al. |
| 2007/0020267 | A1 | 1/2007 | Fuh et al. |
| 2007/0059312 | A1 | 3/2007 | Baca et al. |
| 2007/0141065 | A1 | 6/2007 | Fuh et al. |
| 2010/0183623 | A1 | 7/2010 | Palti et al. |
| 2013/0022601 | A1 | 1/2013 | Brinkmann et al. |
| 2013/0078248 | A1 | 3/2013 | Gschwind et al. |
| 2013/0259859 | A1 | 10/2013 | Ott et al. |
| 2013/0336982 | A1 | 12/2013 | Mader et al. |
| 2014/0243505 | A1 | 8/2014 | Zhou et al. |
| 2014/0308285 | A1 | 10/2014 | Yan et al. |
| 2014/0356385 | A1 | 12/2014 | Dennler et al. |
| 2015/0197578 | A1 | 7/2015 | Thurston et al. |
| 2015/0337033 | A1 | 11/2015 | Kim et al. |
| 2016/0176963 | A1 | 6/2016 | Maurer et al. |
| 2016/0305947 | A1* | 10/2016 | Pierce ............... C07K 16/2818 |
| 2016/0355589 | A1 | 12/2016 | Williams et al. |
| 2017/0044256 | A1 | 2/2017 | Grogan et al. |
| 2017/0275353 | A1 | 9/2017 | Sheng et al. |
| 2018/0185482 | A1 | 7/2018 | Sheng et al. |

FOREIGN PATENT DOCUMENTS

| | | |
|---|---|---|
| EP | 1947183 | 7/2013 |
| WO | 9920758 | 4/1999 |
| WO | 9940196 | 8/1999 |
| WO | 200103720 | 1/2001 |
| WO | 2005007190 | 1/2005 |
| WO | 2005055808 | 6/2005 |
| WO | 2006083289 | 8/2006 |
| WO | 2007133822 | 11/2007 |
| WO | 2010003118 | 1/2010 |
| WO | 2011028683 | 3/2011 |
| WO | 2005115451 | 5/2011 |
| WO | 2011051726 | 5/2011 |
| WO | 2011090754 | 7/2011 |
| WO | 2013039954 | 3/2013 |
| WO | 2014062659 | 4/2014 |
| WO | 2016187594 | 11/2016 |
| WO | 2016/191643 | 12/2016 |
| WO | 2017218707 | 6/2017 |
| WO | 2017161976 | 9/2017 |
| WS | 20181283939 | 7/2018 |

OTHER PUBLICATIONS

International Search Report and the Written Opinion of the International Searching Authority issued in International Application No. PCT/US19/39979, dated Nov. 12, 2019.

Hinton, et al., "Engineered Human IgG Antibodies with Longer Serum Half-lives in Primates", Journal of Biological Chemistry, 2004, 279(8): 6213-6216.

2 Hinton, et al.* "An Engineered Human IgG1 Antibody with Longer Serum Half-Life", Journal of Immunology, 2006, 176:346-356.

Shields, et al., "High Resolution Mapping of the Binding Site on Human IgG1 for FcyRI, FcyRII, FcyRIII, and FcRn and Design of IgG1 Variants with Improved Binding to the FcyR", Journal of Biological Chemistry, 2001, 276.

Dalliacquai et al., "Increasing the Affinity of a Human IgG1 for the Neonatal FC Receptor: Biological Consequences", The Journal of Immunology, 2002, 169:5171-5180.

Dall'Acqua, et al., Properties of Human IgG1s Engineered for Enhanced Binding to the Neonatal FC Receptor Journal of Biological Chemistry, 2006, 28123514-23524.

Yeung, et al., "Engineering Human IgG1 Affinity to Human Neonatal FC Receptor: Impact of Affinity Improvement of Pharmacokinetics in Primates", The Journal of Immunology, 2009, 182:7663.

Wranik, et al., "LUZ-Y, a Novel Platform for the Mammalian Cell Production of Full-length IgG-bispecific Antibodies", Journal of Biological Chemistry, 2012.

He, Y. et al., Blocking Programmed Death-I Ligand-PD-1 Interactions by Local Gene Therapy Results in Enhancement of Antitumor Effect of Secondary Lymphoid Tissue Chemokinet, The Journal of Immunology, 20041 173:4919-4928.

Rosenberg, S.A. et al., "A New Era for Cancer Immunotherapy Based on the Genes that Encode Cancer Antigens", Immunity, Mar. 1999, vol. 10, pp. 281-287.

Kim, N.W., et al., "Specific Association of Human Telomerase Activity with Immortal Cells and Cancer", Dec. 1994, vol. 266, pp. 2011-2013.

Karyampudi, L. et al., "Accumulation of memory precursor CD8 T cells in regressing tumors following combination therapy with vaccine and anti-PD-I antibody", Jun. 2014, 74:2974-2985.

Mokyr, M.B. et al., "Relization of the Therapeutic Potential of CT LA-4 Blockage in Low-Dose Chemotherpahy-treated Tumor-bearing Mice", Cancer Research (1998), 58:5301-5304.

Ridge, J.P. et al., "A conditioned dendritic cell can be a temporal bridge between a CD4+ T-helper and a T-killer cell", Nature, Jun. 4, 1998, 393:474-478.

Weinberg, A.D. et al., "Engagement of the OX-40 receptor in vivo enhances antitumor immunity", Journal of Immunology, Feb. 15, 2000.

Thompson, R.H. et al., "Tumor B7-H1 Is Associated with Poor Prognosis in Renal Cell Carcinoma Patients with Long-term Follow-up", (2006).

Ahmadzadeh, M. et al "Tumor antigen-specific CD8 T cells infiltrating the tumor express high levels of PD-I and are functionally impaired", Blood, Aug. 20, 2009.

Greenberg, P.D. et al., "Deficient Cellular Immunit-Finding and Fixing the Defects", Science Jul. 23, 1999, 23:285 (546-551).

Melero, I et al., "Monoclonal antibodies against the 4-1 BB T-cell activation molecule eradicate established tumors", Nature Medicine, Jun. 1997.

Hutloff, A et al., "ICOS is an inducible T-cell co-stimulator structurally and functionally related to CD28" I Nature, Jan. 21, 1999, 397:263-266.

Nestle, F.O. et al., "Vaccination of melanoma patients with peptide- or tumor lysate-pulsed dendritic cells", Nature Medicine, Mar. 1998.

Kugler, A. et al., "Regression of human metastatic renal cell carcinoma after vaccination with tumor cell-dendritic cell hybrids", Nature Medicine, Mar. 6, 2000, 3:332-336.

Dranoff, G. et al., "Vaccination with irradiated tumor cells engineered to secrete murine granulocyte-macrophage colony-stimulating factor stimulates potent, specific, and long-lasting anti-tumor immunity", Proc. Natl. Acad. Sci. U.S. Apr. 15, 1993.

Zalevsky, J. et al., "Enhanced antibody half-life improves in vivo activity", Nat. Biotechnol., Feb. 2010, 28 (2):157-159.

Petkova, S R . et al., "Enhanced half-life of genetically engineered human IgG1 antibodies in a humanized FcRn mouse model: potential application in humorally mediated autoimmune disease", Int. Immunol., Dec. 2006, 18 (12):1759-1769.

(56) References Cited

OTHER PUBLICATIONS

Le Mercier, I. et al., "Beyond CTLA-4 and PD-I, the Generation Z of Negative Checkpoint Regulators", Front. Immunol., Aug. 2015, (6), Article 418.
Kyi, C. et "Checkpoint blocking antibodies in cancer immunotherapy", FEBS Letters, 2014, 588:368-376.
Tansey M.G et al., "The TNF superfamily in 2009: new pathways, new indications, and new drugs", Drug Discovery Today, Dec. 2009.
Harlow, E. et al., "Antibodies, A Laboratory Manual", (1988), Cold Spring Harbor Publications, New York.
Lo, B.K.C., "Antibody engineering: Methods and Protocols, Methods in molecular biology", (2004) vol. 248. Humana Press, Clifton, N.J.
International Search Report and Written Opinion of the International Searching Authority issued on May 10, 2018 in PCT Application No. PCT/US17/69072.

* cited by examiner

Anti-TIGIT mab sequences

| Mab | Heavy Chain CDR1 | | Heavy Chain CDR2 | | Heavy Chain CDR3 | |
|---|---|---|---|---|---|---|
| T-01 | SDYAWN | (SEQ ID:1) | YISYSGSTGYNPSLKS | (SEQ ID:2) | RMIGYAMDY | (SEQ ID:3) |
| T-02 | SDYAWN | (1) | YITYSGGTSYNPSLKS | (SEQ ID:4) | RQIGLGFTY | (SEQ ID:5) |
| T-03 | DHTIH | (SEQ ID:6) | YFYPRDGSTKYNEKFKG | (SEQ ID:7) | GMLRWFAD | (SEQ ID:8) |
| T-04 | DHTIH | (6) | YIYPRDGSSKYNVKFKG | (SEQ ID:9) | GMLRWFAY | (SEQ ID:10) |
| T-05 | DQAIH | (SEQ ID:11) | YIYPRDGSTKYNETFKG | (SEQ ID:12) | GMLRWFAY | (10) |
| T-06 | SDYAWN | (1) | YITYSGSTSYNPSLKS | (SEQ ID:13) | RQVGLGFAY | (SEQ ID:14) |
| T-07 | SDSAWN | (SEQ ID:15) | YITYSGSTNYNPSLRS | (SEQ ID:16) | RQVGLGFAY | (14) |
| T-08 | NYGMN | (SEQ ID:17) | WINTYTGEPTYADDFKG | (SEQ ID:18) | APPYGYDVRFAY | (SEQ ID:19) |
| T-09 | TFAMGVG | (SEQ ID:20) | HIWWDDDKYYNPALKS | (SEQ ID:21) | MDYSYFAWFAY | (SEQ ID:22) |
| T-10 | SYYMH | (SEQ ID:23) | INPSGGRTSYAQMFQG | (SEQ ID:24) | DREEQWPVGGFDY | (SEQ ID:25) |

| Mab | Light Chain CDR1 | | Light Chain CDR2 | | Light Chain CDR3 | |
|---|---|---|---|---|---|---|
| T-01 | KASQDVSTVVA | (SEQ ID:26) | SASYRYT | (SEQ ID:27) | QQHYSTPWT | (SEQ ID:28) |
| T-02 | KASQDLSTAVA | (SEQ ID:29) | SSSYRYT | (SEQ ID:30) | QQHYSTPWT | (28) |
| T-03 | KASQDVSTTVA | (SEQ ID:31) | SASYRYT | (27) | QQHYSTPLT | (SEQ ID:32) |
| T-04 | KASQDVFTAVA | (SEQ ID:33) | SASYRYT | (27) | QQHYSIPLT | (SEQ ID:34) |
| T-05 | KASQDVSTAVA | (SEQ ID:35) | SASYRYT | (27) | QQHYSTPLT | (32) |
| T-06 | KASQDVSTAVA | (35) | SASYHYT | (SEQ ID:36) | QQHYSTPWT | (28) |
| T-07 | KASQDVSTAVA | (35) | SASYRFT | (SEQ ID:37) | QHHYSTPWT | (SEQ ID:38) |
| T-08 | RSSQSIVHSNGNTYLE | (SEQ ID:39) | KVSDRFS | (SEQ ID:40) | FQGSHVPWT | (SEQ ID:41) |
| T-09 | RSSTGAVTTSNYAN | (SEQ ID:42) | GTNNRAP | (SEQ ID:43) | ALWYSNHWV | (SEQ ID:44) |
| T-10 | RASQSIRRYLN | (SEQ ID:45) | SASNLQS | (SEQ ID:46) | QQSYIIPPT | (SEQ ID:47) |

*FIG. 3A*

Anti-PD1 mab sequences

| Mab | Heavy Chain CDR1 | | Heavy Chain CDR2 | | Heavy Chain CDR3 | |
|---|---|---|---|---|---|---|
| PD-01 | NFLMS | (SEQ ID:48) | TISGGGRDTYYVDSVKG | (SEQ ID:49) | RTTYSMDY | (SEQ ID:50) |
| PD-02 | NSYLY | (SEQ ID:51) | GINPSNGGTNFNEKFKT | (SEQ ID:52) | RDYNYDGGFDS | (SEQ ID:53) |
| PD-03 | NSYIY | (SEQ ID:54) | GINPSNGGTNFNEKFKT | (52) | RRDYRYDGGFDS | (SEQ ID:55) |
| PD-04 | NSYIY | (54) | GINPSNGGTNFNEKFKT | (52) | RDYNYDGGFDS | (53) |
| PD-05 | TYYIY | (SEQ ID:56) | GINPGNGGTNFNEKFKI | (SEQ ID:57) | RYHGYDGGLDY | (SEQ ID:58) |
| PD-06 | SYYIH | (SEQ ID:59) | WIFPGSGNSKYNENFKG | (SEQ ID:60) | SDYGSSPYYYFDY | (SEQ ID:61) |

| Mab | Light Chain CDR1 | | Light Chain CDR2 | | Light Chain CDR3 | |
|---|---|---|---|---|---|---|
| PD-01 | LASQTIGTWLA | (SEQ ID:62) | AATSLAD | (SEQ ID:63) | QQFYSIPWT | (SEQ ID:64) |
| PD-02 | RASSTLYSNYLH | (SEQ ID:65) | RASFLAS | (SEQ ID:66) | QQGSSIPLT | (SEQ ID:67) |
| PD-03 | SASSLYSSYLH | (SEQ ID:68) | RASFLAS | (66) | QQGSSIPLT | (67) |
| PD-04 | RASSLYSNYLH | (SEQ ID:69) | RASFLAS | (66) | QQGSSIPLT | (67) |
| PD-05 | RASKSVSTSGFSYIH | (SEQ ID:70) | LASNLES | (SEQ ID:71) | QHTWELPNT | (SEQ ID:72) |
| PD-06 | KASQNVGTNVA | (SEQ ID:73) | SASYRYS | (SEQ ID:74) | QQYYSYPYT | (SEQ ID:75) |

FIG. 3B

Anti-PD-L1 mab sequences

| Mab | Heavy Chain CDR1 | | Heavy Chain CDR2 | | Heavy Chain CDR3 | |
|---|---|---|---|---|---|---|
| PL-01 | NYWMH | (SEQ ID:76) | MIHPNTNNYNYNEKFKS | (SEQ ID:77) | SDYGSSPYYFDY | (SEQ ID:78) |
| PL-02 | SYWMH | (SEQ ID:79) | MIHPNVGSTNYNEKFKS | (SEQ ID:80) | SRYGSSPYYFDY | (SEQ ID:81) |
| PL-03 | SYWMH | (79) | MIHPNSGGNNYNEKFKS | (SEQ ID:82) | SWYGSSPYYFDY | (SEQ ID:83) |
| PL-04 | SYWMH | (79) | MIHPTGVSTDYNEKFKS | (SEQ ID:84) | SDYGSSPYYFDY | (78) |
| PL-05 | SDYAWN | (SEQ ID:85) | YISDSGSTSYNPSLKS | (SEQ ID:86) | SFLRLRSYFDH | (SEQ ID:87) |
| PL-06 | SYGIN | (SEQ ID:88) | CIYIGNDYTNYNEKFKG | (SEQ ID:89) | AYYGSRVDY | (SEQ ID:90) |
| PL-07 | SYGIN | (88) | CIYIGNDYTNYNEKFKG | (89) | AYYGSRVDY | (90) |
| PL-08 | SYWMH | (79) | MIHPNSGGNNYNEKFKS | (82) | SWYGSSPYYFDY | (83) |

| Mab | Light Chain CDR1 | | Light Chain CDR2 | | Light Chain CDR3 | |
|---|---|---|---|---|---|---|
| PL-01 | RASQDIDNYLN | (SEQ ID:91) | YTSRLHS | (SEQ ID:92) | QQGYTLPWT | (SEQ ID:93) |
| PL-02 | RASQDISNYLN | (SEQ ID:94) | YTSRLQS | (SEQ ID:95) | QQGNTLPWT | (SEQ ID:96) |
| PL-03 | RASQDISNYLN | (94) | YTSRLHS | (92) | QQGNTLPWT | (96) |
| PL-04 | RASQDISNYLN | (94) | YTSRLHS | (92) | QQGDTLPWT | (SEQ ID:97) |
| PL-05 | KASQDVNVAVA | (SEQ ID:98) | WASTRHI | (SEQ ID:99) | QQHYSTPYT | (SEQ ID:100) |
| PL-06 | KASQDINKYIA | (SEQ ID:101) | YTSTLQP | (SEQ ID:102) | LQYDNLYT | (SEQ ID:103) |
| PL-07 | QSISDYLH | (SEQ ID:104) | CASQSISG | (SEQ ID:105) | QNGHSFPYT | (SEQ ID:106) |
| PL-08 | RASQDIDNYLN | (91) | YTSRLHS | (92) | QQGYTLPWT | (93) |

FIG. 3C

Anti-TIGIT Antibody Variable Domain Sequences

T-01
VH (SEQ ID NO: 107)
QVQLQESGPGLVKPSQTLSLTCTVSGYSITSDYAWNWIRQPPGKGLEWIGYISYSGST
GYNPSLKSRVTISVDTSKNQFSLKLSSVTAADTAVYYCARRMIGYAMDYWGQGTSV
TVSS

VL (SEQ ID NO: 108)
DIQMTQSPSSLSASVGDRVTITCKASQDVSTVVAWHQQKPGKAPKLLIYSASYRYTG
VPSRFSGSGSGTDFTLTISSLQPEDFATYYCQQSYSTPQQHYSTPWTFGGGTKLEIKR

T-02
VH (SEQ ID NO: 109)
QVKLQESGPGLVKPSQTLSLTCTVTGYSITSDYAWNWIRQPPGKGLEWIGYITYSGG
TSYNPSLKSRVTISVDTSKNQFSLKLSSVTAADTAVYSCARRQIGLGFTYWGQGTLV
TVSA

VL (SEQ ID NO: 110)
DIQMTQSPSSLSASVGDRVTIPCKASQDLSTAVAWYQQKPGKAPKLLIYSSSYRYTG
VPSRFSGSGSGTDFTLTISSLQPEDFATYYCQQSYSTPQQHYSTPWTFGEGTKLEIK

T-03
VH (SEQ ID NO: 111)
EVQLVQSGAEVKKPGATVKISCKVSGYTFTDHTIHWVQQAPGKGLEWMGYFYPRD
GSTKYNEKFKGRVTITADTSTDTAYMELSSLRSEDTAVYYCATGMLRWFADWGQG
TLITVSVA

VH (SEQ ID NO: 112)
DIQMTQSPSSLSASVGDRVTITCKASQDVSTTVAWYQQKPGKAPKLLIYSASYRYTG
VPSRFSGSGSGTDFTLTISSLQPEDFATYYCQQHYSTPLTFGAGTKLELK

FIG. 4A

T-04
VH (SEQ ID NO: 113):
EVQLVQSGAEVKKPGATVKISCKVSGYTFTDHTIHWVQQAPGKGLEWMGYIYPRDG
SSKYNVKFKGRVTITADTSTDTAYMELSSLRSEDTAVYYCATGMLRWFAYWGQGT
LVTVSS

VL (SEQ ID NO: 114):
DIQMTQSPSSLSASVGDRVTITCKASQDVFTAVAWYQQKPGKAPKLLIYSASYRYTG
VPSRFSGSGSGTDFTFTISSLQPEDIATYYCQQHYSIPLTFGAGTKLEIK

T-05
VH (SEQ ID NO: 115):
EVQLKQSGAEVKKPGATVKISCKVSGYTFTDQAIHWVQQAPGKGLEWMGYIYPRD
GSTKYNETFKGRVTITADTSTDTAYMELSSLRSEDTAVYFCARGMLRWFAYWGQGT
LVTVSS

VL (SEQ ID NO: 116):
DIQMTQSPSSLSASVGDRVTITCKASQDVSTAVAWYQQKPGKAPKLLIYSASYRYTG
VPSRFSGSGSGTDFTLTISSLQPEDFATYYCQQHYSTPLTFGAGTKLELK

T-06
VH (SEQ ID NO: 117):
QVQLQESGPGLVKPSQTLSLTCTVSGGSVSSDYAWNWIRQPPGKGLEWIGYITYSGS
TSYNPSLKSRVTISVDTSKNQFSLKLSSVTAADTAVYYCARRQVGLGFAYWGQGTL
VTVSA

VL (SEQ ID NO: 118):
DIQMTQSPSSLSASVGDRVTITCKASQDVSTAVAWYQQKPGKAPKLLIYSASYHYTG
VPSRFSGSGSGTDFTLTISSLQPEDFATYYCQQHYSTPWTFGGGTKLEIK

T-07
VH (SEQ ID NO: 119):
EVQLQESGPGLVKPSDTLSLTCAVSGYSITSDSAWNWIRQPPGKGLEWIGYITYSGST
NYNPSLRSRVTMSVDTSKNQFSLKLSSVTAVDTAVYYCTRRQVGLGFAYWGQGTL
VTVSA

VL (SEQ ID NO: 120):
DIQMTQSPSSLSASVGDRVTITCKASQDVSTAVAWYQQKPGKAPKLLIYSASYRFTG
APSRFSGSGSGTDFTLTISSLQPEDFGIYYCQHHYSTPWTFGGGTKLEFK

FIG. 4B

T-08
VH (SEQ ID NO: 121):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSS

VL (SEQ ID NO: 122):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIK

T-09
VH (SEQ ID NO: 123):
QVTLKESGPTLVKPTQTLTLTCTFSGFSLSTFAMGVGWIRQPPGKALEWLAHIWWDD
DKYYNPALKSRLTITKDTSKNQVVLTMTNMDPVDTATYYCARMDYSYFAWFAYW
GQGTLVTVSS

VL (SEQ ID NO: 124):
QAVVTQEPSLTVSPGGTVTLTCRSSTGAVTTSNYANWVQQKPGQLFRGLIGGTNNR
APWVPARFSGSLIGDKAALTLSGVQPEDEAEYFCALWYSNHWVFGGGTKLTVL

T-10
VH (SEQ ID NO: 125):
QVQLVQSGAEVKKPGASVKVSCKASGYTFTSYYMHWVRQAPGQGLEWMGIINPSG
GRTSYAQMFQGRVTMTRDTSTSTVYMELSSLRSEDTAVYYCARDREEQWPVGGFD
YWGQGTLVTVSS

VL (SEQ ID NO: 126):
DIQMTQSPSSLSASVGDRVTITCRASQSIRRYLNWYQQKPGKAPKLLIYSASNLQSGV
PSRFSGSGSGTDFTLTISSLQPEDFATYYCQQSYIIPPTFGQGTKVEIK

FIG. 4C anti-PD1 Antibody Variable Domain Sequences

PD-01
VH (SEQ ID NO: 127):
EVQLVESGGGLVQPGGSLRLSCAASGFTFSNFLMSWVRQAPGKGLEWVSTISGGGR
DTYYVDSVKGRFTISRDNSKNTLYLQMNSLRAEDTAVYYCAKRTTYSMDYWGQGT
SVTVSS

VL (SEQ ID NO: 128):
DIQMTQSPSSVSASVGDRVTITCLASQTIGTWLAWYQQKPGKAPKLLIYAATSLADG
VPSRFSGSGSGTDFTLTISSLQPEDFATYYCQQFYSIPWTFGGGTKLEIK

PD-02
VH (SEQ ID NO: 129):
QVQLVQSGAEVKKPGASVKVSCKASDYTFTNSYLYWLRQAPGQGLEWMGGINPSN
GGTNFNEKFKTRTTSTRDTSISTAYMELSRLRSDDTVVYYCTRRDYNYDGGFDSWG
QGTLVTVSS

VL (SEQ ID NO: 130):
DIQMTQSPSSLSASVGDRVTFTCRASSTLYSNYLHWYQQKPGKAPKLLIYRASFLAS
GVPSRFSGSGSGTDFTLTISSLQPEDFATYYCQQGSSIPLTFGGGTKVEIK

PD-03
VH (SEQ ID NO: 131)
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYRYDGGFDSWG
QGTTLTVSS

VL (SEQ ID NO: 132)
DIQMTQSPSSLSASVGDRVTITCSASSSLYSSYLHWYQQKPGKAPKLLIYRASFLASG
VPSRFSGSGSGTDFTLTISSLQPEDFATYYCQQGSSIPLTFGAGTKLDLK

FIG. 4D

PD-04
VH (SEQ ID NO: 133):
QVQLVQSGAEVKKPGASVKVSCKASDYTFTNSYIYWVRQAPGQGLEWMGGINPSN
GGTNFNEKFKTRVTSTRDTSISTAYMELSRLRSDDTVVYYCARRDYNYDGGFDSWG
QGTLVTVSS

VL (SEQ ID NO: 134):
DIQMTQSPSSLSASVGDRVTFTCRASSSLYSNYLHWYQQKPGKAPKLLIYRASFLAS
GVPSRFSGSGSGTDFTLTISSLQPEDFATYYCQQGSSIPLTFGGGTKVEIK

PD-05
VH (SEQ ID NO: 135):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSS

VL (SEQ ID NO: 136):
DIVLTQSPASLAVSPGQRATITCRASKSVSTSGFSYIHWYQQKPGQPPKLLIYLASNLE
SGVPARFSGSGSGTDFTLTINPVEANDTANYYCQHTWELPNTFGGGTKVEIK

PD-06
VH (SEQ ID NO: 137):
QVQLVQSGAEVKKPGASVKVSCKASGYTFTSYYIHWVRQAPGQRLEWMGWIFPGS
GNSKYNENFKGRVTITRDTSASTAYMELSSLRSEDTAVYFCASETYDYGDYWGQGT
LVTVSS

VL (SEQ ID NO: 138):
DIQMTQSPSSLSASVGDRVTITCKASQNVGTNVAWYQQKPGKAPKSLIYSASYRYSG
VPSRFSGSGSGTDFTLTISSLQPEDFATYFCQQYYSYPYTFGQGTKLEIK

FIG. 4E anti-PD-L1 Antibody Variable Domain Sequences

PL-01
VH (SEQ ID NO: 139):
QVQLVQSGAEVKKPGASVKVSCKASGYTFTNYWMHWMKQAPGQGLEWMGMIHP
NTNNYNYNEKFKSRVTSTRDTSISTAYMELSRLRSDDTVVYYCARSDYGSSPYYFDY
WGQGTLVTVSS

VL (SEQ ID NO: 140):
DIQMTQSPSSLSASVGDRVTISCRASQDIDNYLNWYQQKPGKAPKLLIKYTSRLHSG
VPSRFSGSGSGTDFTLTISSLQPEDFATYFCQQGYTLPWTFGGGTKVEIK

PL-02
VH (SEQ ID NO: 141):
QVQLVQSGAEVKKPGASVKVSCKASGYTFTSYWMHWVRQAPGQGLEWMGMIHPN
VGSTNYNEKFKSKATMTRDKSSSTVYMELSSLRSEDTAVYYCARSRYGSSPYYFDY
WGQGTLVTVSS

VL (SEQ ID NO: 142):
DIQMTQSPSSLSASVGDRVTISCRASQDISNYLNWYQQKPGKAPKLLIYYTSRLQSGV
PSRFSGSGSGTDFTFTISSLQPEDIATYFCQQGNTLPWTFGQGTKVEIK

PL-03
VH (SEQ ID NO: 143):
QVQLVQSGAEVKKPGASVKVSCKASGYTFTSYWMHWVRQAPGQGLEWMGMIHPN
SGGNNYNEKFKSRVTMTRDTSISTAYMELSRLRSDDTAVYYCARSWYGSSPYYFDY
WGQGTLVTVSS

VL (SEQ ID NO: 144):
DIQMTQSPSSLSASVGDRVTISCRASQDISNYLNWYQQKPGKAPKLLIYYTSRLHSGV
PSRFSGSGSGTDFTFTISSLQPEDIATYFCQQGNTLPWTFGQGTKVEIK

*FIG. 4F*

PL-04
VH (SEQ ID NO: 145):
QVQLVQSGAEVKKPGASVKVSCKASGYTFTSYWMHWVRQAPGQGLEWMGMIHPT
GVSTDYNEKFKSRVTMTRDTSTSTVYMELSSLRSEDTAVYYCARSDYGSSPYYFDY
WGQGTLVTVSS

VL (SEQ ID NO: 146):
DIQMTQSPSSLSASVGDRVTISCRASQDISNYLNWYQQKPGKAPKLLIKYTSRLHSGV
PSRFSGSGSGTDFTLTISSLQPEDFATYFCQQGDTLPWTFGGGTKVEIK

PL-05
VH (SEQ ID NO: 147):
DVQLQESGPGLVKPSQSLSLTCTVTGYSITSDYAWNWIRQFPGNKLEWMGYISDSGS
TSYNPSLKSRISITRDTSKNQFFLQLNSVTTEDTATYYCANSFLRLRSYFDHWGQGTT
LTVSS

VL (SEQ ID NO: 148):
DIVMTQSHKFMSTSVGDRVSITCKASQDVNVAVAWYQQKPGQSPKLLIFWASTRHI
GVPDRFTGSGSGTDYTLTISSVQAEDLALYYCQQHYSTPYTFGGGTKLEIK

PL-06
VH (SEQ ID NO: 149):
QVQLVQSGAEVKKPGASVKVSCKASGYTFTSYGINWVRQAPGQRLEWMGWCIYIG
NDYTNYNEKFKGRVTITRDTSASTAYMELSSLRSEDTAVYYCARAYYGSRVDYWG
QGTLVTVSS

VL (SEQ ID NO: 150):
DIQMTQSPSSLSAFVGDRVTITCKASQDINKYIAWYQQKPGKAPKLLIHYTSTLQPGV
PSRFSGSGSGRDFTFTISSLQPEDIATYYCLQYDNLYTFGGGTKVEIK

PL-07
VH (SEQ ID NO: 151):
QVQLVQSGAEVKKPGASVKVSCKASGYTFTSYGINWVRQAPGQRLEWMGWCIYIG
NDYTNYNEKFKGRVTITRDTSASTAYMELSSLRSEDTAVYYCARAYYGSRVDYWG
QGTLVTVSS

VL (SEQ ID NO: 152):
EIVLTQSPVTLSLSPGERATLSCQSISDYLHWYLQKPGQAPRLLIKCASQSISGIPARFS
GSGSGSDFTLTISSLEPEDFAVYYCQNGHSFPYTFGGGTKVEIK

FIG. 4G

PL-08
VH (SEQ ID NO: 153):
QVQLVQSGAEVKKPGASVKVSCKASGYTFTSYWMHWVRQAPGQGLEWMGMIHPN
SGGNNYNEKFKSRVTMTRDTSISTAYMELSRLRSDDTAVYYCARSWYGSSPYYFDY
WGQGTLVTVSS

VL (SEQ ID NO: 154):
DIQMTQSPSSLSASVGDRVTISCRASQDIDNYLNWYQQKPGKAPKLLIKYTSRLHSG
VPSRFSGSGSGTDFTLTISSLQPEDFATYFCQQGYTLPWTFGGGTKVEIK

FIG. 4H

Exemplary bispecific inhibitory antibody sequences against PD1 and TIGIT

1. TP-M2T8P5

VH (SEQ ID NO: 155):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSGGGGSQVQLVQSGAEVKKPGASVKVSCKASGYTFTTYYIYWVRQ
APGQGLEWMGGINPGNGGTNFNEKFKIRVTMTRDTSISTAYMELSSLRSEDTAVYYC
ARRYHGYDGGLDYWGQGTLVTVSS

VL (SEQ ID NO: 156):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIK**GGG
GSGGGGSGGGGS**DIVLTQSPASLAVSPGQRATITCRASKSVSTSGFSYIHWYQQKPG
QPPKLLIYLASNLESGVPARFSGSGSGTDFTLTINPVEANDTANYYCQHTWELPNTFG
GGTKVEIK

2. TP-M4T8P5

VL2/VH1 (SEQ ID NO: 157):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIK**RTV
AAPSVFIFPP**QVQLVQSGAEVKKPGASVKVSCKASGYTFTTYYIYWVRQAPGQGLE
WMGGINPGNGGTNFNEKFKIRVTMTRDTSISTAYMELSSLRSEDTAVYYCARRYHG
YDGGLDYWGQGTLVTVSS

VH2/VL1 (SEQ ID NO: 158):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPDIVLTQSPASLAVSPGQRATITCRASKSVSTSGF
SYIHWYQQKPGQPPKLLIYLASNLESGVPARFSGSGSGTDFTLTINPVEANDTANYYC
QHTWELPNTFGGGTKVEIK

VH (SEQ ID NO: 159):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGGGGSG
GGGSGGGGSDIVLTQSPASLAVSPGQRATITCRASKSVSTSGFSYIHWYQQKPGQPPK
LLIYLASNLESGVPARFSGSGSGTDFTLTINPVEANDTANYYCQHTWELPNTFGGGTK
VEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

VL2/CL (SEQ ID NO: 160):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

VH1/CH1 (SEQ ID NO: 161):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSSASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRVESKYGPPC
PPCPAPEFLGG

VH (SEQ ID NO: 162):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGGGGSG
GGGSGGGGSDIQMTQSPSSLSASVGDRVTISCRASQDIDNYLNWYQQKPGKAPKLLI
KYTSRLHSGVPSRFSGSGSGTDFTLTISSLQPEDFATYFCQQGYTLPWTFGGGTKVEI
KRTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

VL2/CL (SEQ ID NO: 163):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

VH1/CH1 (SEQ ID NO: 164):
QVQLVQSGAEVKKPGASVKVSCKASGYTFTSYWMHWVRQAPGQGLEWMGMIHPN
SGGNNYNEKFKSRVTMTRDTSISTAYMELSRLRSDDTAVYYCARSWYGSSPYYFDY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGG

5. TP-M8T10P1 (TP-83)

VH (SEQ ID NO: 165):
QVQLVQSGAEVKKPGASVKVSCKASGYTFTSYYMHWVRQAPGQGLEWMGIINPSG
GRTSYAQMFQGRVTMTRDTSTSTVYMELSSLRSEDTAVYYCARDREEQWPVGGFD
YWGQGTLVTVSS

LC (SEQ ID NO: 166):
DIQMTQSPSSLSASVGDRVTITCRASQSIRRYLNWYQQKPGKAPKLLIYSASNLQSGV
PSRFSGSGSGTDFTLTISSLQPEDFATYYCQQSYIIPPTFGQGTKVEIRRTVAAPSVFIFP
PSDEQLKSGTASVVCLLNNFYPREAKVQWKVDNALQSGNSQESVTEQDSKDSTYSL
SSTLTLSKADYEKHKVYACEVTHQGLSSPVTKSFNRGECGGGGSGGGGSEVQLVES
GGGLVQPGGSLRLSCAASGFTFSNFLMSWVRQAPGKGLEWVSTISGGGRDTYYVDS
VKGRFTISRDNSKNTLYLQMNSLRAEDTAVYYCAKRTTYSMDYWGQGTSVTVSSG
GGGSGGGGSGGGGSDIQMTQSPSSVSASVGDRVTITCLASQTIGTWLAWYQQKPGK
APKLLIDAATSLADGVPSRFSGSGSGTDFTLTISSLQPEDFATYYCQQFYSIPWTFGGG
TKLEIK

HC (SEQ ID NO: 167):
EVQLVESGGGLVQPGGSLRLSCAASGFTFSNFLMSWVRQAPGKGLEWVSTISGGGR
DTYYVDSVKGRFTISRDNSKNTLYLQMNSLRAEDTAVYYCAKRTTYSMDYWGQGT
SVTVSSASTKGPSVFPLAPCSRSTSESTAALGCLVKDYFPEPVTVSWNSGALTSGVHT
FPAVLQSSGLYSLSSVVTVPSSSLGTKTYTCNVDHKPSNTKVDKRVESKYGPPCPPCP
APEFLGGPSVFLFPPKPKDTLMISRTPEVTCVVVDVSQEDPEVQFNWYVDGVEVHNA
KTKPREEQFNSTYRVVSVLTVLHQDWLNGKEYKCKVSNKGLPSSIEKTISKAKGQPR
EPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGKGGGGSGGGGS
QVQLVQSGAEVKKPGASVKVSCKASGYTFTSYYMHWVRQAPGQGLEWMGIINPSG
GRTSYAQMFQGRVTMTRDTSTSTVYMELSSLRSEDTAVYYCARDREEQWPVGGFD
YWGQGTLVTVSSGGGGSGGGGSGGGGSDIQMTQSPSSLSASVGDRVTITCRASQSIR
RYLNWYQQKPGKAPKLLIYSASNLQSGVPSRFSGSGSGTDFTLTISSLQPEDFATYYC
QQSYIIPPTFGQGTKVEIK

LC (SEQ ID NO: 168):
DIQMTQSPSSVSASVGDRVTITCLASQTIGTWLAWYQQKPGKAPKLLIDAATSLADG
VPSRFSGSGSGTDFTLTISSLQPEDFATYYCQQFYSIPWTFGGGTKLEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC

7. TP-M9T10P5

HC (SEQ ID NO: 169):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSSASTKGPSVFPLAPCSRSTSESTAALGCLVKDYFPEPVTVSWNSGALTSG
VHTFPAVLQSSGLYSLSSVVTVPSSSLGTKTYTCNVDHKPSNTKVDKRVESKYGPPC
PPCPAPEFLGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSIEKTISKAK
GQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGGGGSGGG
GSQVQLVQSGAEVKKPGASVKVSCKASGYTFTSYYMHWVRQAPGQGLEWMGIINP
SGGRTSYAQMFQGRVTMTRDTSTSTVYMELSSLRSEDTAVYYCARDREEQWPVGG
FDYWGQGTLVTVSSGGGGSGGGGSGGGGSDIQMTQSPSSLSASVGDRVTITCRASQS
IRRYLNWYQQKPGKAPKLLIYSASNLQSGVPSRFSGSGSGTDFTLTISSLQPEDFATY
YCQQSYIIPPTFGQGTKVEIK

LC (SEQ ID NO: 170):
DIVLTQSPASLAVSPGQRATITCRASKSVSTSGFSYIHWYQQKPGQPPKLLIYLASNLE
SGVPARFSGSGSGTDFTLTINPVEANDTANYYCQHTWELPNTFGGGTKVEIK

HC (SEQ ID NO: 171):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGKGGGG
SGGGGSQVQLVQSGAEVKKPGASVKVSCKASGYTFTTYYIYWVRQAPGQGLEWMG
GINPGNGGTNFNEKFKIRVTMTRDTSISTAYMELSSLRSEDTAVYYCARRYHGYDGG
LDYWGQGTLVTVSSGGGGSGGGGSGGGGSDIVLTQSPASLAVSPGQRATITCRASKS
VSTSGFSYIHWYQQKPGQPPKLLIYLASNLESGVPARFSGSGSGTDFTLTINPVEAND
TANYYCQHTWELPNTFGGGTKVEIK

VL (SEQ ID NO: 172):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIK

9. TP-M10T8L8 (SEQ ID NO: 173):

QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGKGGGG
SGGGGSQVQLVQSGAEVKKPGASVKVSCKASGYTFTSYWMHWVRQAPGQGLEW
MGMIHPNSGGNNYNEKFKSRVTMTRDTSISTAYMELSRLRSDDTAVYYCARSWYGS
SPYYFDYWGQGTLVTVSSGGGGSGGGGSGGGGSDIQMTQSPSSLSASVGDRVTISCR
ASQDIDNYLNWYQQKPGKAPKLLIKYTSRLHSGVPSRFSGSGSGTDFTLTISSLQPED
FATYFCQQGYTLPWTFGGGTKVEIK

VH2/CH1 (SEQ ID NO: 174):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEKMTKNQVSLTCLVKGFYPSDIAVEWESNGQPENNYKTT
PPVLKSDGSFFLYSRLTVDKSRWQEGNVFSCSVMHEALHNHYTQKSLSLSLGK

VL1/CH1 (SEQ ID NO: 175):
DIVLTQSPASLAVSPGQRATITCRASKSVSTSGFSYIHWYQQKPGQPPKLLIYLASNLE
SGVPARFSGSGSGTDFTLTINPVEANDTANYYCQHTWELPNTFGGGTKVEIKASTKG
PSVFPLAPCSRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAPEFLGGPSVF
LFPPKPKDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQVYTLPPS
QEEMTKNQVSLTCLVEGFYPSDIAVEWESNGQPENNYATTPPVLDSDGSFFLYSDLT
VDKSRWQEGNVFSCSVMHEALHNHYTQKSLSLSLGK

VL2/CL (SEQ ID NO: 176):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

VH1/CL (SEQ ID NO: 177):
QVQLVQSGAEVKKPGASVKVSCKASGYTFTTYYIYWVRQAPGQGLEWMGGINPGN
GGTNFNEKFKIRVTMTRDTSISTAYMELSSLRSEDTAVYYCARRYHGYDGGLDYWG
QGTLVTVSSGGGGSRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTK
SFNRGEC

VH2/HC1 (SEQ ID NO: 178):
QVQLVQSGSELKKPGASVKVSCKASGYTFTNYGMNWVRQAPGQGLEWMGWINTY
TGEPTYADDFKGRFVFSLDTSVSTAYLQISSLKAEDTAVYYCARAPPYGYDVRFAY
WGQGTLVTVSSASTKGPSVFPLAPCSRSTSESTAALGCLVKDYFPEPVTVSWNSGAL
TSGVHTFPAVLQSSGLYSLSSVVTVPSSSLGTKTYTCNVDHKPSNTKVDKRVESKYG
PPCPPCPAPEFLGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSSIEKTISK
AKGQPREPQVYTLPPSQEKMTKNQVSLTCLVKGFYPSDIAVEWESNGQPENNYKTT
PPVLKSDGSFFLYSRLTVDKSRWQEGNVFSCSVMHEALHNHYTQKSLSLSLGK

VL1/HC2 (SEQ ID NO: 179):
DIQMTQSPSSLSASVGDRVTISCRASQDIDNYLNWYQQKPGKAPKLLIKYTSRLHSG
VPSRFSGSGSGTDFTLTISSLQPEDFATYFCQQGYTLPWTFGGGTKVEIKASTKGPSVF
PLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPP
KPKDTLMISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYTLPPSQEEM
TKNQVSLTCLVEGFYPSDIAVEWESNGQPENNYATTPPVLDSDGSFFLYSDLTVDKS
RWQEGNVFSCSVMHEALHNHYTQKSLSLSLGK

VL2/CL (SEQ ID NO: 180):
DVVMTQSPLSLPVTLGQPASISCRSSQSIVHSNGNTYLEWFQQRPGQSPRVLIYKVSD
RFSGVPDRFSGSGSGTDFTLKISRVEAEDVGVYYCFQGSHVPWTFGRGTKLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

VH1/CL (SEQ ID NO: 181):
QVQLVQSGAEVKKPGASVKVSCKASGYTFTSYWMHWVRQAPGQGLEWMGMIHPN
SGGNNYNEKFKSRVTMTRDTSISTAYMELSRLRSDDTAVYYCARSWYGSSPYYFDY
WGQGTLVTVSSGGGGSRTVAAPSVFIFPPSDEQLKSGTASVVCLLNNFYPREAKVQ
WKVDNALQSGNSQESVTEQDSKDSTYSLSSTLTLSKADYEKHKVYACEVTHQGLSS
PVTKSFNRGEC

FIG. 5G

Human PD-1-His

| Ab | $K_D$ (nM) | $K_a$ (M$^{-1}$s$^{-1}$) | $K_d$ (s$^{-1}$) |
|---|---|---|---|
| PD-01 | 2.2 | 1.26E+05 | 2.72E-04 |
| PD-02 | 3.7 | 1.06E+05 | 3.95E-04 |
| BM | 4.0 | 2.03E+05 | 8.23E-04 |

Anti-PD-1 = PD-01
Anti-TIGIT = T-08

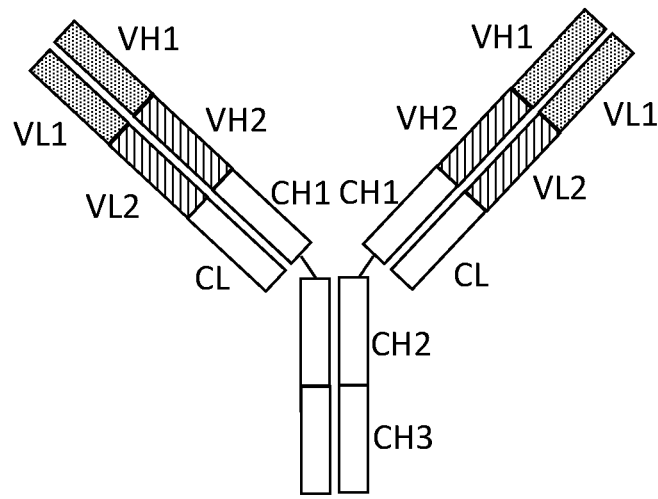
FIG. 17A (M1)
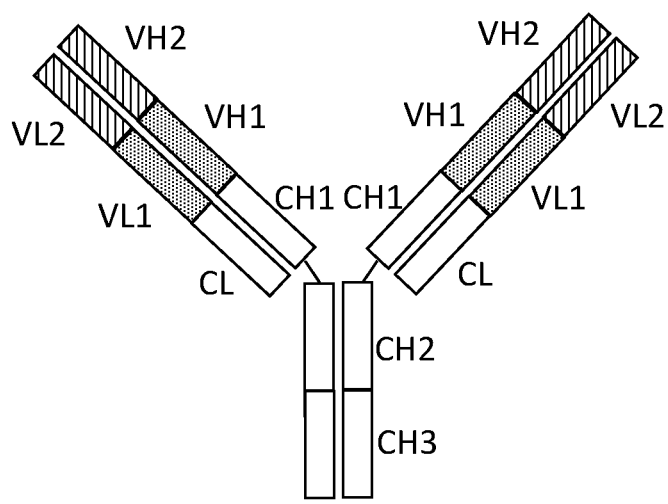
FIG. 17B (M2)
VH1 VL1 = Anti PD1, PDL1 or any other mAb variable domain
VH2 VL2 = Anti TIGIT variable domain

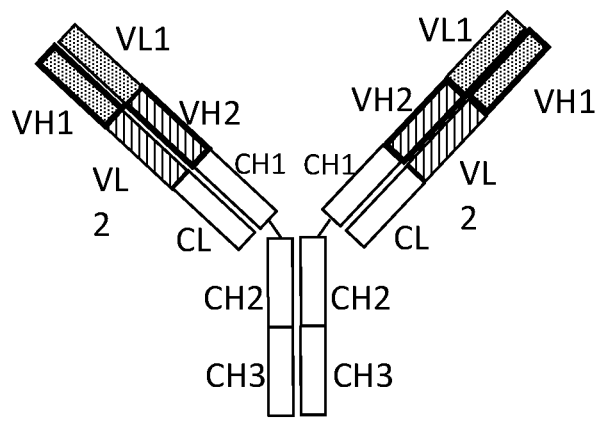
FIG. 17C (M3)
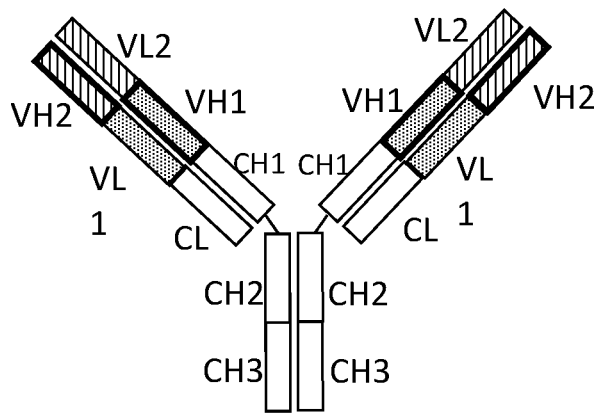
FIG. 17D (M4)
VH1 VL1 = Anti TIGIT variable domain
VH2 VL2 = Anti PD1, PDL1 or any other mAb variable domain

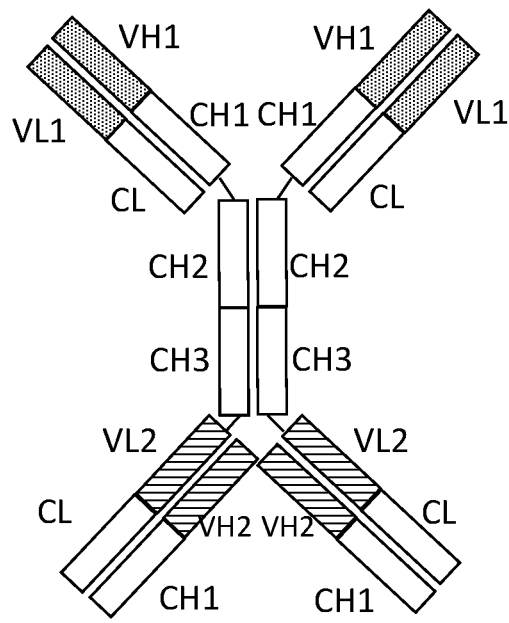
FIG. 17E (M5)
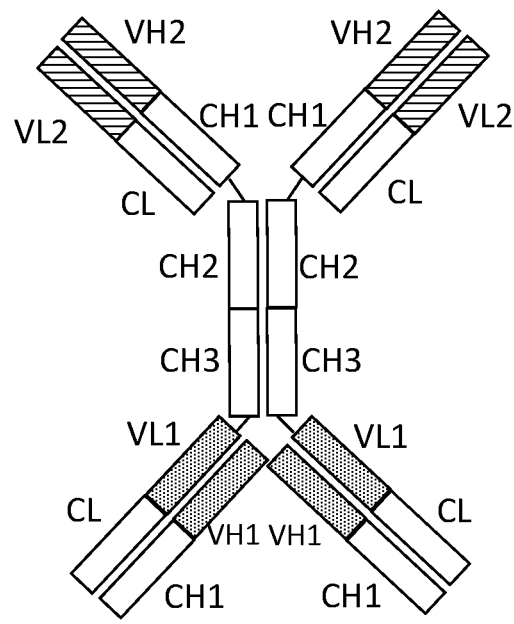
FIG. 17F (M6)
VH1 VL1 = Anti PD1, PDL1 or any other mAb variable domain
VH2 VL2 = Anti TIGIT variable domain

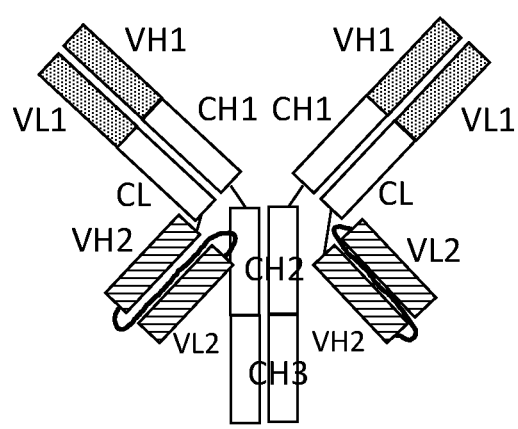
FIG. 17G (M7)
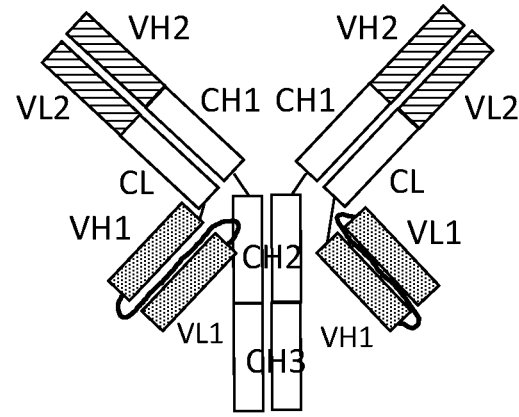
FIG. 17H (M8)
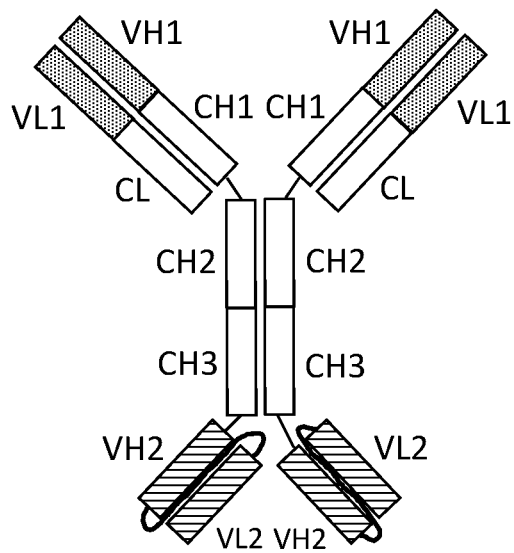
FIG. 17I (M9)
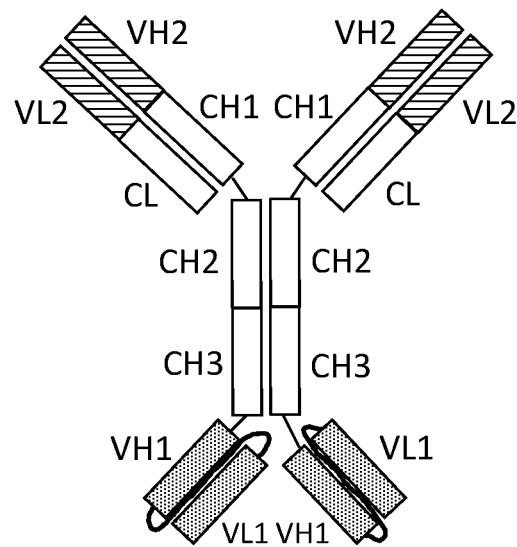
FIG. 17J (M10)
VH1 VL1 = Anti PD1, PDL1 or any other mAb variable domain
VH2 VL2 = Anti TIGIT variable domain

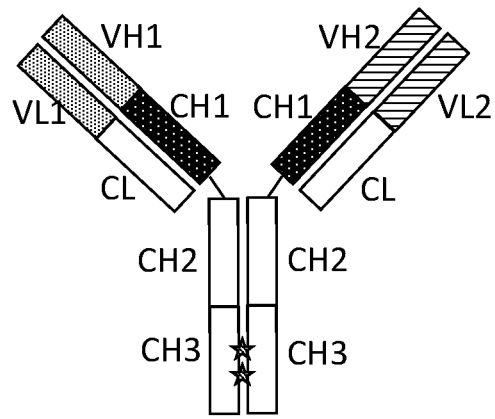
FIG. 17K (M11)
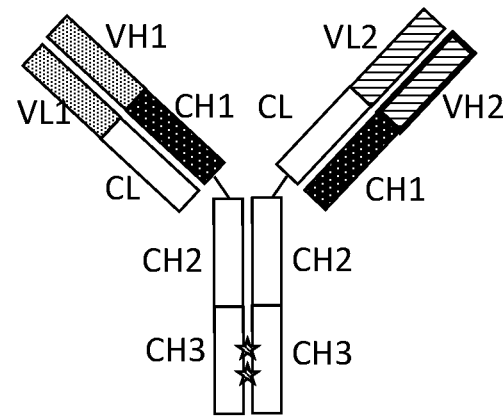
FIG. 17L (M12)
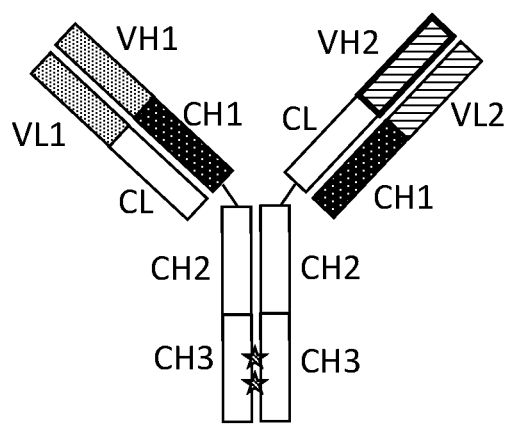
FIG. 17M (M13)
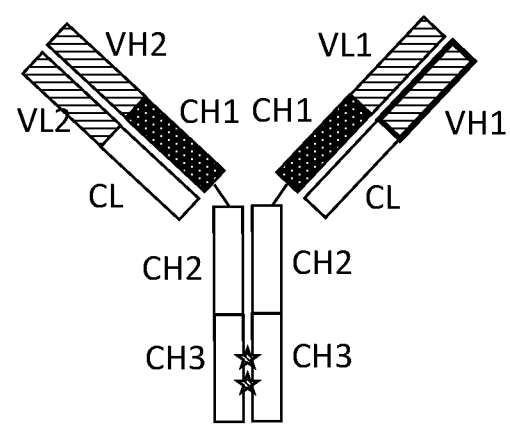
FIG. 17N (M14)
VH1 VL1 = Anti PD1, PDL1 or any other mAb variable domain
VH2 VL2 = Anti TIGIT variable domain VH1 VL1 = Anti TIGIT variable domain
VH2 VL2 = Anti PD1, PDL1 or any other mAb variable domain
● = AMG386 or other biological peptide

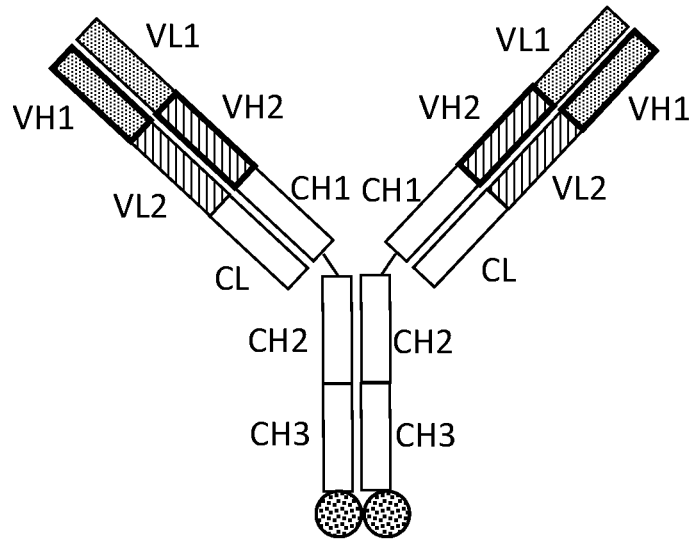
FIG. 18C
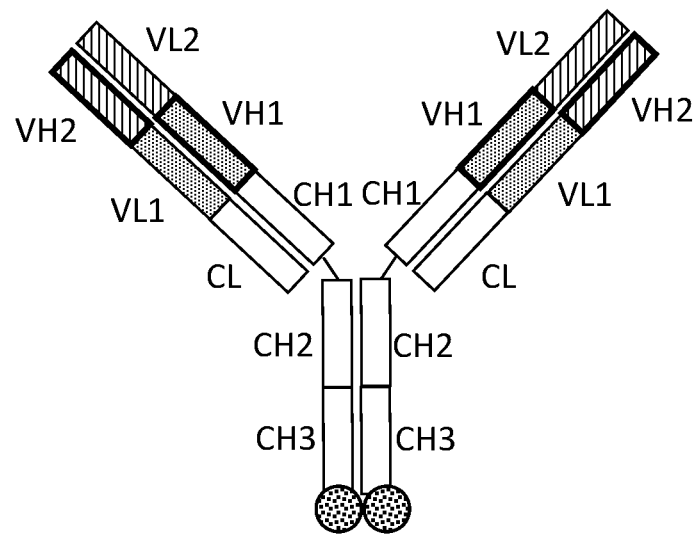
FIG. 18D
VH1 VL1 = Anti TIGIT variable domain
VH2 VL2 = Anti PD1, PDL1 or any other mAb variable domain
 = AMG386 or other biological peptide VH1 VL1 = Anti TIGIT variable domain
VH2 VL2 = Anti PD1, PDL1 or any other mAb variable domain
● = AMG386 or other biological peptide

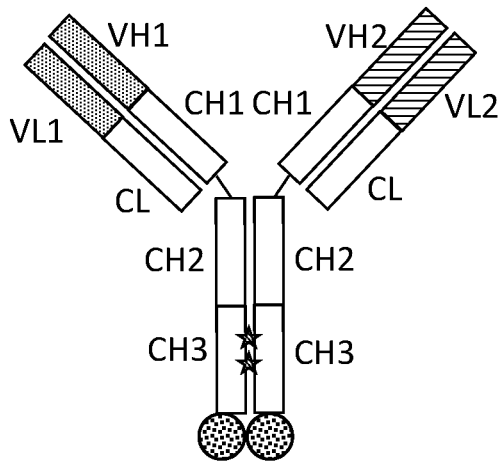
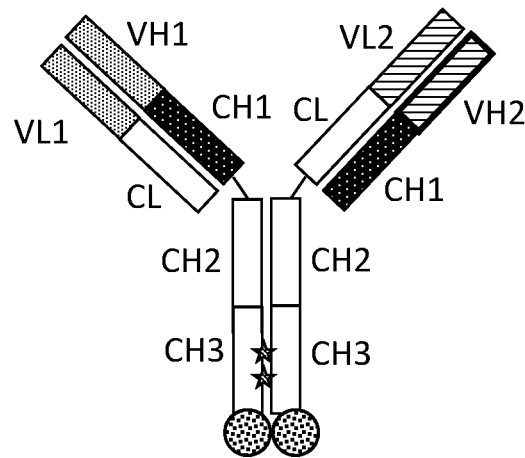
*FIG. 18G*  *FIG. 18H*
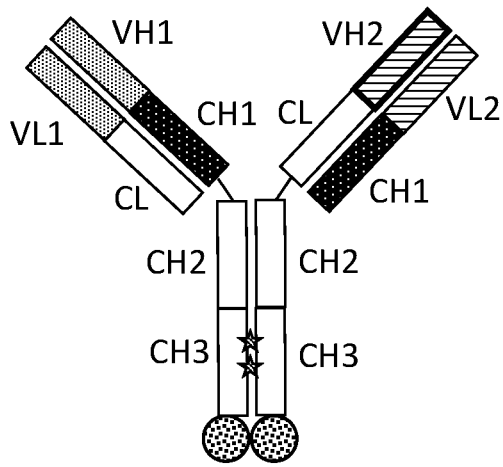
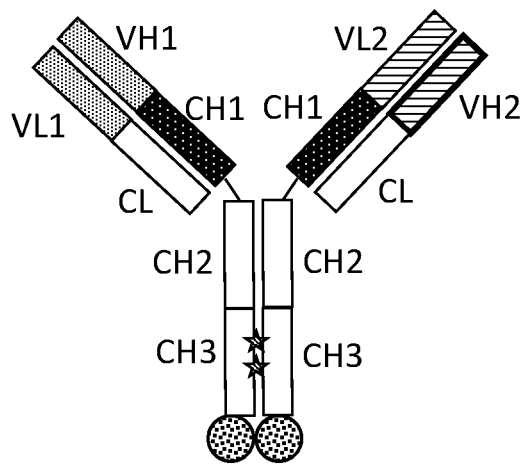
*FIG. 18I*  *FIG. 18J*
VH1 VL1 = Anti TIGIT variable domain
VH2 VL2 = Anti PD1, PDL1 or any other mAb variable domain
 = AMG386 or other biological peptide

CHECKPOINT REGULATOR ANTAGONISTS

This application is a Continuation Application of U.S. application Ser. No. 16/696,253, filed Nov. 26, 2019, which is a Continuation of U.S. application Ser. No. 15/858,963, filed Dec. 29, 2017, now U.S. Pat. No. 10,537,637, which claims priority to U.S. Provisional Patent Application Ser. No. 62/442,642, filed Jan. 5, 2017. The entirety of the aforementioned application is incorporated herein by reference.

FIELD

The present application relates generally to cancer treatment and, in particular, to checkpoint regulator antagonists, including anti-T cell Ig and ITIM domain (TIGIT) inhibitors, PD-1 inhibitors, PD-L1 inhibitors capable of modulating pathways associated with antitumor immunity, including bispecific and trispecific checkpoint regulator antagonists thereof.

BACKGROUND

The inability of the host to eliminate cancer cells remains a major problem. Although an increasing number of therapeutic monoclonal antibodies have been approved for treatment of various cancers, emergence of resistance to these antibodies is frequently observed, given the many different molecular pathways underlying cancer growth and progression to metastasis. Although the immune system is the principal mechanism of cancer prevention, cancer cells counteract immunosurveillance. Natural control mechanisms have been identified that limit T-cell activation so as to prevent collateral damage resulting from unrestrained T-cell activity. This process has been exploited by tumor cells to evade immune responses. Restoring the capacity of immune effector cells, especially T cells, to recognize and eliminate cancer is a major objective in immunotherapy.

The T cell Ig and ITIM domain (TIGIT) protein is an immune regulator that can block T cell immunity against cancer cells. TIGIT antagonists and other immune checkpoint antagonists interfere with (or inhibit) the activity of an immune checkpoint regulator so that, as a result of the binding to the checkpoint regulator or its ligand, signaling through the checkpoint regulator receptor is blocked or inhibited. In addition to TIGIT, other immune checkpoint regulators include the TIGIT ligands, CD112, CD155, PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; CD122 and its CD122R ligand; B7H3, B and T lymphocyte attenuator (BTLA), and VISTA.

The need exists for improved therapeutic binding antagonists or antibodies and methods of treating cancer and chronic viral infections with such reagents. Medicines for use in such improved methods of treatment may comprise antibodies or antibody fragments that specifically bind to TIGIT, PD-1 and/or PD-L1 and reverse or partially reverse the TIGIT-, PD-1 and/or PD-L1 mediated suppression of anti-tumor or anti-viral immune responses.

In view of the limitations in the ability of a host to eliminate cancer cells, a need exists for more effective compositions and methods for cancer treatment.

SUMMARY

One aspect of the present application relates to an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80%, 85%, 90%, 95%, 96%, 97%, 98%, 99% to about 100% homologous to an amino acid sequence selected from the group consisting of SEQ ID NOS: 1, 6, 11, 15, 17, 20 and 23, wherein HCDR2 has an amino acid sequence that is about 80%, 85%, 90%, 95%, 96%, 97%, 98%, 99% to about 100% homologous to an amino acid sequence selected from the group consisting of SEQ ID NOS: 2, 4, 7, 9, 12, 13, 16, 18, 21 and 24, and wherein HCDR3 has an amino acid sequence that is about 80%, 85%, 90%, 95%, 96%, 97%, 98%, 99% to about 100% homologous to an amino acid sequence selected from the group consisting of SEQ ID NOS: 3, 5, 8, 10, 14, 19, 22 and 25; and (2) a light chain variable region, wherein the light chain variable region comprises three complementarity determining regions (LCDRs): LCDR1, LCDR2 and LCDR3, wherein LCDR1 has an amino acid sequence that is about 80%, 85%, 90%, 95%, 96%, 97%, 98%, 99% to about 100% homologous to an amino acid sequence selected from the group consisting of SEQ ID NOS: 26, 29, 31, 33, 35, 39, 42 and 45, wherein LCDR2 has an amino acid sequence that is about 80%, 85%, 90%, 95%, 96%, 97%, 98%, 99% to about 100% homologous to an amino acid sequence selected from the group consisting of SEQ ID NOS: 27, 30, 36, 37, 40, 43 and 46, and wherein LCDR3 has an amino acid sequence that is about 80%, 85%, 90%, 95%, 96%, 97%, 98%, 99% to about 100% homologous to an amino acid sequence selected from the group consisting of SEQ ID NOS: 28, 32, 34, 38, 41, 44 and 47, wherein the antibody, or the antigen-binding portion thereof, binds specifically to human TIGIT.

In some embodiments, the antibody, or the antigen-binding portion thereof, comprises: (1) a heavy chain variable region having an amino acid sequence that is about 80%, 85%, 90%, 95%, 96%, 97%, 98%, 99% to about 100% homologous to an amino acid sequence selected from the group consisting of SEQ ID NOS: 107, 109, 111, 113, 115, 117, 119, 121, 123 and 125; and (2) a light chain variable region having an amino acid sequence that is about 80%, 85%, 90%, 95%, 96%, 97%, 98%, 99% to about 100% homologous to an amino acid sequence selected from the group consisting of SEQ ID NOS: 108, 110, 112, 114, 116, 118, 120, 122, 124 and 126, wherein the antibody, or the antigen-binding portion thereof, binds specifically to human TIGIT.

Another aspect of the present application relates to an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80%, 85%, 90%, 95%, 96%, 97%, 98%, 99% to about 100% homologous to an amino acid sequence selected from the group consisting of SEQ ID NOS: 48, 51, 54, 56 and 59, wherein HCDR2 has an amino acid sequence that is about 80%, 85%, 90%, 95%, 96%, 97%, 98%, 99% to about 100% homologous to an amino acid sequence selected from the group consisting of SEQ ID NOS: 49, 52, 57 and 60, and wherein HCDR3 has an amino acid sequence that is about 80%, 85%, 90%, 95%, 96%, 97%, 98%, 99% to about 100% homologous to an amino acid sequence selected from the group consisting of SEQ ID NOS: 50, 53, 55, 58 and 61; and (2) a light chain variable region, wherein the light chain variable region comprises three complementarity determining regions (LCDRs): LCDR1, LCDR2 and LCDR3, wherein LCDR1 has an amino acid sequence that is about 80%, 85%, 90%, 95%, 96%, 97%, 98%, 99% to about 100% homologous to an amino acid sequence selected from the group consisting of SEQ ID NOS: 62, 65, 68, 69, 70 and 73, wherein LCDR2 has an amino acid sequence that is about 80%, 85%, 90%, 95%, 96%, 97%, 98%, 99% to about 100% homologous to an amino acid sequence selected from the group consisting of SEQ ID NOS: 63, 66, 71 and 74, and wherein LCDR3 has an amino acid sequence that is about 80%, 85%, 90%, 95%, 96%, 97%, 98%, 99% to about 100% homologous to an amino acid sequence selected from the group consisting of SEQ ID NOS: 64, 67, 72 and 75, wherein the antibody, or the antigen-binding portion thereof, binds specifically to human PD-1.

In some embodiments, the antibody, or the antigen-binding portion thereof, comprises: (1) a heavy chain variable region having an amino acid sequence that is about 80%, 85%, 90%, 95%, 96%, 97%, 98%, 99% to about 100% homologous to an amino acid sequence selected from the group consisting of SEQ ID NOS: 127, 129, 131, 133, 135 and 137; and (2) a light chain variable region having an amino acid sequence that is about 80%, 85%, 90%, 95%, 96%, 97%, 98%, 99% to about 100% homologous to an amino acid sequence selected from the group consisting of SEQ ID NOS: 128, 130, 132, 134, 136 and 138, wherein the antibody, or the antigen-binding portion thereof, binds specifically to human PD-1.

Another aspect of the present application relates to an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80%, 85%, 90%, 95%, 96%, 97%, 98%, 99% to about 100% homologous to an amino acid sequence selected from the group consisting of SEQ ID NOS: 76, 79, 85 and 88, wherein HCDR2 has an amino acid sequence that is about 80%, 85%, 90%, 95%, 96%, 97%, 98%, 99% to about 100% homologous to an amino acid sequence selected from the group consisting of SEQ ID NOS: 77, 80, 82, 84, 86 and 89, and wherein HCDR3 has an amino acid sequence that is about 80%, 85%, 90%, 95%, 96%, 97%, 98%, 99% to about 100% homologous to an amino acid sequence selected from the group consisting of SEQ ID NOS: 78, 81, 83, 87 and 90; and (2) a light chain variable region, wherein the light chain variable region comprises three complementarity determining regions (LCDRs): LCDR1, LCDR2 and LCDR3, wherein LCDR1 has an amino acid sequence that is about 80%, 85%, 90%, 95%, 96%, 97%, 98%, 99% to about 100% homologous to an amino acid sequence selected from the group consisting of SEQ ID NOS: 91, 94, 98, 101 and 104, wherein LCDR2 has an amino acid sequence that is about 80%, 85%, 90%, 95%, 96%, 97%, 98%, 99% to about 100% homologous to an amino acid sequence selected from the group consisting of SEQ ID NOS: 92, 95, 99, 102 and 105, and wherein LCDR3 has an amino acid sequence that is about 80%, 85%, 90%, 95%, 96%, 97%, 98%, 99% to about 100% homologous to an amino acid sequence selected from the group consisting of SEQ ID NOS: 93, 96, 97, 100, 103 and 106, wherein the antibody, or the antigen-binding portion thereof, binds specifically to human PD-L1.

In some embodiments, the antibody, or the antigen-binding portion thereof, comprises: (1) a heavy chain variable region having an amino acid sequence that is about 80%, 85%, 90%, 95%, 96%, 97%, 98%, 99% to about 100% homologous to an amino acid sequence selected from the group consisting of SEQ ID NOS: 139, 141, 143, 145, 147, 149, 151 and 153; and (2) a light chain variable region having an amino acid sequence that is about 80%, 85%, 90%, 95%, 96%, 97%, 98%, 99% to about 100% homologous to an amino acid sequence selected from the group consisting of SEQ ID NOS: 140, 142, 144, 146, 148, 150, 152 and 154, wherein the antibody, or the antigen-binding portion thereof, binds specifically to human PD-L1.

Another aspect of the present application relates to a bispecific antibody, comprising: a first antigen binding domain comprising the antigen-binding portion of the anti-TIGIT, anti-PD-1 and/or anti-PD-L1 antibody of the present application; and a second antigen binding domain comprising the antigen-binding portion of another anti-TIGIT, anti-PD-1 antibody and/or anti-PD-L1 antibody of the present application.

In one embodiment, a bispecific checkpoint regulator antagonist, TP-M2T8P5 comprises: (1) a heavy chain variable region having an amino acid sequence that is about 80%, 85%, 90%, 95%, 96%, 97%, 98%, 99% to about 100% homologous to the amino acid sequence in SEQ ID NO: 155; and (2) a variable light chain variable region having an amino acid sequence that is about 80%, 85%, 90%, 95%, 96%, 97%, 98%, 99% to about 100% homologous to the amino acid sequence in SEQ ID NO: 156.

In another embodiment, a bispecific checkpoint regulator antagonist, TP-M4T8P5 comprises: (1) a light chain variable region 2/heavy chain variable region1 (VL2/VH1) having an amino acid sequence that is about 80%, 85%, 90%, 95%, 96%, 97%, 98%, 99% to about 100% homologous to the amino acid sequence in SEQ ID NO: 157; and (2) a heavy chain variable 2 region/light chain variable region 1 (VH2/VL1) having an amino acid sequence that is about 80%, 85%, 90%, 95%, 96%, 97%, 98%, 99% to about 100% homologous to the amino acid sequence in SEQ ID NO: 158.

In another embodiment, a bispecific checkpoint regulator antagonist, TP-M6T8P5 comprises: (1) a heavy chain variable region having an amino acid sequence that is about 80%, 85%, 90%, 95%, 96%, 97%, 98%, 99% to about 100% homologous to the amino acid sequence in SEQ ID NO: 159; (2) a light chain variable region 2/light chain constant region (VL2/CL) having an amino acid sequence that is about 80%, 85%, 90%, 95%, 96%, 97%, 98%, 99% to about 100% homologous to the amino acid sequence in SEQ ID NO: 160; and (3) a heavy chain variable region 1/heavy chain constant region 1 (VH1/CH1) having an amino acid sequence that is about 80%, 85%, 90%, 95%, 96%, 97%, 98%, 99% to about 100% homologous to the amino acid sequence in SEQ ID NO: 161.

In another embodiment, a bispecific checkpoint regulator antagonist, TP-M6T8L8 comprises: (1) a heavy chain variable region having an amino acid sequence that is about 80%, 85%, 90%, 95%, 96%, 97%, 98%, 99% to about 100% homologous to the amino acid sequence in SEQ ID NO: 162; (2) a light chain variable region 2/light chain constant region (VL2/CL) having an amino acid sequence that is about 80%, 85%, 90%, 95%, 96%, 97%, 98%, 99% to about 100% homologous to the amino acid sequence in SEQ ID NO: 163; and (3) a heavy chain variable region 1/heavy chain constant region 1 (VH1/CH1) having an amino acid sequence that is about 80%, 85%, 90%, 95%, 96%, 97%, 98%, 99% to about 100% homologous to the amino acid sequence in SEQ ID NO: 164.

In another embodiment, a bispecific checkpoint regulator antagonist, TP-M8T10P1 (TP-83) comprises: (1) a heavy chain variable region having an amino acid sequence that is about 80%, 85%, 90%, 95%, 96%, 97%, 98%, 99% to about 100% homologous to the amino acid sequence in SEQ ID NO: 165; and (2) a light chain having an amino acid sequence that is about 80%, 85%, 90%, 95%, 96%, 97%, 98%, 99% to about 100% homologous to the amino acid sequence in SEQ ID NO: 166.

In another embodiment, a bispecific checkpoint regulator antagonist, TP-M9T10P1 (TP-93) comprises: (1) a heavy chain that is about 80%, 85%, 90%, 95%, 96%, 97%, 98%, 99% to about 100% homologous to the amino acid sequence in SEQ ID NO: 167; and (2) a light chain having an amino acid sequence that is about 80%, 85%, 90%, 95%, 96%, 97%, 98%, 99% to about 100% homologous to the amino acid sequence in SEQ ID NO: 168.

In another embodiment, a bispecific checkpoint regulator antagonist, TP-M9T10P5 comprises: (1) a heavy chain that is about 80%, 85%, 90%, 95%, 96%, 97%, 98%, 99% to about 100% homologous to the amino acid sequence in SEQ ID NO: 169; and (2) a light chain having an amino acid sequence that is about 80%, 85%, 90%, 95%, 96%, 97%, 98%, 99% to about 100% homologous to the amino acid sequence in SEQ ID NO: 170.

In another embodiment, a bispecific checkpoint regulator antagonist, TP-M10T8P5 (TP-92) comprises: (1) a heavy chain that is about 80%, 85%, 90%, 95%, 96%, 97%, 98%, 99% to about 100% homologous to the amino acid sequence in SEQ ID NO: 171; and (2) a light chain variable region having an amino acid sequence that is about 80%, 85%, 90%, 95%, 96%, 97%, 98%, 99% to about 100% homologous to the amino acid sequence in SEQ ID NO: 172.

In another embodiment, a bispecific checkpoint regulator antagonist, TP-M10T8L8 comprises an amino acid sequence that is about 80%, 85%, 90%, 95%, 96%, 97%, 98%, 99% to about 100% homologous to the amino acid sequence in SEQ ID NO: 173.

In another embodiment, a bispecific checkpoint regulator antagonist, TP-M14T8P5 comprises: (1) a heavy chain variable region 2/heavy chain constant region 1 (VH2/CH1) having an amino acid sequence that is about 80%, 85%, 90%, 95%, 96%, 97%, 98%, 99% to about 100% homologous to the amino acid sequence in SEQ ID NO: 174; (2) a variable light chain region 1/heavy chain constant region 1 (VL1/CH1) having an amino acid sequence that is about 80%, 85%, 90%, 95%, 96%, 97%, 98%, 99% to about 100% homologous to the amino acid sequence in SEQ ID NO: 175; (3) a light chain variable region 2/light chain constant region (VL2/CL) having an amino acid sequence that is about 80%, 85%, 90%, 95%, 96%, 97%, 98%, 99% to about 100% homologous to the amino acid sequence in SEQ ID NO: 176; and (4) a heavy chain variable region 1/light chain constant region (VH1/CL) having an amino acid sequence that is about 80%, 85%, 90%, 95%, 96%, 97%, 98%, 99% to about 100% homologous to the amino acid sequence in SEQ ID NO: 177.

In another embodiment, a bispecific checkpoint regulator antagonist, TP-M14T8L8 comprises: (1) a heavy chain variable region 2/heavy chain constant region 1 (VH2/CH1) having an amino acid sequence that is about 80%, 85%, 90%, 95%, 96%, 97%, 98%, 99% to about 100% homologous to the amino acid sequence in SEQ ID NO: 178; (2) a variable light chain region 1/heavy chain constant region 2 (VL1/HC2) having an amino acid sequence that is about 80%, 85%, 90%, 95%, 96%, 97%, 98%, 99% to about 100% homologous to the amino acid sequence in SEQ ID NO: 179; (3) a light chain variable region 2/light chain constant region (VL2/CL) having an amino acid sequence that is about 80%, 85%, 90%, 95%, 96%, 97%, 98%, 99% to about 100% homologous to the amino acid sequence in SEQ ID NO: 180; and (4) a heavy chain variable region 1/light chain constant region (VH1/CL) having an amino acid sequence that is about 80%, 85%, 90%, 95%, 96%, 97%, 98%, 99% to about 100% homologous to the amino acid sequence in SEQ ID NO: 181.

Another aspect of the present application relates to nucleic acids encoding the antibody, the antigen-binding fragment thereof, or the bispecific antibody of the present application.

Another aspect of the present application relates to expression vectors comprising the nucleic acids of the present application.

Another aspect of the present application relates to host cells transformed with the expression vectors of the present application.

Another aspect of the present application relates to a method of producing the anti-TIGIT antibody, anti-PD-1 antibody, anti-PD-L1 antibody, antigen-binding fragment thereof, including monospecific, bispecific and trispecific checkpoint regulator anatagonists, and combinations thereof.

Another aspect of the present application relates to a method of reducing or depleting regulatory T cells in a tumor of a subject in need thereof, comprising: administering to the subject an effective amount the antibody, antibody fragment or bispecific checkpoint regulator antagonist of the present application.

BRIEF DESCRIPTION OF THE DRAWINGS

FIGS. 3A-C shows CDR sequences of anti-TIGIT mouse mabs (FIG. 3A); anti-PD-1 mouse mabs (FIG. 3B); and anti-PD-L1 mouse mabs (FIG. 3C).

FIGS. 4A-H shows several embodiments of anti-TIGIT antibody variable domain sequences (FIGS. 4A-C); anti-PD-1 antibody variable domain sequences (FIGS. 4D-E); and anti-PD-L1 antibody variable domain sequences (FIGS. 4F-H).

FIGS. 5A-G depicts exemplary bispecific checkpoint regulator antagonist sequences against PD1 and TIGIT.

FIGS. 17A-17N show a variety of different bispecific checkpoint regulator antagonists, M1-M14, where: (1) the VH1 and VL1 regions correspond to anti-PD1, anti-PD-L1 or any other mab variable domain; and (2) the VH2 and VL2 regions correspond to anti-TIGIT variable domains.

FIGS. 18A-18J show a variety of different trispecific checkpoint regulator antagonists, where: (1) the VH1 and VL1 regions correspond to anti-TIGIT variable domains; (2) the VH2 and VL21 regions correspond to anti-PD1, anti-PD-L1 or any other mab variable domain; and (3) the circular region corresponds to AMG386 or any other biological peptide.

DETAILED DESCRIPTION

Figure 1:
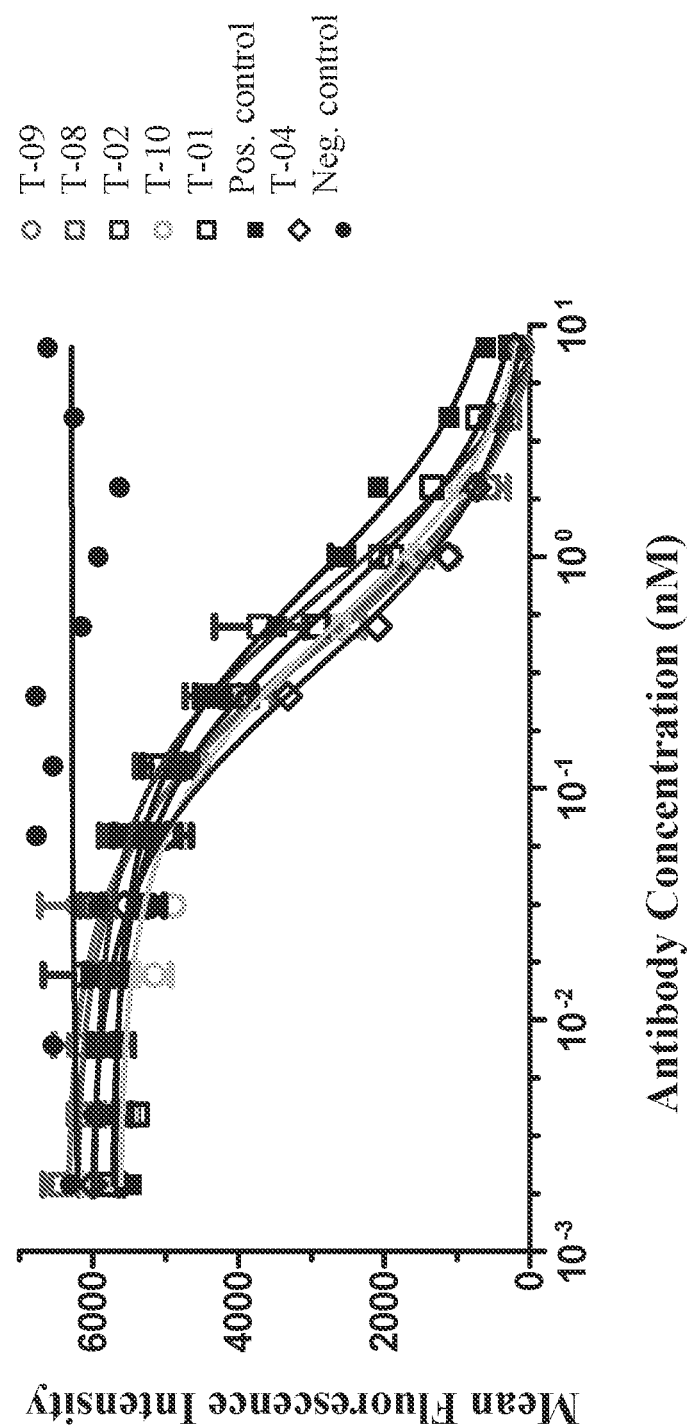
FIG. 1 shows the result of anti-TIGIT mabs competing TIGIT and PVR (CD155), the TIGIT ligand.
Figure 2:
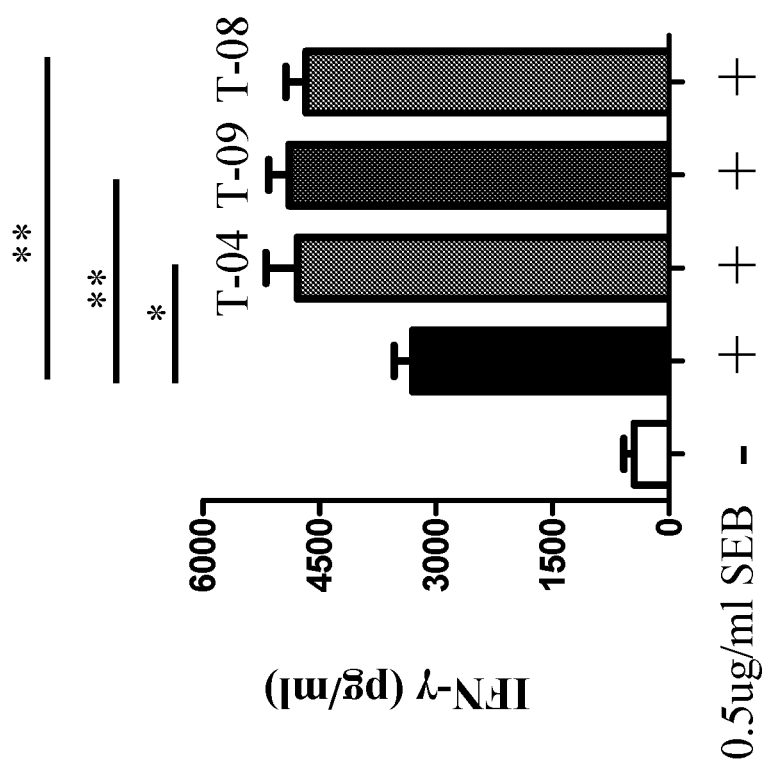
FIG. 2 shows that anti-TIGIT mouse mabs enhance human T cell function.

Herein incorporated by reference is the sequence listing filed with the USPTO as 2022-002 CONT-CONT.xml which was created on May 16, 2023, and the size is 256,624 bytes.

Definitions

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides. With respect to the teachings in the present application, any issued patent or patent application publication described in this application is expressly incorporated by reference herein.

As used herein, the term "TIGIT" refers to any form of TIGIT and variants thereof that retain at least part of the activity of TIGIT. Unless indicated differently, such as by specific reference to human TIGIT, TIGIT includes all mammalian species of native sequence TIGIT, e.g., human, canine, feline, equine, and bovine. The following is an exemplary human TIGIT amino acid sequence:

(SEQ ID. NO. 182)
MTGTIETTGNISAEKGGSIILQCHLSSTTAQVTQVNWEQQDQLLAICNAD

LGWHISPSFKDRVAPGPGLGLTLQSLTVNDTGEYFCIYHTYPDGTYTGRI

FLEVLESSVAEHGARFQIPLLGAMAATLVVICTAVIVVVALTRKKKALRI

HSVEGDLRRKSAGQEEWSPSAPSPPGSCVQAEAAPAGLCGEQRGEDCAEL

HDYFNVLSYRSLGNCSFFTETG

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine. An exemplary human PD-1 amino acid sequences is listed below:

(SEQ ID NO: 183)
LDSPDRWNPPTFSPALLVVTEGDNATFTSCFSNTSESFVLNWYRMSPSNQ

TDKLAAFPEDRSQPGQDCRFRVTQLPNGRDFHMSVVRARRNDSGTYLCGA

ISLAPKAQIKESLRAELRVTERRAEVPTAHPSPSPRPAGQFQTLVVGVVG

GLLGSLVLLVWVLAVICSRAARGTIGARRTGQPLKEDPSAVPVFSVDYGE

LDFQWREKTPEPPVPCVPEQTEYATIVFPSGMGTSSPARRGSADGPRSAQ

PLRPEDGHCSWPL

As used herein, the term "PD-L1" refers to any form of PD-L1 and variants thereof that retain at least part of the activity of PD-L1. Unless indicated differently, such as by specific reference to human PD-L1, PD-L1 includes all mammalian species of native sequence PD-L1, e.g., human, canine, feline, equine, and bovine. Exemplary human PD-L1 amino acid sequences is listed below:

(SEQ ID NO: 184)
FTVTVPKDLYVVEYGSNMTIECKFPVEKQLDLAALIVYWEMEDKNIIQFV

HGEEDLKVQHSSYRQRARLLKDQLSLGNAALQITDVKLQDAGVYRCMISY

GGADYKRITVKVNAPYNKINQRILVVDPVTSEHELTCQAEGYPKAEVIWT

SSDHQVLSGKTTTTNSKREEKLFNVTSTLRINTTTNEIFYCTFRRLDPEE

NHTAELVIPELPLAHPPNER

The term "agonist" refers to a substance which promotes (i.e., induces, causes, enhances, or increases) the biological activity or effect of another molecule. The term agonist encompasses substances which bind receptor, such as an antibody, and substances which promote receptor function without binding thereto (e.g., by activating an associated protein).

The term "antagonist" or "inhibitor" refers to a substance that prevents, blocks, inhibits, neutralizes, or reduces a biological activity or effect of another molecule, such as a receptor.

As used herein, the term "antibody" refers to a polypeptide or a polypeptide complex that specifically recognizes and binds to an antigen through one or more immunoglobulin variable regions. An antibody can be a whole antibody, an antigen binding fragment or a single chain thereof. The term "antibody" encompasses various broad classes of polypeptides that can be distinguished biochemically. Those skilled in the art will appreciate that heavy chains are classified as alpha, delta, epsilon, gamma, and mu, or α, δ, ε, γ and μ) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgG5, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are within the scope of the present disclosure, the following discussion will generally be directed to the IgG class of immunoglobulin molecules.

Antibodies of the disclosure include, but are not limited to, polyclonal, monoclonal, multispecific, bispecific, trispecific, human, humanized, primatized, chimeric and single chain antibodies. Antibodies disclosed herein may be from any animal origin, including birds and mammals. Preferably, the antibodies are human, murine, donkey, rabbit, goat, guinea pig, camel, llama, horse, or chicken antibodies. In some embodiments, the variable region may be condricthoid in origin (e.g., from sharks).

The terms "antibody fragment" or "antigen-binding fragment" are used with reference to a portion of an antibody, such as $F(ab')_2$, $F(ab)_2$, Fab', Fab, Fv, single-chain Fvs (scFv), single-chain antibodies, disulfide-linked Fvs (sdFv), fragments comprising either a VL or VH domain, fragments produced by a Fab expression library and anti-idiotypic (anti-Id) antibodies. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered proteins comprising immunoglobulin variable regions that act like an antibody by binding to a specific antigen to form a complex.

A "single-chain fragment variable" or "scFv" refers to a fusion protein of the variable regions of the heavy (VH) and light chains (VL) of immunoglobulins. In some aspects, the regions are connected with a short linker peptide of ten to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker.

With regard to IgGs, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration where the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules are derived from camelid species or engineered based on camelid immunoglobulins. Alternatively, an immunoglobulin molecule may consist of heavy chains only, with no light chains or light chains only, with no heavy chains.

In naturally occurring antibodies, the six CDRs present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a .beta.-sheet conformation and the CDRs form loops which connect, and in some cases form part of, the .beta.-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined.

As used herein, the terms "VH1" and "VH2" refer to immunoglobulin heavy chain variable domains corresponding to two different binding specificities. Likewise, the terms "VL1" and "VL2" refer to light chain variable domains corresponding to two different binding specificities. When used together, it is to be understood that VH1 and VL1 regions define a common binding specificity and that VH2 and VL2 domains define a second binding specificity Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

As used herein, the term "light chain constant region" includes amino acid sequences derived from antibody light chain. Preferably, the light chain constant region comprises at least one of a constant kappa domain or constant lambda domain.

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

A "light chain-heavy chain pair" refers to the collection of a light chain and heavy chain that can form a dimer through a disulfide bond between the CL domain of the light chain and the CH1 domain of the heavy chain.

The subunit structures and three dimensional configurations of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

As used herein the term "disulfide bond" includes a covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, a "variant" of an antibody, an antibody fragment or an antibody domain refers to an antibody, an antibody fragment or an antibody domain that (1) shares a sequence homology of at least 80%, 85%, 90%, 95%, 96%, 97%, 98% or 99% with the original antibody, antibody fragment or antibody domain, and (2) binds specifically to the same target that the original antibody, antibody fragment or antibody domain binds specifically.

It should be understood that where a sequence homology range is presented herein, as in e.g., the phrase "about 80% to about 100%", such an embodiment includes any and all subranges within, wherein the lower number can be any whole number between 80 and 100.

As used herein, the phrase "humanized antibody" refers to an antibody derived from a non-human antibody, typically a mouse monoclonal antibody. Alternatively, a humanized antibody may be derived from a chimeric antibody that retains or substantially retains the antigen binding properties of the parental, non-human, antibody but which exhibits diminished immunogenicity as compared to the parental antibody when administered to humans.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

Included within the scope of the multispecific antibodies of the present application are various compositions and methodologies, including asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb$^2$ (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec, TvAb, Roche); scFv/Fc fusions; SCORPION (Emergent BioSolutions/Trubion, ZymoGenetics/BMS); dual affinity retargeting technology (Fc-DART), MacroGenics; dual (scFv)$_2$-Fabs (National Research Center for Antibody Medicine); F(ab)$_2$ fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack);

COMBODIES (Epigen Biotech); and IgG/non-IgG fusions (e.g., immunocytokines (EMDSerono, Philogen, ImmunGene, ImmunoMedics).

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." In some embodiments, an antibody or an antibody fragment "has specificity to" an antigen if the antibody or antibody fragment forms a complex with the antigen with a dissociation constant ($K_d$) of $10^{-6}$M or less, $10^{-7}$M or less, $10^{-8}$M or less, $10^{-9}$M or less, or $10^{-10}$M or less.

As used herein, the phrase "chimeric antibody," refers to an antibody where the immunoreactive region or site is obtained or derived from a first species and the constant region (which may be intact, partial or modified in accordance with the instant disclosure) is obtained from a second species. In certain embodiments the target binding region or site will be from a non-human source (e.g., mouse or primate) and the constant region is human.

The term "antagonist antibody" refers to an antibody that binds to a target and prevents or reduces the biological effect of that target. In some embodiments, the term can denote an antibody that prevents the target, e.g., TIGIT, to which it is bound from performing a biological function.

As used herein, an "anti-PD-1 antagonist antibody" refers to an antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including downstream events mediated by PD-1, such as PD-1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, an anti-PD-1 antagonist antibody binds PD-1 and upregulates an anti-tumor immune response.

As used herein, an "anti-PD-L1 antagonist antibody" refers to an antibody that is able to inhibit PD-L1 biological activity and/or downstream events(s) mediated by PD-L1. Anti-PD-L1 antagonist antibodies encompass antibodies that block, antagonize, suppress or reduce (to any degree including significantly) PD-L1 biological activity, including downstream events mediated by PD-L1, such as PD-L1 binding and downstream signaling, inhibition of T cell proliferation, inhibition of T cell activation, inhibition of IFN secretion, inhibition of IL-2 secretion, inhibition of TNF secretion, induction of IL-10, and inhibition of anti-tumor immune responses. For purposes of the present invention, it will be explicitly understood that the term "anti-PD-L1 antagonist antibody" (interchangeably termed "antagonist PD-L1 antibody", "antagonist anti-PD-L1 antibody" or "PD-L1 antagonist antibody") encompasses all the previously identified terms, titles, and functional states and characteristics whereby PD-L1 itself, a PD-L1 biological activity, or the consequences of the biological activity, are substantially nullified, decreased, or neutralized in any meaningful degree. In some embodiments, an anti-PD-L1 antagonist antibody binds PD-L1 and upregulates an anti-tumor immune response. The phrase "immune checkpoint regulator" refers to a functional class of agents, which inhibit or stimulate signaling through an immune checkpoint. An "immune checkpoint regulator" includes receptors and their associated ligands, which together provide a means for inhibiting or stimulating signaling pathways that otherwise lead to T-cell activation.

The phrases "immune checkpoint binding antagonist" and "immune checkpoint antagonist" are used interchangeably herein with reference to a class of agents that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Exemplary immune checkpoint antagonists include, but are not limited to TIGIT and its CD155 ligand, PVR; PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA. Immune checkpoint regulator antagonists include antibody fragments, peptide inhibitors, dominant negative peptides and small molecule drugs, either in isolated forms or as part of a fusion protein or conjugate.

The phrases "immune checkpoint binding agonist" and "immune checkpoint agonist" are used interchangeably herein with reference to a class of agents that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. Exemplary immune checkpoint regulator agonists include, but are not limited to members of the tumor necrosis factor (TNF) receptor superfamily, such as CD27, CD40, OX40 (CD134), glucocorticoid-induced TNFR family-related protein (GITR), and 4-1BB (CD137) and their ligands. Additional checkpoint regulator agonists belong to the B7-CD28 superfamily, including CD28 and ICOS.

The phrases "dominant-negative protein" or "dominant-negative peptide" refer to a protein or peptide derived from a wild type protein that has been genetically modified by mutation and/or deletion so that the modified protein or peptide interferes with the function of the endogenous wild-type protein from which it is derived.

The phrase "VEGF binding antagonist" refers to a functional class of agents that bind to VEGF-A or its receptor, VEGFR-2, so that, as a result of the binding, activation of VEGFR-2 by VEGF-A is blocked or inhibited. As used herein, the term "VEGF binding antagonists" include antibody fragments, peptide inhibitors, dominant negative peptides and small molecule drugs, either in isolated forms or as part of a fusion protein or conjugate.

The phrase "Tie2 tyrosine kinase receptor binding antagonist" refers to a functional class of agents that bind to a Tie2 tyrosine kinase receptor or one of its ligands so that, as a result of the binding, activation of the Tie2 tyrosine kinase receptor by one or more of its ligands (i.e., Ang1, Ang2, Ang3 and Ang4) is blocked or inhibited. As used herein, the term "Tie2 tyrosine kinase receptor binding antagonist" include antibody fragments, peptide inhibitors, dominant negative peptides and small molecule drugs, either in isolated forms or as part of a fusion protein or conjugate.

The phrase "small molecule drug" refers to a molecular entity, often organic or organometallic, that is not a polymer, that has medicinal activity, and that has a molecular weight less than about 2 kDa, less than about 1 kDa, less than about 900 Da, less than about 800 Da or less than about 700 Da. The term encompasses most medicinal compounds termed "drugs" other than protein or nucleic acids, although a small peptide or nucleic acid analog can be considered a small molecule drug. Examples include chemotherapeutic anticancer drugs and enzymatic inhibitors. Small molecules drugs can be derived synthetically, semi-synthetically (i.e., from naturally occurring precursors), or biologically.

As used herein, the term "recombinant" refers to polypeptides or polynucleotides that do not exist naturally and which may be created by combining polynucleotides or polypeptides in arrangements that would not normally occur together. The checkpoint regulator antagonists described herein are by definition "recombinant."

When describing polypeptide domain arrangements with hyphens between individual domains (e.g., CH2-CH3), it should be understood that the order of the listed domains is from the amino terminal end to the carboxy terminal end.

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

The term "immunoconjugate" refers to an antibody which is fused by covalent linkage to an inhibitory peptide or small molecule drug. The peptide or small molecule drug can be linked to the C-terminus of a constant heavy chain or to the N-terminus of a variable light and/or heavy chain.

A "linker" may be used to link the peptide or small molecule drug, such as a maytansinoid, to the checkpoint regulator antagonists in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art. The immunoconjugate may further include a flexible 3-15 amino acid peptide (or spacer) between a checkpoint regulator antagonist and the peptide and/or small molecule drug.

As used herein, the phrase "multispecific inhibitor" refers to a molecule comprising at least two targeting domains with different binding specificities. In some embodiments, the multispecific inhibitor is an polypeptide comprising a scaffold and two or more immunoglobulin antigen binding domains targeting different antigens or epitopes. In certain embodiments, the multispecific inhibitor is a bispecific antibody. In certain embodiments, the multispecific inhibitor is a trispecific antibody.

As used herein, the phrase "bispecific checkpoint regulator antagonist" refers to a molecule comprising at least two targeting domains with different binding specificities. Each targeting domain is capable of binding specifically to a target molecule and inhibiting a biological function of the target molecule upon binding to the target molecule. In some embodiments, the bispecific checkpoint regulator antagonist is a polymeric molecule having two or more peptides. In some embodiments, the targeting domain comprises an antigen binding domain or a CDR of an antibody. In some embodiments, the bispecific inhibitor is a bispecific antibody.

The terms "bispecific antibody" and "bispecific checkpoint regulator antagonist" are used interchangeably herein with reference to an antibody that can specifically bind two different antigens (or epitopes). In some embodiments, the bispecific antibody is a full-length antibody that binds one antigen (or epitope) on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences), and is monovalent for each antigen it binds to.

In other embodiments, the bispecific antibody is a full-length antibody that can bind two different antigens (or epitopes) in each of its two binding arms (two pairs of HC/LC) In these embodiments, the bispecific antibody has two identical antigen binding arms, with identical specificity and identical CDR sequences, and is bivalent for each antigen it binds to.

The terms "bispecific antibody" and "bispecific checkpoint regulator antagonist" are used interchangeably herein with reference to a molecule comprising three targeting domains with three different binding specificities. Each targeting domain is capable of binding specifically to a target molecule and inhibiting a biological function of the target molecule upon binding to the target molecule. In some embodiments, the trispecific checkpoint regulator antagonist is a polymeric molecule having two or more peptides. In some embodiments, the targeting domain comprises an antigen binding domain or a CDR of an antibody. In some embodiments, the trispecific checkpoint regulator antagonist is a trispecific antibody.

Exemplary bispecific and trispecific antibodies may include asymmetric IgG-like antibodies (e.g., triomab/quadroma, Trion Pharma/Fresenius Biotech); knobs-into-holes antibodies (Genentech); Cross MAbs (Roche); electrostatically matched antibodies (AMGEN); LUZ-Y (Genentech); strand exchange engineered domain (SEED) body (EMD Serono; biolonic, Merus); Fab-exchanged antibodies (Genmab), symmetric IgG-like antibodies (e.g. dual targeting (DT)-Ig (GSK/Domantis); two-in-one antibody (Genentech); crosslinked MAbs (Karmanos Cancer Center), mAb2 (F-star); Cov X-body (Cov X/Pfizer); dual variable domain (DVD)-Ig fusions (Abbott); IgG-like bispecific antibodies (Eli Lilly); Ts2Ab (Medimmune/AZ); BsAb (ZymoGenetics); HERCULES (Biogen Idec, TvAb, Roche); scFv/Fc fusions; SCORPION (Emergent BioSolutions/Trubion, ZymoGenetics/BMS); dual affinity retargeting technology (Fc-DART), MacroGenics; dual (scFv)$_2$-Fabs (National Research Center for Antibody Medicine); F(ab)$_2$ fusions (Medarex/AMGEN); dual-action or Bis-Fab (Genentech); Dock-and-Lock (DNL, ImmunoMedics); Fab-Fv (UCB-Celltech); scFv- and diabody-based antibodies (e.g., bispecific T cell engagers (BiTEs, Micromet); tandem diabodies (Tandab, Affimed); DARTs (MacroGenics); single-chain diabodies; TCR-like antibodies (AIT, Receptor Logics); human serum albumin scFv fusion (Merrimack); COMBODIES (Epigen Biotech); and IgG/non-IgG fusions (e.g., immunocytokines (EMDSerono, Philogen, ImmunGene, ImmunoMedics).

The terms "treat" and "treatment" refer to the amelioration of one or more symptoms associated with a cell proliferative disorder; prevention or delay of the onset of one or more symptoms of a cell proliferative disorder; and/or lessening of the severity or frequency of one or more symptoms of cell proliferative disorder.

The phrases "to a patient in need thereof", "to a patient in need of treatment" or "a subject in need of treatment" includes subjects, such as mammalian subjects, that would benefit from administration of the checkpoint regulator antagonist of the present disclosure for treatment of a cell proliferative disorder.

The terms "therapeutically effective amount", "pharmacologically effective amount", and "physiologically effective amount" are used interchangeably to mean the amount of a checkpoint regulator antagonist that is needed to provide a threshold level of active antagonist agents in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein or otherwise available in the relevant literature.

The terms, "improve", "increase" or "reduce", as used in this context, indicate values or parameters relative to a baseline measurement, such as a measurement in the same individual prior to initiation of the treatment described herein, or a measurement in a control individual (or multiple control individuals) in the absence of the treatment described herein.

A "control individual" is an individual afflicted with the same cell proliferative disorder as the individual being treated, who is about the same age as the individual being treated (to ensure that the stages of the disease in the treated individual and the control individual(s) are comparable). The individual (also referred to as "patient" or "subject") being treated may be a fetus, infant, child, adolescent, or adult human with a cell proliferative disorder.

The term "cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is a neoplasm, cancer or tumor.

The term "cancer" refers to any one of a variety of malignant neoplasms characterized by the proliferation of cells that have the capability to invade surrounding tissue and/or metastasize to new colonization sites, and includes leukemia, lymphoma, carcinoma, melanoma, sarcoma, germ cell tumor and blastoma. Exemplary cancers for treatment with the methods of the instant disclosure include cancer of the brain, bladder, breast, cervix, colon, head and neck, kidney, lung, non-small cell lung, mesothelioma, ovary, prostate, stomach and uterus, leukemia, and medulloblastoma.

The term "leukemia" refers to progressive, malignant diseases of the blood-forming organs and is generally characterized by a distorted proliferation and development of leukocytes and their precursors in the blood and bone marrow. Exemplary leukemias include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to the malignant growth of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, naspharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, and carcinoma *villosum*.

The term "sarcoma" refers to a tumor made up of a substance like the embryonic connective tissue and is generally composed of closely packed cells embedded in a fibrillar or homogeneous substance. Exemplary sarcomas include, for example, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphomas (e.g., Non-Hodgkin Lymphoma), immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

Checkpoint Regulator Antagonists

The present application provides checkpoint regulator antagonists that bind specifically to TIGIT, PD-1 and PD-L1 and inhibit one or more of their corresponding biological functions. In some embodiments, the checkpoint regulator antagonist is an anti-TIGIT antibody or antibody fragment. In some embodiments, the checkpoint regulator antagonist is an anti-PD-1 antibody or antibody fragment. In other embodiments, the checkpoint regulator antagonist is an anti-PD-L1 antibody or antibody fragment. In other embodiments, a bispecific or trispecific checkpoint regulator antagonist contains multiple specificities (anti-TIGIT, anti-PD-1 and/or anti-PD-L1) for binding several checkpoint regulators.

Anti-TIGIT Antibody and Anti-TIGIT Antibody Fragments

In some embodiments, the TIGIT inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% homologous to an amino acid sequence selected from the group consisting of SEQ ID NOS: 1, 6, 11, 15, 17, 20 and 23, wherein HCDR2 has an amino acid sequence that is about 80% to about 100% homologous to an amino acid sequence selected from the group consisting of SEQ ID NOS: 2, 4, 7, 9, 12, 13, 16, 18, 21 and 24, and wherein HCDR3 has an amino acid sequence that is about 80% to about 100% homologous to an amino acid sequence selected from the group consisting of SEQ ID NOS: 3, 5, 8, 10, 14, 19, 22 and 25; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% homologous to an amino acid sequence selected from the group consisting of SEQ ID NOS: 26, 29, 31, 33, 35, 39, 42 and 45, wherein LCDR2 has an amino acid sequence that is about 80% to about 100% homologous to an amino acid sequence selected from the group consisting of SEQ ID NOS: 27, 30, 36, 37, 40, 43 and 46, and wherein LCDR3 has an amino acid sequence that is about 80% to about 100% homologous to an amino acid sequence selected from the group consisting of SEQ ID NOS: 28, 32, 34, 38, 41, 44 and 47, wherein the antibody, or the antigen-binding portion thereof, binds specifically to human TIGIT.

In some embodiments, the TIGIT inhibitor of the present application is an antibody, or an antigen-binding portion thereof, comprising (1) a heavy chain variable region having an amino acid sequence that is about 80% to about 100% homologous to an amino acid sequence selected from the group consisting of SEQ ID NOS: 107, 109, 111, 113, 115, 117, 119, 121, 123 and 125; and (2) a light chain variable region having an amino acid sequence that is about 80% to about 100% homologous to an amino acid sequence selected from the group consisting of SEQ ID NOS: 108, 110, 112, 114, 116, 118, 120, 122, 124 and 126, wherein the antibody, or the antigen-binding portion thereof, binds specifically to human TIGIT.

Anti-PD-1 Antibody and Anti-PD-1 Antibody Fragments

In some embodiments, the PD-1 inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% homologous to an amino acid sequence selected from the group consisting of SEQ ID NOS: 48, 51, 54, 56 and 59, wherein HCDR2 has an amino acid sequence that is about 80% to about 100% homologous to an amino acid sequence selected from the group consisting of SEQ ID NOS: 49, 52, 57 and 60, and wherein HCDR3 has an amino acid sequence that is about 80% to about 100% homologous to an amino acid sequence selected from the group consisting of SEQ ID NOS: 50, 53, 55, 58 and 61; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% homologous to an amino acid sequence selected from the group consisting of SEQ ID NOS: 62, 65, 68, 69, 70 and 73, wherein LCDR2 has an amino acid sequence that is about 80% to about 100% homologous to an amino acid sequence selected from the group consisting of SEQ ID NOS: 63, 66, 71 and 74, and wherein LCDR3 has an amino acid sequence that is about 80% to about 100% homologous to an amino acid sequence selected from the group consisting of SEQ ID NOS: 64, 67, 72 and 75, wherein the antibody, or the antigen-binding portion thereof, binds specifically to human PD-1.

In some embodiments, the PD-1 inhibitor of the present application is an antibody, or an antigen-binding portion thereof, comprising: (1) a heavy chain variable region having an amino acid sequence that is about 80% to about 100% homologous to an amino acid sequence selected from the group consisting of SEQ ID NOS: 127, 129, 131, 133, 135 and 137; and (2) a light chain variable region having an amino acid sequence that is about 80% to about 100% homologous to an amino acid sequence selected from the group consisting of SEQ ID NOS: 128, 130, 132, 134, 136 and 138, wherein the antibody, or the antigen-binding portion thereof, binds specifically to human PD-1.

Anti-PD-L1 Antibody and Anti-PD-L1 Antibody Fragments

In some embodiments, the PD-L1 inhibitor of the present application is an antibody, or an antigen-binding portion thereof, comprising: (1) a heavy chain variable region, wherein the heavy chain variable region comprises three complementarity determining regions (HCDRs): HCDR1, HCDR2 and HCDR3, wherein HCDR1 has an amino acid sequence that is about 80% to about 100% homologous to an amino acid sequence selected from the group consisting of SEQ ID NOS: 76, 79, 85 and 88, wherein HCDR2 has an amino acid sequence that is about 80% to about 100% homologous to an amino acid sequence selected from the group consisting of SEQ ID NOS: 77, 80, 82, 84, 86 and 89, and wherein HCDR3 has an amino acid sequence that is about 80% to about 100% homologous to an amino acid sequence selected from the group consisting of SEQ ID NOS: 78, 81, 83, 87 and 90; and (2) a light chain variable region, wherein the light chain variable region comprises three complementarity determining regions (LCDRs): LCDR1, LCDR2 and LCDR3, wherein LCDR1 has an amino acid sequence that is about 80% to about 100% homologous to an amino acid sequence selected from the group consisting of SEQ ID NOS: 91, 94, 98, 101 and 104, wherein LCDR2 has an amino acid sequence that is about 80% to about 100% homologous to an amino acid sequence selected from the group consisting of SEQ ID NOS: 92, 95, 99, 102 and 105, and wherein LCDR3 has an amino acid sequence that is about 80% to about 100% homologous to an amino acid sequence selected from the group consisting of SEQ ID NOS: 93, 96, 97, 100 and 106, wherein the antibody, or the antigen-binding portion thereof, binds specifically to human PD-L1.

In some embodiments, the PD-L1 inhibitor of the present application is an antibody, or an antigen-binding portion thereof, comprising: (1) a heavy chain variable region having an amino acid sequence that is about 80% to about 100% homologous to an amino acid sequence selected from the group consisting of SEQ ID NOS: 139, 141, 143, 145, 147, 149, 151 and 153; and (2) a light chain variable region having an amino acid sequence that is about 80% to about 100% homologous to an amino acid sequence selected from the group consisting of SEQ ID NOS: 140, 142, 144, 146, 148, 150, 152 and 154, wherein the antibody, or the antigen-binding portion thereof, binds specifically to human PD-L1.

The anti-TIGIT, anti-PD-1 and/or anti-PD-L1 antibody can be a monoclonal antibody, chimeric antibody, humanized antibody, scFv or multi-specific antibody comprising additional binding specificities targeting other TIGIT, PD-1 and/or PD-L1 epitopes or other binding targets as further described below. FIG. 4 shows the amino acid sequences of the CDRs corresponding to anti-TIGIT, anti-PD-1 and anti-PD-L1 monoclonal antibodies according to the present application.

The HCVRs and LCVRs described herein may be linked to a naturally-occurring Fc region or a non-naturally occurring or mutated Fc region, e.g., an effectorless or mostly effectorless Fc (e.g., human IgG2 or IgG4) or, alternatively, an Fc with enhanced binding to one or more activating Fc receptors (FcγRI, FcγRIIa or FcγRIIIa) so as to enhance Treg depletion in the tumor environment.

Accordingly, in certain embodiments the anti-TIGIT, anti-PD-1 and/or anti-PD-L1 HCVRs and LCVRs described herein may be linked to an Fc comprising one or more modifications, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or it may be modified to alter its glycosylation, to alter one or more functional properties of the antibody. More specifically, in certain embodiments, the antibodies in the present application may include modifications in the Fc region in order to generate an Fc variant with (a) increased or decreased antibody-dependent cell-mediated cytotoxicity (ADCC), (b) increased or decreased complement mediated cytotoxicity (CDC), (c) increased or decreased affinity for C1q and/or (d) increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g., of the specific Fc region positions identified herein.

For uses where effector function is to be avoided altogether, e.g., when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g., N297A). Alternatively, a hybrid construct of human IgG2 (CH1 domain and hinge region) and human IgG4 (CH2 and CH3 domains) may be generated that is devoid of effector function, lacking the ability to bind FcγRs (like IgG2) and activate complement (like IgG4). When using an IgG4 constant domain, it is usually preferable to include the substitution S228P, which mimics the hinge sequence in IgG1 and thereby stabilizes IgG4 molecules, reducing Fab-arm exchange between the therapeutic antibody and endogenous IgG4 in the patient being treated.

In certain embodiments, the anti-TIGIT, anti-PD-1 or anti-PD-L1 antibody or fragment thereof may be modified to increase its biological half-life. Various approaches may be employed, including e.g., that increase the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022. The numbering of residues in the Fc region is that of the EU index of Kabat. Sequence variants disclosed herein are provided with reference to the residue number followed by the amino acid that is substituted in place of the naturally occurring amino acid, optionally preceded by the naturally occurring residue at that position. Where multiple amino acids may be present at a given position, e.g., if sequences differ between naturally occurring isotypes, or if multiple mutations may be substituted at the position, they are separated by slashes (e.g., "X/Y/Z").

Exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 31 IA, 312A, 378Q, 380A, 382A, 434A (Shields et al. (2001) J. Biol. Chem., 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) J. Immunol., 169:5171-5180, Dall'Acqua et al. (2006) J. Biol. Chem., 281:23514-23524, and U.S. Pat. No. 8,367,805.

Modification of certain conserved residues in IgG Fc (I253, H310, Q311, H433, N434), such as the N434A variant (Yeung et al. (2009) J. Immunol. 182:7663), have been proposed as a way to increase FcRn affinity, thus increasing the half-life of the antibody in circulation (WO 98/023289). The combination Fc variant comprising M428L and N434S has been shown to increase FcRn binding and increase serum half-life up to five-fold (Zalevsky et al. (2010) Nat. Biotechnol. 28:157). The combination Fc variant comprising T307A, E380A and N434A modifications also extends half-life of IgG1 antibodies (Petkova et al. (2006) Int. Immunol. 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life (U.S. 2006/173170). Further, a combination Fc variant comprising M252Y, S254T and T256E was reported to increase half-life-nearly 4-fold. Dall'Acqua et al. (2006) J. Biol. Chem. 281:23514.

Bispecific Checkpoint Regulator Antagonists

Another aspect of the present application relates to a bispecific checkpoint regulator antagonist, comprising: a first targeting domain that binds specifically to a checkpoint regulator and a second targeting domain that binds specifically to a second target. In some embodiments, the second target is selected from the group consisting of vascular endothelial growth factor (VEGF), vascular endothelial growth factor receptor (VEGFR), immune checkpoint regulators, Tie2 tyrosine kinase receptors and ligands of Tie2 tyrosine kinase receptors.

In some embodiments, the second target is also a checkpoint regulator.

In some embodiments, the first targeting domain comprises the antigen-binding portion of the anti-TIGIT, anti-PD-1 and/or anti-PD-L1 antibody of the present application. In some embodiments, the second targeting domain comprises the antigen-binding portion of another anti-TIGIT, anti-PD-1 antibody and/or anti-PD-L1 antibody of the present application. In some embodiments, the first targeting domain and the second targeting domain each comprises the antigen-binding portion of an anti-TIGIT, anti-PD-1 and/or anti-PD-L1 antibody of the present application, wherein the first targeting domain is different from the second targeting domain.

In some embodiments, the bispecific checkpoint regulator antagonist comprises a first targeting domain that binds specifically to human TIGIT and a second targeting domain that binds specifically to PD-1 or PD-L1.

In some embodiments, the bispecific checkpoint regulator antagonist comprises a one or more PD-1-specific CDRs of FIG. 3B or may include one or more PD-L1-specific CDRs of FIG. 3C. In some embodiments, the bispecific checkpoint regulator antagonist comprises a one or more PD-1-specific variable regions of FIGS. 4D-E or one or more PD-L1 specific variable regions of FIG. 4F-H.

In some embodiments, the bispecific checkpoint regulator antagonist is a full-length antibody that binds human TIGIT on one of its two binding arms (one pair of HC/LC), and binds a different antigen (or epitope) on its second arm (a different pair of HC/LC). In these embodiments, the bispecific antibody has two distinct antigen binding arms (in both specificity and CDR sequences), and is monovalent for each antigen it binds to.

In other embodiments, the bispecific checkpoint regulator antagonist is a full-length antibody that can bind human TIGIT and other antigens in each of its two binding arms (a pair of HC/LC). In these embodiments, the bispecific checkpoint regulator antagonist has two identical antigen binding arms, with identical specificity and identical CDR sequences, and is bivalent for each antigen it binds to.

FIGS. 17A-17N show a variety of different bispecific checkpoint regulator antagonists, M1-M14, where: (1) the VH1 and VL1 regions correspond to anti-PD1, anti-PD-L1 or any other mab variable domain; and (2) the VH2 and VL2 regions correspond to anti-TIGIT variable domains. FIGS. 17A-17D depict exemplary bispecific checkpoint regulator antagonist embodiments comprising a homodimer scaffold containing double chain arms with dual binding specificities (anti-TIGIT and anti-PD-1). FIGS. 17E and 17F depict exemplary bispecific checkpoint regulator antagonist embodiments comprising a homodimer scaffold containing a pair of double chain arms with a first binding specificity at the N-terminal of the constant regions and a pair of double chain arms with a second binding specificity at the C-terminal of the constant regions. FIGS. 17G-17J depict exemplary bispecific checkpoint regulator antagonist embodiments comprising a homodimer scaffold containing a pair of double chain arms with a first binding specificity at the N-terminal of the constant regions and a pair of single chain Fv (ScFv) fragments with a second binding specificity) at the C-terminal of the constant regions. FIGS. 17K-17N depict exemplary bispecific checkpoint regulator antagonist embodiments comprising a heterodimer scaffold containing a pair of double chain arms each having a different binding specificity. In these figures, the stars designate mutations in immunoglobulin constant regions that prevent mispairing of light or heavy chains from one binding specificity with light or heavy chains from another binding specificity as further discussed below.

Exemplary bispecific checkpoint regulator antagonist sequences are shown in FIG. 5. In one embodiment, a bispecific checkpoint regulator antagonist, TP-M2T8P5 comprises: (1) a heavy chain variable region having an amino acid sequence that is about 80% to about 100% homologous to the amino acid sequence in SEQ ID NO: 155; and (2) a variable light chain variable region having an amino acid sequence that is about 80% to about 100% homologous to the amino acid sequence in SEQ ID NO: 156.

In another embodiment, a bispecific checkpoint regulator antagonist, TP-M4T8P5 comprises: (1) a light chain variable region 2/heavy chain variable region 1 (VL2/VH1) having an amino acid sequence that is about 80% to about 100% homologous to the amino acid sequence in SEQ ID NO: 157; and (2) a heavy chain variable 2 region/light chain variable region 1 (VH2/VL1) having an amino acid sequence that is about 80% to about 100% homologous to the amino acid sequence in SEQ ID NO: 158.

In another embodiment, the bispecific checkpoint regulator inhibitor, TP-M6T8P5 comprises: (1) a heavy chain variable region having an amino acid sequence that is about 80% to about 100% homologous to the amino acid sequence in SEQ ID NO: 159; (2) a light chain variable region 2/light chain constant region (VL2/CL) having an amino acid sequence that is about 80% to about 100% homologous to the amino acid sequence in SEQ ID NO: 160; and (3) a heavy chain variable region 1/heavy chain constant region 1 (VH1/CH1) having an amino acid sequence that is about 80% to about 100% homologous to the amino acid sequence in SEQ ID NO: 161.

In another embodiment, the bispecific checkpoint regulator inhibitor, TP-M6T8L8 comprises: (1) a heavy chain variable region having an amino acid sequence that is about 80% to about 100% homologous to the amino acid sequence in SEQ ID NO: 162; (2) a light chain variable region 2/light chain constant region (VL2/CL) having an amino acid sequence that is about 80% to about 100% homologous to the amino acid sequence in SEQ ID NO: 163; and (3) a heavy chain variable region 1/heavy chain constant region 1 (VH1/CH1) having an amino acid sequence that is about 80% to about 100% homologous to the amino acid sequence in SEQ ID NO: 164.

In another embodiment, the bispecific checkpoint regulator inhibitor, TP-M8T10P1 (TP-83) comprises: (1) a heavy chain variable region having an amino acid sequence that is about 80% to about 100% homologous to the amino acid sequence in SEQ ID NO: 165; and (2) a light chain having an amino acid sequence that is about 80% to about 100% homologous to the amino acid sequence in SEQ ID NO: 166.

In another embodiment, the bispecific checkpoint regulator inhibitor, TP-M9T10P1 (TP-93) comprises: (1) a heavy chain that is about 80% to about 100% homologous to the amino acid sequence in SEQ ID NO: 167; and (2) a light chain having an amino acid sequence that is about 80% to about 100% homologous to the amino acid sequence in SEQ ID NO: 168.

In another embodiment, the bispecific checkpoint regulator inhibitor, TP-M9T10P5 comprises: (1) a heavy chain that is about 80% to about 100% homologous to the amino acid sequence in SEQ ID NO: 169; and (2) a light chain having an amino acid sequence that is about 80% to about 100% homologous to the amino acid sequence in SEQ ID NO: 170.

In another embodiment, the bispecific checkpoint regulator inhibitor, TP-M10T8P5 (TP-92) comprises: (1) a heavy chain that is about 80% to about 100% homologous to the amino acid sequence in SEQ ID NO: 171; and (2) a light chain variable region having an amino acid sequence that is about 80% to about 100% homologous to the amino acid sequence in SEQ ID NO: 172.

In another embodiment, the bispecific checkpoint regulator inhibitor, TP-M10T8L8 comprises: an amino acid sequence that is about 80% to about 100% homologous to the amino acid sequence in SEQ ID NO: 173.

In another embodiment, the bispecific checkpoint regulator inhibitor, TP-M14T8P5 comprises: (1) a heavy chain variable region 2/heavy chain constant region 1 (VH2/CH1) having an amino acid sequence that is about 80% to about 100% homologous to the amino acid sequence in SEQ ID NO: 174; (2) a variable light chain region 1/heavy chain constant region 1 (VL1/CH1) having an amino acid sequence that is about 80% to about 100% homologous to the amino acid sequence in SEQ ID NO: 175; (3) a light chain variable region 2/light chain constant region (VL2/CL) having an amino acid sequence that is about 80% to about 100% homologous to the amino acid sequence in SEQ ID NO: 176; and (4) a heavy chain variable region 1/light chain constant region (VH1/CL) having an amino acid sequence that is about 80% to about 100% homologous to the amino acid sequence in SEQ ID NO: 177.

In another embodiment, the bispecific checkpoint regulator inhibitor, TP-M14T8L8 comprises: (1) a heavy chain variable region 2/heavy chain constant region 1 (VH2/H11) having an amino acid sequence that is about 80% to about 100% homologous to the amino acid sequence in SEQ ID NO: 178; (2) a variable light chain region 1/heavy chain constant region 2 (VL1/HC2) having an amino acid sequence that is about 80% to about 100% homologous to the amino acid sequence in SEQ ID NO: 179; (3) a light chain variable region 2/light chain constant region (VL2/CL) having an amino acid sequence that is about 80% to about 100% homologous to the amino acid sequence in SEQ ID NO: 180; and (4) a heavy chain variable region 1/light chain constant region (VH1/CL) having an amino acid sequence that is about 80% to about 100% homologous to the amino acid sequence in SEQ ID NO: 181.

Trispecific Checkpoint Regulator Antagonists

In some embodiments, the trispecific checkpoint regulator antagonist comprises: (1) a first targeting domain having a first binding specificity conferred by one or more anti-TIGIT variable domains; (2) a second targeting conferred by one or more variable regions comprising one or more anti-PD1 variable domains, one or more anti-PD-L1 variable domains, or one or more variable region domains corresponding to any other anti-cancer targets, including other checkpoint regulators, as further described herein; and (3) a third targeting domain conferring by one or more peptide sequences (e.g., AMG386) or variable domain regions comprising a VEGF binding antagonist, Tie2 tyrosine kinase receptor antagonist or Tie2 tyrosine kinase receptor ligand antagonist as further described herein.

FIGS. 18A-18J show a variety of different trispecific checkpoint regulator antagonists, where: (1) the VH1 and VL1 regions correspond to anti-TIGIT variable domains; (2) the VH2 and VL21 regions correspond to anti-PD1, anti-PD-L1 or any other mab variable domain; and (3) the circular region corresponds to AMG386 or any other biological peptide.

Homedimers and Hetrodimers

One of the challenges for efficiently producing bispecific and trispecific checkpoint regulator antagonist preparations concerns mispairing of heavy and light chains when co-expressing chains of different binding specificities. Table 1 lists several amino acid substitution options for overcoming mispairing between heavy chains of different binding specificities, which "enforce" or preferentially promote correct association between desired heavy chains. Any approach to prevent or reduce mispairing between heavy chains may be used to make the bispecific or trispecific checkpoint regulator antagonists according to the present disclosure.

The "knobs-into-hole" (KiH) approach relies on modifications of the interface between the two CH3 domains where most interactions occur. Typically, a bulky residue is introduced into the CH3 domain of one antibody heavy chain and acts similarly to a key. In the other heavy chain, a "hole" is formed that is able to accommodate this bulky residue, mimicking a lock. The resulting heterodimeric Fc-part can be further stabilized by artificial disulfide bridges.

An alternative approach is based on charged residues with ionic interactions or steric complementarity. This includes altering the charge polarity in the CH3 interface so that co-expression of electrostatically matched Fc domains support favorable attractive interactions and heterodimer formation while retaining the hydrophobic core, whereas unfavorable repulsive charge interactions suppress homodimerization. See Table 1. The amino acid numbering in Table 1 follows the Kabat numbering scheme and can be applied to heavy chain amino acid sequences of the antibodies described herein.

In a further approach, leucine zipper (LZ) domains may be incorporated into a protein scaffold. A leucine zipper is a common three-dimensional structural motif in proteins, typically as part of a DNA-binding domain in various transcription factors. A single LZ typically contains 4-5 leucine residues at approximately 7-residue intervals, which forms an amphipathic alpha helix with a hydrophobic region running along one side. In a particular embodiment, a heterodimeric protein scaffold comprises a LZ from the c-jun transcription factor associated with a LZ from the c-fos transcription factor. Although c-jun is known to form jun-jun homodimers and c-fos does not form homodimers, the formation of jun-fos heterodimers is greatly favored over jun-jun homodimers.

A leucine zipper domain may be incorporated in place of CH2-CH3 sequences in the protein scaffold or it may be placed at the carboxy terminal end of the two heavy chains in the bispecific or trispecific checkpoint regulator antagonist. In the case of the latter, a furin cleavage site may be introduced between the carboxy terminal end of CH3 and the amino terminal end of the leucine zipper. This can facilitate furin-mediated cleavage of the leucine zipper following the heterodimerization step when co-expressing the heavy and light chains of the bispecific or trispecific checkpoint regulator antagonist in an appropriate mammalian cell expression system (see Wranik et al., J. Biol. Chem., 287 (5):43331-43339, 2012).

TABLE 1

| Type | HC1 | HC2 |
| --- | --- | --- |
| Knobs-into-holes | Y349C, T366S, L368A, Y407V | S354C, T366W |
| Ionic, electrostatic | S183E, E356K, E357K, D399K | S183K, K370E, K409D, K439E |
| Ionic, electrostatic | K392D, K409D | E356K, D399K |
| HA-TF substitutions | S364H, F405A | Y349T, T394F |
| HF-TA substitutions | S364H, T394F | Y349T, F405A |
| Leucine zipper heterodimer | human c-Jun leucine zipper | human c-fos leucine zipper |

The amino acid numbering in Table 1 follows the Kabat numbering scheme and can be applied to heavy chain amino acid sequences of the antibodies described herein. The mutations described in Table 1 may be applied to the sequence (published or otherwise) of any immunoglobulin IgG1 heavy chain, as well as other immunoglobulin classes, and subclasses (or isotypes) therein.

When co-expressing heavy and light chains of bispecific or trispecific antibodies, the light chains of one binding specificity can also mispair with heavy chains of a different binding specificity. Therefore, in certain embodiments, portions of the heavy chain, light chain or both may be modified relative to the "wild-type" antibody chains from which they are derived to prevent or reduce mispairing of both heavy chain constant regions to one another, as well mispairing of light chain constant regions to their heavy chain counterparts.

The light chain mispairing problem can be addressed in several ways. In some embodiments, sterically complementary mutations and/or disulfide bridges may be incorporated into the two VL/VH interfaces. In other embodiments, mutations can be incorporated based on ionic or electrostatic interactions. In some embodiments, light chain mispairing may be prevented or reduced by employing a first arm with an S183E mutation in the CH1 domain of the heavy chain and an S176K mutation in the CL domain of the light chain. A second arm may include an S183K mutation in the in the CH1 domain of the heavy chain and an S176E mutation in the CL domain of the light chain. In other embodiments, a "CrossMab" approach is employed, where one arm in the bispecific or trispecific checkpoint regulator antagonist (e.g., Fab) is left untouched, but in the other arm containing the other binding specificity, one or more domains in the light chain are swapped with one or more domains in the heavy chain at the heavy chain: light chain interface.

Methods, immunoglobulin domain sequences, including specific mutations for preventing mispairing of heavy and light chains as disclosed above are further described in U.S. Patent Application Publication Nos. 2014/0243505, 2013/0022601.

FIGS. 18G-18J depict exemplary trispecific checkpoint regulator antagonist embodiments in which the stars designate mutations in immunoglobulin constant regions that prevent mispairing of light or heavy chains from one binding specificity with light or heavy chains from another binding specificity.

Conjugates

In certain embodiments, the checkpoint regulator antagonists of the present application are chemically conjugated to one or more peptides and/or small molecule drugs. The peptides or small molecule drug can be the same or different. The peptides or small molecule drugs can be attached, for example to reduced SH groups and/or to carbohydrate side chains. Methods for making covalent or non-covalent conjugates of peptides or small molecule drugs with antibodies are known in the art and any such known method may be utilized.

In some embodiments the peptide or small molecule drug is attached to the hinge region of a reduced antibody component via disulfide bond formation. Alternatively, such agents can be attached using a heterobifunctional cross-linkers, such as N-succinyl 3-(2-pyridyldithio)propionate (SPDP). General techniques for such conjugation are well-known in the art. In some embodiments, the peptide or small molecule drug is conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent. Methods for conjugating peptide inhibitors or small molecule drugs to antibodies via antibody carbohydrate moieties is well-known to those of skill in the art. For example, in one embodiment, the method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate. Exemplary methods for conjugating small molecule drugs and peptides to antibodies are described in U.S. Patent Application Publication No. 2014/0356385.

Preferably, the checkpoint regulator antagonists in the present disclosure retain certain desirable characteristics and pharmacokinetic properties of antibodies, including a desirable in vitro and in vivo stability (e.g., lone half-life and shelf-life stability), efficient delivery into desired target cells, increased affinity for binding partners, desirable antibody-dependent cell-mediated cytotoxicity and complement-dependent cytotoxicity, and reduced renal clearance or excretion. Accordingly, careful attention to size and need for particular constant region effector functions may be considered in the design of the checkpoint regulator antagonists.

The anti-TIGIT, anti-PD-1 and anti-PD-L1 inhibitors, including monospecific, bispecific and trispecific checkpoint regulator antagonists therefrom, may range in size from 50 kD to 300 kD, from 50 kD to 250 kD, from 60 kD to 250 kD, from 80 kDa to 250 kD, from 100 kD to 250 kD, from 125 kD to 250 kD, from 150 kD to 250 kD, from 60 kD to 225 kD, from 75 kD to 225 kD, from 100 kD to 225 kD, from 125 kD to 225 kD, from 150 kD to 225 kD, from 60 kD to 200 kD, from 75 kD to 200 kD, from 100 kD to 125 kD to 200 kD, from 150 kD to 200 kD, from 60 kD to 150 kD, from 75 kD to 150 kD, from 100 kD to 150 kD, from 60 kD to 125 kD, from 75 kD to 125 kD, from 75 kD to 100 kD, or any range encompassed by any combination of whole numbers listed in the above cited ranges or any ranges specified by any combination of whole numbers between any of the above cited ranges.

Kits

The present application further provides a kit comprising the checkpoint regulator antagonist of the present application. In some embodiment, the kit comprises one or more of the anti-TIGIT, anti-PD-1 or anti-PD-L1 antibodies, and bispecific or trispecific checkpoint regulator antagonists thereof. In some embodiments, the kit further contains additional reagents, including secondary antibodies for detection, and additional human antibodies described herein (e.g., a human antibody having a complementary activity that binds to an epitope in TIGIT antigen distinct from the first human antibody). Kits typically include a label with instructions indicating the intended use of the contents of the kit. The term label includes any writing, or recorded material supplied on or with the kit, or which otherwise accompanies the kit.

Methods of Using the Checkpoint Regulator Antagonists

The checkpoint regulator antagonists of the present application, such as anti-TIGIT antibodies, anti-TIGIT antibody fragments, anti-PD-1 antagonists, anti-PD-1 antibody fragments, anti-PD-L1 antibodies, anti-PD-L1 antibody fragments, bispecific checkpoint regulator antagonists and trispecific checkpoint regulator antagonists that bind specifically to TIGIT, PD-1 and/or PD-L1, have numerous in vitro and in vivo utilities including, for example, enhancement of immune responses by blocking signaling by TIGIT, PD-1 and/or PD-L1, treatment of cancers, infectious diseases or autoimmune diseases, and detection of TIGIT, PD-1 and/or PD-L1.

In some embodiments, the checkpoint regulator antagonists of the present application are administered to cells in culture, in vitro or ex vivo, or to human subjects, e.g., in vivo, to enhance immunity in a variety of diseases. Accordingly, provided herein are methods of modifying an immune response in a subject comprising administering to the subject an antibody or antigen-binding fragment thereof as described herein such that the immune response in the subject is enhanced, stimulated or up-regulated. Preferred subjects include human patients in whom enhancement of an immune response would be desirable. The methods are particularly suitable for treating human patients having a disorder that can be treated by augmenting an immune response (e.g., the T-cell mediated immune response). The methods are particularly suitable for treatment of cancer or chronic infections in vivo. For example, the anti-TIGIT, anti-PD-1 or anti-PD-L1 compositions may be administered together with an antigen of interest or the antigen may already be present in the subject to be treated (e.g., a tumor-bearing or virus-bearing subject) to enhance antigen-specific immunity. When anti-TIGIT antibodies are administered together with another agent, the two can be administered separately or simultaneously.

In some embodiments, the checkpoint regulator anatagonist used in the above-described method is an anti-TIGIT, anti-PD-1, anti-PD-L1 antibody, fragment thereof, or combination thereof. In some embodiments, the checkpoint regulator anatagonist is a bispecific or trispecific antibody of the present application.

In some embodiments, the checkpoint regulator antagonist is an antibody or fragment. In some embodiments, the antibodies described herein are human or humanized antibodies.

Also encompassed are methods for detecting and/or measuring the presence of human TIGIT, human PD-1 or human PD-L1 in a sample comprising contacting the sample, and a control sample, with a human monoclonal antibody thereof, or an antigen binding fragment thereof, which specifically binds to human TIGIT, human PD-1 or human PD-L1 under conditions that allow for formation of a complex between the antibody or fragment thereof and human TIGIT, human PD-1 or human PD-L1. The formation of a complex is then detected, wherein a difference in complex formation between the sample compared to the control sample is indicative the presence of human TIGIT antigen in the sample. Moreover, the anti-TIGIT, anti-PD-1 or anti-PD-L1 antibody described herein can be used to purify human TIGIT via immunoaffinity purification.

Given the ability of anti-TIGIT, anti-PD-1 and anti-PD-L1 antibodies to block inhibition or co-inhibition of T cell responses, e.g., antigen-specific T cell responses, provided herein are in vitro and in vivo methods of using the antibodies described herein to stimulate, enhance or upregulate antigen-specific T cell responses, e.g., anti-tumor T cell responses. In certain embodiments, CD3 stimulation is also provided (e.g., by co-incubation with a cell expressing membrane CD3), which stimulation can be provided at the same time, before, or after treatment with an anti-TIGIT, anti-PD-1 or anti-PD-L1 antibody. For example, provided herein are methods of enhancing an antigen-specific T cell response comprising contacting said T cell with an anti-TIGIT, anti-PD-1 or anti-PD-L1 antibody described herein, and optionally with CD3, such that an antigen-specific T cell response is enhanced, e.g., by removal of a TIGIT-, PD-1 or PD-L1 mediated inhibitory effect. Any suitable indicator of an antigen-specific T cell response can be used to measure the antigen-specific T cell response. Non-limiting examples of such suitable indicators include increased T cell proliferation in the presence of the antibody and/or increase cytokine production in the presence of the antibody. In a preferred embodiment, interleukin-2 and/or interferon-γ production by the antigen-specific T cell is enhanced.

Further encompassed are methods for enhancing an immune response (e.g., an antigen-specific T cell response) in a subject comprising administering an anti-TIGIT antibody, an anti-PD-1 antibody, an anti-PD-L1 antibody, or a bispecific or trispecific checkpoint regulator antagonist described herein to the subject such that an immune response (e.g., an antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In other embodiments, a tumor is non-immunogenic. In certain embodiments, a tumor is PD-L1 positive. In other embodiments a tumor is PD-L1 negative. A subject may also be a virus-bearing subject in which an immune response against the virus is enhanced as a consequence of administering an anti-TIGIT antibody, anti-PD-1 antibody, anti-PD-L1 antibody, bispecific checkpoint regulator antagonist, or trispecific checkpoint regulator antagonist as described herein.

In one embodiment, a method for inhibiting the growth of tumor cells in a subject comprises administering to the subject an anti-TIGIT antibody, anti-PD-1 antibody, anti-PD-L1 antibody, bispecific checkpoint regulator antagonist, or trispecific checkpoint regulator antagonist described herein such that growth of the tumor is inhibited in the subject. Also provided are methods of treating chronic viral infection in a subject comprising administering to the subject an anti-TIGIT antibody, anti-PD-1 antibody, anti-PD-L1 antibody, bispecific checkpoint regulator antagonist, or trispecific checkpoint regulator antagonist as described herein such that the chronic viral infection is treated in the subject.

Also encompassed herein are methods for depleting Treg cells from the tumor microenvironment of a subject with a tumor, e.g., cancerous tumor, comprising administering to the subject a therapeutically effective amount of an anti-TIGIT antibody, anti-PD-1 antibody, anti-PD-L1 antibody, bispecific checkpoint regulator antagonist, or trispecific checkpoint regulator antagonist described herein that comprises an Fc that stimulates depletion of Treg cells in the tumor microenvironment. An Fc may, e.g., be an Fc with effector function or enhanced effector function, such as binding or having enhanced binding to one or more activating Fc receptors.

In a preferred embodiment, Treg depletion occurs without significant depletion or inhibition of $T_{\it eff}$ in the tumor microenvironment, and without significant depletion or inhibition of $T_{\it eff}$ cells and Treg cells outside of the tumor microenvironment. In certain embodiments, the subject has higher levels of TIGIT on Treg cells than on $T_{\it eff}$ cells, e.g., in the tumor microenvironment. In certain embodiments, anti-TIGIT antibodies or antagonists may deplete $T_{\it regs}$ in tumors and/or $T_{\it regs}$ in tumor infiltrating lymphocytes (TILs). For example, in the CT26 tumor model, an anti-mouse TIGIT antibody formatted as a mouse IgG2a (which exhibits effector function) partially depleted both Treg and CD8$^+$ T cells, but did not deplete CD4$^+$ T cells. An effectorless counterpart anti-TIGIT antibody, formatted as a mouse IgG1 D265A, did not deplete T cells.

When considering whether or not to employ Fc effector function or an effectorless anti-TIGIT antibody, due consideration must be given to the tradeoff between depletion of $T_{\it regs}$, which may enhance anti-tumor immune response, and depletion of CD8$^+$ T cells, which would eliminate some of the cells needed to actually kill tumor cells. Although depletion of $T_{\it regs}$ might be expected to enhance anti-tumor activity, recent studies have demonstrated that ligation of TIGIT on TIGIT$^+$ $T_{\it regs}$ promotes Treg cell-mediated suppression of $T_{\it eff}$ cell proliferation (Joller et al. (2014) Immunity 40:569), suggesting that blocking of TIGIT signaling (e.g., using an antagonist anti-TIGIT antibody of the present invention) might also enhance anti-tumor activity. Accordingly, it may be most efficacious to use an antagonist anti-TIGIT antibody lacking effector function, which: i) blocks TIGIT signaling in $T_{\it regs}$ thus reducing their immunesuppresive activity; ii) activates anti-tumor CD8+ Tcells by blocking TIGIT's inhibitory effects, while at the same time avoiding their effector-function-mediated depletion; and iii) enhances DNAM-mediated activation by allowing DNAM to bind to PVR (CD155, the TIGIT ligand) that would otherwise have been bound by TIGIT (and by reducing direct TIGIT-DNAM interactions) (Johnston et al. (2014) Cancer Cell 26:923). The same is applicable to use of anti-PD-1 antibodies, anti-PD-L1 antibodies, bispecific checkpoint regulator antagonists, or trispecific checkpoint regulator antagonists.

In certain embodiments, an anti-TIGIT antibody, anti-PD-1 antibody, anti-PD-L1 antibody, bispecific checkpoint regulator antagonist, or trispecific checkpoint regulator antagonist described herein is given to a subject as an adjunctive therapy. Treatment of cancer patient with an anti-TIGIT antibody, anti-PD-1 antibody, anti-PD-L1 antibody, bispecific checkpoint regulator antagonist, or trispecific checkpoint regulator antagonist according to the present application may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a cancer patient with an anti-TIGIT antibody, anti-PD-1 antibody, anti-PD-L1 antibody, bispecific checkpoint regulator antagonist, or trispecific checkpoint regulator antagonist prevents recurrence of cancer or delays recurrence of cancer by, e.g., 1, 2, 3, 4, 5, or 10 or more years. An anti-TIGIT, anti-PD-1 and/or anti-PD-L1 treatment can be used as a primary or secondary line of treatment.

In certain preferred embodiments, the subject has a cell proliferative disease or cancer. Blocking of PVR/Nectin-2 signaling through TIGIT by anti-TIGIT antibodies can enhance the immune response to cancerous cells in the patient. Similarly, blocking of Provided herein are methods for treating a subject having cancer, comprising administering to the subject an anti-TIGIT, anti-PD-1, anti-PD-L1, bispecific checkpoint regulator antagonist, or trispecific checkpoint regulator antagonist thereof as described herein, such that the subject is treated, e.g., such that growth of cancerous tumors is inhibited or reduced and/or that the tumors regress. An anti-TIGIT anti-PD-1, anti-PD-L1, bispecific checkpoint regulator antagonist, or trispecific checkpoint regulator antagonist thereof as described herein can be used alone to inhibit the growth of cancerous tumors. Alternatively, any of these checkpoint regulator antagonists can be used in conjunction with another agent, e.g., other anti-cancer targets, immunogenic agents, standard cancer treatments, or other antibodies, as described below.

Accordingly, provided herein are methods of treating cancer, e.g., by inhibiting growth of tumor cells, in a subject, comprising administering to the subject a therapeutically effective amount of an anti-TIGIT, anti-PD-1, anti-PD-L1, bispecific checkpoint regulator antagonist, or trispecific checkpoint regulator antagonist as described herein. Preferably, the antibody is a human anti-TIGIT, anti-PD-1 or anti-PD-L1 antibody comprising the anti-TIGIT, anti-PD-1 or anti-PD-L1 HCVRs and LCVR described herein, or it may be a chimeric or humanized non-human anti-hu TIGIT, anti-hu PD-1 or anti-PD-L1 antibody, e.g., a chimeric or humanized anti-TIGIT, anti-PD-1 or anti-PD-L1 antibody that competes for binding with, or binds to the same epitope as, at least one of the anti-TIGIT, anti-PD-1 or anti-PD-L1 antibodies described herein.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CIVIL), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NEIL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTCL) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

An anti-TIGIT, anti-PD-1 antibody, anti-PD-L1 antibody, bispecific checkpoint regulator antagonist, or trispecific checkpoint regulator antagonist can be administered alone, in combination with another checkpoint regulator antagonist, or concurrently with another checkpoint regulator antagonist. An anti-TIGIT, anti-PD-1 antibody, anti-PD-L1 antibody, bispecific checkpoint regulator antagonist, or trispecific checkpoint regulator antagonist can also be administered in combination, or concurrently with, an immunogenic agent, such as cancerous cells, tumor vaccines, purified tumor antigens (including recombinant proteins, peptides, and carbohydrate molecules), cells transfected with genes encoding immune stimulating cytokines, in a cancer vaccine strategy (He et al. (2004) J. Immunol. 173:4919-28), or an oncolytic virus.

Many experimental strategies for vaccination against tumors have been devised. In one of these strategies, a vaccine is prepared using autologous or allogeneic tumor cells. Some of these cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43). Cancer vaccines have been shown to enhance effector T-cell infiltration into the tumors in preclinical models. The major types of cancer vaccines include peptide vaccines, vector-based antigen specific vaccines, whole-cell vaccines, and dendritic cell vaccines. All vaccine-based therapies are designed to deliver either single or multiple antigenic epitopes or antigens from the whole cells to the patients and induce tumor-specific effector T cells. Thus, a vaccine-based therapy may be the most efficient way to induce T-cell infiltration into the tumor.

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2.

More importantly, many of these antigens can be shown to be the targets of tumor specific T cells found in the host.

TIGIT, PD-1 and/or PD-L1 inhibition may be used in conjunction with a collection of recombinant proteins and/or peptides expressed in a tumor in order to generate an immune response to these proteins. These proteins are normally viewed by the immune system as self-antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) Science 266: 2011-2013). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Non-limiting examples of tumor vaccines include sipuleucel-T (Provenge®), an FDA-approved tumor vaccine for Metastatic prostate cancer; tumor cells transfected to express the cytokine granulocyte macrophage colony-stimulating factor (GM-CSF), such as the whole cell GM-CSF-secreting irradiated, allogeneic pancreatic cancer vaccine (GVAX; Johns Hopkins); a multi-peptide vaccine consisting of immunogenic peptides derived from breast cancer antigens, neu, legumain, and .beta.-catenin, which prolonged the vaccine-induced progression-free survival of breast tumor-bearing mice when administered in combination with anti-PD-1 antibody (Karyampudi L. et al. (2014) Cancer Res 74:2974-2985); peptides of melanoma antigens, such as peptides of gp100, MAGE antigens, Trp-2, MARTI and/or tyrosinase, or. Other tumor vaccines include proteins from viruses implicated in human cancers such as human papilloma viruses (HPV)(e.g., Gardasil °, Gardasil 9, and Cervarix; hepatitis B virus (e.g., Engerix-B and Recombivax HB); hepatitis C virus (HCV), Kaposi's sarcoma associated herpes sarcoma virus (KSHV). Another form of tumor specific antigen that can be used in conjunction with TIGIT inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity. Talimogene laherparepvec (T-VEC, or Imlygic®) is an FDA-approved oncolytic virus for the treatment of some patients with metastatic melanoma that cannot be surgically removed.

Dendritic cells (DC) are potent antigen presenting cells that can be used to prime antigen-specific responses. DC's can be produced ex vivo and loaded with various protein and peptide antigens, as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) Nature Medicine 6:332-336). As a method of vaccination, DC immunization may be effectively combined with TIGIT blocking to activate (unleash) more potent anti-tumor responses.

TIGIT, PD-1 and/or PD-L1 inhibition can also be combined with standard cancer treatments (e.g., surgery, radiation, and chemotherapy). In particular, TIGIT, PD-1 and/or PD-L1 inhibition can be effectively combined with chemotherapeutic regimes. In these instances, it may be possible to reduce the dose of chemotherapeutic reagent administered (Mokyr et al. (1998) Cancer Research 58: 5301-5304). An example of such a combination is a checkpoint regulator antagonist in combination with decarbazine for the treatment of melanoma. Another example of such a combination is a checkpoint regulator antagonist in combination with interleukin-2 (IL-2) for the treatment of melanoma. For example, the scientific rationale behind the combined use of TIGIT, PD-1 and/or PD-L1 inhibition and chemotherapy to promote cell death is a consequence of the cytotoxic action of most chemotherapeutic compounds, should result in increased levels of tumor antigen in the antigen presentation pathway. Other combination therapies that may result in synergy with TIGIT, PD-1 and/or PD-L1 inhibition through cell death are radiation, surgery, and hormone deprivation. Each of these protocols creates a source of tumor antigen in the host. Angiogenesis inhibitors can also be combined with TIGIT, PD-1 and/or PD-L1 inhibition. Inhibition of angiogenesis leads to tumor cell death, which may feed tumor antigen into host antigen presentation pathways.

The anti-TIGIT antibodies, anti-PD-1 antibodies, anti-PD-L1 antibodies, bispecific checkpoint regulator antagonists and trispecific checkpoint regulator antagonists described herein may also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the inhibition of TIGIT, PD-1 and/or PD-L1. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-.beta., IL-10, and Fas ligand. Antibodies to each of these entities can be used in combination with the checkpoint regulator antagonists described herein to counteract the effects of the immunosuppressive agent and favor tumor immune responses by the host.

Other antibodies that activate host immune responsiveness can be used in combination with the checkpoint regulator antagonists described herein. These include molecules on the surface of dendritic cells that activate DC function and antigen presentation. Anti-CD40 antibodies are able to substitute effectively for T cell helper activity (Ridge et al. (1998) Nature 393: 474-478) and can be used in conjunction with anti-TIGIT antibodies. Activating antibodies to T cell costimulatory molecules, such as OX-40 (Weinberg et al. (2000) Immunol 164: 2160-2169), CD137/4-1BB (Melero et al. (1997) Nature Medicine 3: 682-685 (1997), and ICOS (Hutloff et al. (1999) Nature 397: 262-266) may also provide for increased levels of T cell activation. In addition, inhibitors of other immune checkpoint regulators, may also be used in conjunction with checkpoint regulator antagonists described herein, as further described below.

Bone marrow transplantation is currently being used to treat a variety of tumors of hematopoietic origin. While graft versus host disease is a consequence of this treatment, TIGIT inhibition may be used to increase the effectiveness of the donor engrafted tumor specific T cells by reducing graft vs. tumor responses.

Ex vivo activation and expansion of antigen specific T cells and adoptive transfer of these cells into recipients in order to stimulate antigen-specific T cells against cancers or viral infections in the presence of anti-TIGIT antibodies can increase the frequency and activity of the adoptively transferred T cells.

There are also several experimental treatment protocols that involve ex vivo activation and expansion of antigen specific T cells and adoptive transfer of these cells into recipients in order to stimulate antigen-specific T cells against tumor (Greenberg & Riddell (1999) Science 285: 546-51). These methods can also be used to activate T cell responses to infectious agents such as CMV. Ex vivo activation in the presence of anti-TIGIT antibodies can increase the frequency and activity of the adoptively transferred T cells.

In certain embodiments, a checkpoint regulator antagonist described herein may be administered to a subject with an infectious disease, especially chronic infections. In this case, similar to its application to cancer, antibody-mediated TIGIT, PD-1 and/or PD-L1 inhibition can be used alone, or as an adjuvant, in combination with vaccines, to enhance immune responsiveness to pathogens, toxins, and self-antigens. Exemplary pathogens for which this therapeutic approach can be applied include, but are not limited to, HIV, Hepatitis (A, B, & C), Influenza, Herpes, Giardia, Malaria, *Leishmania, Staphylococcus aureus*, and *Pseudomonas aeruginosa*. TIGIT, PD-1 and/or PD-L1 inhibition is particularly useful against established infections by agents such as HIV that present novel or altered antigens over the course of the infections. Administration of the anti-TIGIT antibodies, anti-PD-1 antibodies, anti-PD-L1 antibodies, bispecific checkpoint regulator antagonists, and trispecific checkpoint regulator antagonists can allow for recognition of these antigens as foreign so as to provoke an appropriate T cell response.

Other pathogenic viruses causing infections treatable by the methods described herein include HIV, hepatitis (A, B, or C), herpesvirus infections (e.g., VZV, HSV-1, HAV-6, HSV-II, and CMV, Epstein Barr virus), and infections caused by an adenovirus, influenza virus, flavivirus, echoviruses, rhinoviruses, coxsackie viruses, coronaviruses, respiratory syncytial viruses, mumps viruses, rotavirus, measles virus, rubella virus, parvovirus, vaccinia virus, HTLV virus, dengue virus, papillomavirus, molluscum virus, poliovirus, rabies virus, JC virus, arboviral encephalitis virus, or combination thereof.

Exemplary pathogenic bacteria or diseases caused therefrom which may be treatable by the methods described herein include *Chlamydia, Rickettsia*, Mycobacteria, Staphylococci, Streptococci, Pneumonococci, Meningococci and Gonococci, *Klebsiella, Proteus, Serratia, Pseudomonas, Legionella, Diphtheria, Salmonella*, Bacilli, Cholera, Leptospirosis *tetanus*, botulism, anthrax, plague, and Lyme disease.

Exemplary pathogenic fungi causing infections treatable by the methods described herein include *Candida* (e.g., *albicans, krusei, glabrata, tropicalis*, etc.), *Cryptococcus neoformans, Aspergillus* (e.g., *fumigatus, niger*, etc.), Mucorales (e.g., *mucor, absidia, rhizopus*), *Sporothrix schenkii, Blastomyces dermatitidis, Paracoccidioides brasiliensis, Coccidioides immitis* and *Histoplasma capsulatum*.

Exemplary pathogenic parasites causing infections treatable by the methods described herein include *Entamoeba histolytica, Balantidium coli, Naegleriafow leri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis.*

In all of the above methods, TIGIT, PD-1 and/or PD-L1 inhibition can be combined with other forms of immunotherapy such as cytokine treatment (e.g., interferons, GM-CSF, G-CSF, IL-2), or bispecific antibody therapy using two different binding specificities to provide enhanced presentation of tumor antigens.

Anti-TIGIT antibodies, anti-PD-1 antibodies, anti-PD-L1 antibodies, bispecific checkpoint regulator antagonists, and trispecific checkpoint regulator antagonists described herein can be used to enhance antigen-specific immune responses by co-administration of one or more of any of these antibodies with an antigen of interest (e.g., a vaccine). Accordingly, provided herein are methods of enhancing an immune response to an antigen in a subject, comprising administering to the subject: (i) the antigen; and (ii) an anti-TIGIT antibody, anti-PD-1 antibody, anti-PD-L1 antibody, bispecific checkpoint regulator antagonist, trispecific checkpoint regulator antagonist, or combination thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

In certain embodiments, a peptide or fusion protein comprising the epitope to which an anti-TIGIT antibody, anti-PD-1 antibody, anti-PD-L1 antibody, bispecific checkpoint regulator antagonist, trispecific checkpoint regulator antagonist binds may be used as a vaccine instead of, or in addition to, the checkpoint regulator antagonist(s).

Suitable routes of administering the antibody compositions (e.g., human monoclonal antibodies, multi-specific antibodies or antagonists and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Combination Therapies

In another aspect, the present application provides combination therapies for enhancing an antigen-specific T cell response in a subject. In one embodiment, the method includes contacting a T cell with an anti-TIGIT antibody, anti-PD-1 antibody, anti-PD-L1 antibody, antibody fragment thereof, bispecific checkpoint regulator antagonist, or tri specific checkpoint regulator antagonist in combination with a second antibody, antibody fragment, antagonist or drug such that an antigen-specific T cell response or apoptotic pathway is enhanced. For example, in some embodiments, the first antibody or antibody fragment specifically binds TIGIT and the second antibody or antibody fragment specifically binds to PD-1 or PD-L1. In some embodiments, the second antibody or antibody fragment comprises one or more anti-PD-1 CDRs of FIG. 3B. In some embodiments, the second antibody or antibody fragment comprises one or more anti-PD-1 variable regions of FIGS. 4D-E.

In a related aspect, a method of reducing or depleting regulatory T cells in a tumor of a subject in need thereof includes administering an effective amount of an antibody or antibody fragment in combination with a second antibody, antibody fragment, antagonist or drug such that the number of regulatory T cells in the subject is reduced.

In some embodiments, the subject has a cell proliferative disease or cancer as described herein.

In other embodiments, the subject has a chronic viral infection, inflammatory disease or autoimmune disease as described herein.

The provision of two distinct signals to T-cells is a widely accepted model for lymphocyte activation of resting T lymphocytes by antigen-presenting cells (APCs). This model further provides for the discrimination of self from non-self and immune tolerance. The primary signal, or antigen specific signal, is transduced through the T-cell receptor (TCR) following recognition of foreign antigen peptide presented in the context of the major histocompatibility-complex (WIC). The second or co-stimulatory signal is delivered to T-cells by co-stimulatory molecules expressed on antigen-presenting cells (APCs), and induce T-cells to promote clonal expansion, cytokine secretion and effector function. In the absence of co-stimulation, T-cells can become refractory to antigen stimulation, which results in a tolerogenic response to either foreign or endogenous antigens.

In the two-signal model, T-cells receive both positive co-stimulatory and negative co-inhibitory signals. The regulation of such positive and negative signals is critical to maximize the host's protective immune responses, while maintaining immune tolerance and preventing autoimmunity. Negative signals seem necessary for induction of T-cell tolerance, while positive signals promote T-cell activation. Both co-stimulatory and co-inhibitory signals are provided to antigen-exposed T cells, and the interplay between co-stimulatory and co-inhibitory signals is essential to controlling the magnitude of an immune response. Further, the signals provided to the T cells change as an infection or immune provocation is cleared, worsens, or persists, and these changes powerfully affect the responding T cells and re-shape the immune response.

The mechanism of co-stimulation is of therapeutic interest because the manipulation of co-stimulatory signals has shown to provide a means to either enhance or terminate cell-based immune response. Recently, it has been discovered that T cell dysfunction or anergy can occur concurrently with an induced and sustained expression of immune checkpoint regulators, such as programmed death 1 polypeptide (PD-1) and its ligands, PD-L1 and PD-L2. PD-L1 is overexpressed in many cancers and is often associated with poor prognosis (Thompson R H et al., Cancer Res 2006, 66(7): 3381). Further, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance. Inhibition of the PD-L1/PD-1 interaction provides a means to enhance T cell immunity, including CD8+ T cell-mediated killing of cancer cells and tumors. Similar enhancements to T cell immunity have been observed by inhibiting the binding of PD-L1 to the binding partner B7-1. Consequently, therapeutic targeting of PD-1 and other immune checkpoint regulators are an area of intense interest.

Combining inhibition of TIGIT, PD-1 and/or PD-L1 signaling with other signaling pathways deregulated in tumor cells can provide a means for enhance treatment efficacy. In recent years, a number of immune checkpoint regulators in the form of receptors and their ligands have been identified. One important family of membrane-bound ligands that bind to co-stimulatory or co-inhibitory receptors is the B7 family, which includes CTLA-4 and its ligands, B7-1 and B7-2; PD-1 and its ligands, PD-L1 (B7-H1) and PD-L2 (B7-DC); B7-H2 (ICOS-L), B7-H3, B7-H4, B7-H5 (VISTA), and B7-H6. Additional immune checkpoint antagonists include, but are not limited to TIM-3 and its ligand, Galectin-9; LAG-3 and its ligands, including liver sinusoidal endothelial cell lectin (LSECtin) and Galectin-3; CD122 and its CD122R ligand; CD70, B7H3, B and T lymphocyte attenuator (BTLA), and VISTA (Le Mercier et al. (2015) Front. Immunol., (6), Article 418). In addition, a number of checkpoint regulator antagonists have been identified and tested in various clinical and pre-clinical models and/or approved by the FDA (Kyi et al., FEBS Letters, 588:368-376 (2014). The concept of inhibitory receptor blockade, also known as immune checkpoint blockade, has been validated by virtue of e.g., the FDA approval of the PD-1 inhibitors, nivolumab and pembrolizumab, as well as the anti-CTLA-4 antibody, ipilimumab for metastatic melanoma.

An immune checkpoint antagonist modulates or interferes with the activity of the immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. In contrast, an immune checkpoint agonist (of e.g., a costimulatory molecule) stimulates the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced.

Accordingly, in one embodiment, a method for stimulating an immune response in a subject comprises administering to the subject an anti-TIGIT antibody, anti-PD-1 antibody, anti-PD-L1 antibody, antibody fragment(s) thereof (e.g., anti-TIGIT HCVR and/LCVRs) or bispecific checkpoint regulator antagonist, or trispecific checkpoint regulator antagonist described herein in combination with another immune checkpoint regulator described herein above, such that an immune response is stimulated in the subject, for example to inhibit tumor growth or to stimulate an anti-viral response.

In one embodiment, an anti-TIGIT antibody, anti-PD-1 antibody, anti-PD-L1 antibody, antibody fragment(s) thereof, bispecific checkpoint regulator antagonist, or trispecific checkpoint regulator antagonist according to the present application is administered in combination with another immune checkpoint regulator, either as separate antibodies or in multi-specific antibody comprising binding specificities to multiple products. Generally, an anti-TIGIT antibody, anti-PD-1 antibody, anti-PD-L1 antibody, bispecific checkpoint regulator antagonist, or trispecific checkpoint regulator antagonist described herein can be combined to stimulate an immune response with (i) an antagonist of the IgSF family protein, B7 family or TNF family that inhibit T cell activation, or antagonist of a cytokine that inhibits T cell activation (e.g., IL-6, IL-10, TGF-.beta., VEGF, or other immunosuppressive cytokines) and/or (ii) an agonist of a stimulatory receptors of the IgSF family, B7 family or TNF family or of cytokines to stimulate T cell activation, for stimulating an immune response.

In one embodiment, the subject is administered an anti-TIGIT antibody or HCVR and/or LCVR fragments thereof in combination with an anti-PD-1 antibody or PD-1 antagonist. In another embodiment, the subject is administered is administered an anti-TIGIT antibody or HCVR and/or LCVR fragments thereof in combination with an anti-PD-L1 antibody or PD-L1 antagonist. In another embodiment, the subject is administered an anti-TIGIT antibody or HCVR and/or LCVR fragments thereof in combination with an anti-CTLA-4 antibody or CTLA-4 antagonist.

In certain embodiments, only subjects with a cancer exhibiting high expression of a ligand for an immune checkpoint regulator are selected for combination treatment with the anti-TIGIT, anti-PD-1 and/or anti-PD-L1 antibody, fragment thereof, or any of the bispecific or trispecific antagonists of the present application. By way of example, in one embodiment, a subject with a cancer exhibiting high expression of PVR (CD155) and/or Nectin-2 (CD112) and/or low expression PD-L1 may be selected for monotherapy with anti-TIGIT antibodies, fragments thereof, or TIGIT antagonists of the present application, or combination therapy with a PD-1 antagonist or other immune checkpoint regulator.

The anti-TIGIT antibody, anti-PD-1 antibody, anti-PD-L1 antibody may be administered separately from the second antibody, antibody fragment or antagonist, or a multispecific antibody or antagonist may be administered comprising at least one binding specificity for TIGIT and a second binding specificity for the other targeted product. Further, the anti-TIGIT, anti-PD-1 antibody, anti-PD-L1 antibody or bispecific or trispecific antagonist in accordance with the present application may be co-administered with one or more additional agents, e.g., antibodies, antagonists, or drugs in amount(s) effective in stimulating an immune response and/or apoptosis so as to further enhance, stimulate or upregulate an immune response and/or apoptosis in a subject.

In some embodiments, the anti-TIGIT, anti-PD-1 or anti-PD-L1 antibody or fragment(s) thereof is administered subsequent to treatment with a different immune checkpoint regulator antagonist. For example, in one embodiment, anti-TIGIT, anti-PD-1 or anti-PD-L1 antibodies may be administered only after treatment with a PD-1/PD-L1 antagonist has failed, has led to incomplete therapeutic response, or there has been recurrence of the tumor or relapse (or "PD-1 failure"). In some embodiments, cancers exhibiting such failures may be screened for expression of e.g., PVR and/or Nectin-2 and only those having high level expression are treated with an anti-TIGIT, anti-PD-1 or anti-PD-L1 antibody, fragment or antagonist of the present application.

In a particular embodiment, the anti-TIGIT, anti-PD-1 or anti-PD-L1 antibody or fragment is administered in combination with a PD-1, PD-L1, PD-L2 or TIGIT antagonist.

Other anti-PD-1 antibodies include, but are not limited to, nivolumab (BMS-936558, MDX-1106, OPDIVO™), a humanized immunoglobulin G4 (IgG4) mAb (Bristol-Myers Squibb); pembrolizumab (MK-3475, lambrolizumab, KEYTRUDA™)(Merck); pidilizumab (CT-011)(Medivation); and AMP-224 (Merck). Anti-PD-1 antibodies are commercially available, for example from ABCAM (AB137132), BIOLEGEND™ (EH12.2H7, RMP1-14) and AFFYMETRIX EBIOSCIENCE (J105, J116, MIH4). Anti-PD-1 antibodies also includes antibodies or antibody fragments containing one or more anti-PD-1 CDRs of FIG. 3B, or one or more anti-PD-1 variable regions of FIGS. 4D-E.

Other anti-PD-L1 antibodies include atezolizumab (MPDL3280A, RG7446), a fully human IgG4 mAb Genentech/Roche); BMS-936559 (MDX-1105), a fully humanized IgG4 mAb (Bristol-Myers Squibb); MEDI4736, a humanized IgG antibody (Medimmune/AstraZeneca); and MSB0010718C, a fully human IgG4 monoclonal antibody (Merck, EMD Serono).

Exemplary anti-CTLA-4 antibodies for use in accordance with the present methods include ipilimumab, trevilizumab and tremelimumab. Exemplary anti-CTLA-4 dominant negative proteins include the humanized fusion protein, Abatacept (Orencia), which comprises the Fc region of IgG1 fused to the CTLA-4 ECD, and Belatacept (Nulojix®), a second generation higher-affinity CTLA-4-Ig variant with two amino acid substitutions in the CTLA-4 ECD relative to Abatacept.

In certain embodiments, the immune checkpoint regulator antagonist is a dominant negative protein of the immune checkpoint regulator. In particular embodiments, the dominant negative protein comprises an extracellular domain derived from a member selected from the group consisting of PD-L1, PD-L2, PD-1, B7-1, B7-2, B7H3, CTLA-4, LAG-3, TIM-3, TIGIT, BTLA, VISTA, CD70, and combinations thereof. In certain particular embodiments, these extracellular domains are fused to an immunoglobulin constant region or Fc receptor in the presently described antibodies. Such mutants can bind to the endogenous receptor so as to form a complex that is deficient in signaling. In certain embodiments, the extracellular domain is fused to an immunoglobulin constant region or Fc fragment or to a monomer in the oligomeric protein complex.

In certain embodiments, a dominant negative PD-L1 antagonist comprises the extracellular domain of PD-L1, PD-L2, or PD-1. In another embodiment, a dominant-negative PD-1 antagonist is employed, which has a mutation so that it is no longer able to bind PD-L1. An exemplary dominant negative protein is AMP-224 (co-developed by Glaxo Smith Kline and Amplimmune), a recombinant fusion protein comprising the extracellular domain of PD-L2 and the Fc region of human IgG.

Exemplary immune checkpoint regulator agonists include, but are not limited to members of the tumor necrosis factor (TNF) receptor superfamily, such as CD27, CD40, OX40, GITR and 4-1BB (CD137) and their ligands, or members of the B7-CD28 superfamily, including CD28 and ICOS (CD278). Additional checkpoint regulator agonists include CD2, CDS, ICAM-1, LFA-1 (CD11a/CD18), CD30, BAFFR, HVEM, CD7, LIGHT, NKG2C, SLAMF7, NKp80, CD160, B7-H3, CD83 ligand. Immune checkpoint agonists can include antibodies or soluble fusion protein agonists comprising one or more costimulatory domains. Agonist antibodies include, but are not limited to anti-CD40 mAbs, such as CP-870,893, lucatumumab, and dacetuzumab; anti-CD137 mAbs, such as BMS-663513 urelumab, and PF-05082566; anti-OX40 mAbs; anti-GITR mAbs, such as TRX518; anti-CD27 mAbs, such as CDX-1127; and anti-ICOS mAbs.

Exemplary GITR agonists include, e.g., GITR fusion proteins and anti-GITR antibodies (e.g., bivalent anti-GITR antibodies) such as, e.g., a GITR fusion protein described in U.S. Pat. Nos. 6,111,090 and 8,586,023; European Patent No.: 090505B1, U.S. Pat. No. PCT Publication Nos.: WO 2010/003118 and 2011/090754. Anti-GITR antibodies are described in, e.g., in U.S. Pat. Nos. 7,025,962, 7,618,632, 7,812,135, 8,388,967, and 8,591,886; European Patent Nos.: 1947183B1 and 1866339; PCT Publication Nos.: WO 2011/028683, WO 2013/039954, WO2005/007190, WO 2007/133822, WO2005/055808, WO 99/40196, WO 2001/03720, WO99/20758, WO2006/083289, WO 2005/115451, WO 2011/051726. An exemplary anti-GITR antibody is TRX518.

Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TALI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFγ, TNFR2, TNFα, LTβR, Lymphotoxin α1 (32, FAS, FASL, RELT, DR6, TROY, NGFR (see, e.g., Tansey, M. G. et al. (2009) Drug Discovery Today, 14 (23-24):1082-1088).

Immune checkpoint agonists or costimulatory molecules include cell surface molecules other than antigen receptors or their ligands that are required for an efficient immune response, and include, but are not limited to MEW class I molecules, TNF receptor proteins, immunoglobulin-like proteins, cytokine receptors, integrins, signaling lymphocytic activation molecules (SLAM proteins), activating NK cell receptors, BTLA, Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83.

In one aspect, T cell responses can be stimulated by a combination of the anti-TIGIT, anti-PD-1 or anti-PD-L1 mAbs of the present invention and one or more of (i) an antagonist of a protein that inhibits T cell activation (e.g., immune checkpoint inhibitors), such as CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD-1H, LAIR1, TIM-1, CD96 and TIM-4, and (ii) an agonist of a protein that stimulates T cell activation such as B7-1, B7-2, CD28, 4-1BB (CD137), 4-1BBL, ICOS, CD40, ICOS-L, OX40, OX40L, GITR, GITRL, CD70, CD27, CD40, DR3 and CD28H.

Exemplary agents that modulate one of the above proteins and may be combined with anti-TIGIT antibodies, e.g., those described herein, for treating cancer, include: YERVOY™/ipilimumab or tremelimumab (to CTLA-4), galiximab (to B7.1), OPDIVO™/nivolumab/BMS-936558 (to PD-1), pidilizumab/CT-011 (to PD-1), KEYTRUDA™/pembrolizumab/MK-3475 (to PD-1), AMP224 (to B7-DC/PD-L2), BMS-936559 (to B7-H1), MPDL3280A (to B7-H1), MEDI-570 (to ICOS), AMG557 (to B7H2), MGA271 (to B7H3), IMP321 (to LAG-3), urelumab/BMS-663513 and PF-05082566 (to CD137/4-1BB), CDX-1127 (to CD27), MEDI-6383 and MEDI-6469 (to OX40), RG-7888 (to OX40L), Atacicept (to TACI), CP-870893 (to CD40), lucatumumab (to CD40), dacetuzumab (to CD40), and muromonab-CD3 (to CD3).

Other molecules that can be combined with the checkpoint regulator antagonists described herein for the treatment of cancer include antagonists of inhibitory receptors on NK cells or agonists of activating receptors on NK cells. For example, antagonist anti-TIGIT, anti-PD-1, and/or anti-PD-L1 antibodies can be combined with antagonists of KIR (e.g., lirilumab), CSF-1R antagonists, such as RG7155.

Tumors evade host immune surveillance by a large variety of mechanisms. Many of these mechanisms may be overcome by the inactivation of immunosuppressive proteins expressed by the tumors. These include among others TGF-.beta., IL-10, and Fas ligand. Antibodies to each of these entities can be used in combination with the checkpoint regulator antagonists described herein to counteract the effects of the immunosuppressive agent and favor tumor immune responses by the host.

Other antibodies that activate host immune responsiveness can be used in combination with the checkpoint regulator antagonists described herein. These include molecules on the surface of dendritic cells that activate DC function and antigen presentation. Anti-CD40 antibodies are able to substitute effectively for T cell helper activity and can be used in conjunction with the checkpoint regulator antagonists described herein. Activating antibodies to T cell costimulatory molecules such as OX-40, CD137/4-1BB, and ICOS may also provide for increased levels of T cell activation.

In certain embodiments, the checkpoint regulator antagonists described herein can be co-administered with one or other more therapeutic agents, e.g., anti-cancer agents, radiotoxic agents or an immunosuppressive agent. Such co-administration can solve problems due to development of resistance to drugs, changes in the antigenicity of the tumor cells that would render them unreactive with the antibody, and toxicities (by administering lower doses of one or more agents).

The checkpoint regulator antagonists described herein can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. The checkpoint regulator antagonists described herein may be co-administered with one or more anti-cancer agents so as to provide two anti-cancer agents operating synergistically via different mechanisms to yield a cytotoxic effect in human cancer cells.

The checkpoint regulator antagonists described herein may be combined with an anti-cancer agent, such an alkylating agent; an anthracycline antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; a phosphatidylinositol-3-kinase (PI3K) inhibitor; an Akt inhibitor; a mammalian target of rapamycin (mTOR) inhibitor; a proteasomal inhibitor; a poly(ADP-ribose) polymerase (PARP) inhibitor; a Ras/MAPK pathway inhibitor; a centrosome declustering agent; a multi-kinase inhibitor; a serine/threonine kinase inhibitor; a tyrosine kinase inhibitor; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue or combination thereof.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary anthracycline antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/odine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Exemplary histone deacetylase inhibitors include, but are not limited to, vorinostat (Zolinza), valproic acid, romidepsin, entinostat abexinostat, givinostat, and mocetinostat.

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary phosphatidyl-inositol-3 kinase (PI3K) inhibitors include wortmannin an irreversible inhibitor of PI3K, demethoxyviridin a derivative of wortmannin, LY294002, a reversible inhibitor of PI3K; BKM120 (Buparlisib); Idelalisib (a PI3K Delta inhibitor); duvelisib (IPI-145, an inhibitor of PI3K delta and gamma); alpelisib (BYL719), an alpha-specific PI3K inhibitor; TGR 1202 (previously known as RP5264), an oral PI3K delta inhibitor; and copanlisib (BAY 80-6946), an inhibitor PI3K$\alpha,\delta$ isoforms predominantly.

Exemplary Akt inhibitors include, but are not limited to miltefosine, AZD5363, GDC-0068, MK2206, Perifosine, RX-0201, PBI-05204, GSK2141795, and SR13668.

Exemplary MTOR inhibitors include, but are not limited to, everolimus (Afinitor) or temsirolimus (Torisel); rapamune, ridaforolimus; deforolimus (AP23573), AZD8055 (AstraZeneca), OSI-027 (OSI), INK-128, BEZ235, PI-103, Torin1, PP242, PP30, Ku-0063794, WAY-600, WYE-687, WYE-354, and CC-223.

Exemplary proteasomal inhibitors include, but are not limited to, bortezomib (PS-341), ixazomib (MLN 2238), MLN 9708, delanzomib (CEP-18770), carfilzomib (PR-171), YU101, oprozomib (ONX-0912), marizomib (NPI-0052), and disufiram.

Exemplary PARP inhibitors include, but are not limited to, olaparib, iniparib, velaparib, BMN-673, BSI-201, AG014699, ABT-888, GPI21016, MK4827, INO-1001, CEP-9722, PJ-34, Tiq-A, Phen, PF-01367338 and combinations thereof.

Exemplary Ras/MAPK pathway inhibitors include, but are not limited to, trametinib, selumetinib, cobimetinib, CI-1040, PD0325901, AS703026, R04987655, R05068760, AZD6244, GSK1120212, TAK-733, U0126, MEK162, and GDC-0973.

Exemplary centrosome declustering agents include, but are not limited to, griseofulvin; noscapine, noscapine derivatives, such as brominated noscapine (e.g., 9-bromonoscapine), reduced bromonoscapine (RBN), N-(3-brormobenzyl) noscapine, aminonoscapine and water-soluble derivatives thereof; CW069; the phenanthridene-derived poly(ADP-ribose) polymerase inhibitor, PJ-34; N2-(3-pyridylmethyl)-5-nitro-2-furamide, N2-(2-thienylmethyl)-5-nitro-2-furamide, and N2-benzyl-5-nitro-2-furamide.

Exemplary multi-kinase inhibitors include, but are not limited to, regorafenib; sorafenib (Nexavar); sunitinib (Sutent); BMW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In certain embodiments, the anti-TIGIT antibodies or anti-TIGIT antibody fragments described herein may be combined with one or more angiogenesis inhibitors. Angiogenesis, the development of new blood vessels from pre-existing vessels, is essential for tumor growth and metastasis. Angiogenesis inhibition presents a potentially valuable strategy for treating diseases, such as cancer, in which progression (e.g., metastasis) is dependent on neovascularization. Two important angiogenesis pathways include the vascular endothelial growth factor (VEGF) pathway and the Tie2 pathway. The principal VEGF pathway is mediated by the transmembrane tyrosine kinase VEGF-R2. Various isoforms of VEGF, particularly VEGF-A, bind to VEGF-R2, resulting in dimerization and activation through phosphorylation of various downstream tyrosine kinases. The Tie2 pathway is another angiogenesis pathway for which therapeutic antibodies and small molecule drugs have been developed. The Tie2 tyrosine kinase receptor activates angiogenesis in response to binding by one its angiopoietin (Ang) ligands (i.e., Ang1, Ang2, Ang3 (mouse) and Ang4). Inhibition of angiogenesis leads to tumor cell death, which may feed tumor antigen into host antigen presentation pathways.

In some embodiments, the subject is administered an anti-TIGIT antibody or HCVR and/or LCVR fragments thereof in combination with one or more VEGF binding antagonists and/or one or more Tie2 receptor binding antagonists. A VEGF binding antagonist binds to VEGF-A or its receptor VEGFR-2 so that, as a result of the binding, activation of VEGFR-2 by VEGF-A is blocked or inhibited. A Tie2 receptor binding antagonist binds to the Tie2 tyrosine kinase receptor or one of its angiopoietin (Ang) ligands (i.e., Ang-1, Ang-2, Ang-3 and Ang-4) so that, as a result of the binding, activation of the Tie2 receptor by one or more of its ligands is blocked or inhibited.

A preferred VEGF antibody antagonist is bevacizumab (AVASTIN™), a humanized antibody. Bevacizumab comprises mutated human IgG1 framework regions and antigen-binding complementarity-determining regions from the murine anti-hVEGF monoclonal antibody A.4.6.1 that blocks binding of human VEGF-A to VEGFR-2. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 Daltons and is glycosylated.

Additional anti-VEGF antibodies include ranibizumab (trade name Lucentis™), a monoclonal antibody fragment derived from the same parent murine antibody as bevacizumab; the G6 or B20 series antibodies (e.g., G6-23, G6-31, B20-4.1) described in U.S. Publication No. 2006/0280747, 2007/0141065 and/or 2007/0020267, as well the antibodies described in U.S. Pat. Nos. 7,060,269, 6,884,879, 6,582,959, 6,703,020; 6,054,297; U.S. Patent Application Publication Nos. U.S. 2007/059312, U.S. 2006/009360, U.S. 2005/0186208, U.S. 2003/0206899, U.S. 2003/0190317, and U.S. 2003/0203409.

An exemplary dominant negative anti-VEGF antagonist is Aflibercept, a recombinant fusion protein containing VEGF-A binding portions from the extracellular domains of human VEGF receptors 1 and 2 fused to the human IgG1 Fc portion. Aflibercept acts as a soluble receptor decoy for VEGF-A.

An exemplary anti-VEGFR-2 antagonist is the humanized IgG1 monoclonal antibody, Ramucirumab, which binds to the extracellular domain of VEGFR-2, thereby blocking its interaction with VEGF-A.

Exemplary small molecule antagonists of the VEGF pathway include multikinase inhibitors of VEGFR-2, including sunitinib, sorafenib, cediranib, pazonpanib and nintedanib.

The Tie2 receptor binding antagonist binds to the Tie2 tyrosine kinase receptor or one of its angiopoietin (Ang) ligands (i.e., Ang-1, Ang-2, Ang-3 and Ang-4) so that, as a result of the binding, activation of the Tie2 receptor by one or more of its ligands is blocked or inhibited. In one embodiment, the Tie2 receptor binding antagonist is an inhibitory peptide. In a specific embodiment, the inhibitory peptide comprises the amino acid sequence in SEQ ID NO: 185, i.e., AQQEECEWDPWTCEHMGSGSATGGSGS-TASSGSGSATHQEECEWDPWTCEHMLE. In another embodiment, the Tie2 receptor binding antagonist comprises the peptide of SEQ ID NO: 93 fused to an Fc fragment, i.e., (SEQ ID NO: 186)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGKGGGGGAQQEECEWDPWTCHEMGS

GSATGGSGSTASSGSGSATHQEECEWDPWTCEHMLE.

Other peptide inhibitors of Tie2 activation (including Ang-2 inhibitors) include A-11 (Compugen), which comprises the amino acid sequence ETFLSTNKLENQ (SEQ ID NO: 187); the CVX-060 peptide (Pfizer); the CVX-037 peptide (Pfizer); and CGEN-25017 (Compugen). Additional peptide inhibitors of Tie2 activation are described in U.S. Pat. No. 7,138,370.

Antibody inhibitors of Tie2 activation (and/or angiopoietin-2) include AMG-780 (Amgen), MEDI-3617 (MedImmune/AstraZeneca), DX-2240 (Dyax/Sanofi-Aventis), REGN-910 (Sanofi/Regeneron), RG7594 (Roche), LCO6 (Roche), TAvi6 (Roche), AT-006 (Roche/Affitech). Additional Tie2 receptor binding antibody antagonists and antibody binding sequences therefrom are described in U.S. Pat.

Nos. 7,521,053, 7,658,924, and 8,030,025, as well as U.S. Patent Application Publication Nos. 2013/0078248, 2013/0259859, and 2015/0197578.

Tie2 binding antagonists also include the small molecule inhibitors, CGI-1842 (CGI Pharmaceuticals), LP-590 (Locus Pharmaceuticals), ACTB-1003 (Act Biotech/Bayer AG), CEP-11981 (Cephalon/Teva), MGCD265 (Methylgene), Regorafenib (Bayer), Cabozantinib/XL-184/BMS-907351 (Exelixis), Foretnib (Exelixis), MGCD-265 (MethylGene Inc.).

In certain embodiments, the checkpoint regulator antagonists described herein are administered at a subtherapeutic dose, another anti-immune checkpoint regulator antibody or antagonist is administered at a subtherapeutic dose, the angiogenesis antagonist is administered at a subtherapeutic dose, or any antagonist in a combination thereof is each administered at a subtherapeutic dose.

In certain embodiments, TIGIT, PD-1 and/or PD-L1 inhibition is combined with standard cancer treatments (e.g., surgery, radiation, and chemotherapy). TIGIT, PD-1 and/or PD-L1 inhibition can be effectively combined with chemotherapeutic regimes. In these instances, it may be possible to reduce the dose of chemotherapeutic reagent administered. An example of such a combination is an anti-TIGIT, anti-PD-1 or anti-PD-L1 antibody in combination with decarbazine for the treatment of melanoma. Another example of such a combination is an anti-TIGIT, anti-PD-1 or anti-PD-L1 antibody in combination with interleukin-2 (IL-2) for the treatment of melanoma. It is believed that the combined use of TIGIT, PD-1 and/or PD-L1 inhibition and chemotherapy can enhance apoptosis and increase tumor antigen presentation for cytotoxic immunity. Other synergistic combination therapies include TIGIT, PD-1 and/or PD-L1 inhibition through cell death when used in combination with radiation, surgery or hormone deprivation. Each of these protocols creates a source of tumor antigen in the host.

In certain embodiment, the checkpoint regulator antagonists described herein can also be used in multi-specific antagonists or in combination with bispecific antibodies targeting Fcα. or Fcγ receptor-expressing effector cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to cancer cells or tumors. This targeting may more effectively activate tumor specific responses. The T cell arm of these responses would be augmented by the inhibition of TIGIT, PD-1 and/or PD-L1. Alternatively, antigen may be delivered directly to DCs by the use of bispecific antibodies that bind to tumor antigen and a dendritic cell specific cell surface marker.

Nucleic Acids and Host Cells for Expressing Checkpoint Regulator Antagonist

In another aspect, the present application provides nucleic acids encoding the checkpoint regulator antagonist of the present application, and expression vectors comprising such nucleic acids. In some embodiments, nucleic acids encodes an HCVR and/or LCVR fragment of an antibody or fragment in accordance with the embodiments described herein, or any of the other antibodies and antibody fragments described herein.

DNA encoding an antigen binding site in a monoclonal antibody can be isolated and sequenced from the hybridoma cells using conventional procedures (e.g., by using oligonucleotide probes that are capable of binding specifically to genes encoding the heavy and light chains of the monoclonal antibodies). Alternatively, amino acid sequences from immunoglobulins of interest may be determined by direct protein sequencing, and suitable encoding nucleotide sequences can be designed according to a universal codon table. In other cases, nucleotide and amino acid sequences of antigen binding sites or other immunoglobulin sequences, including constant regions, hinge regions and the like may be obtained from published sources well known in the art.

Expression vectors encoding a particular monospecific, bispecific or trispecific checkpoint regulator antagonist may be used to synthesize the checkpoint regulator antagonists of the present disclosure in cultured cells in vitro or they may be directly administered to a patient to express the checkpoint regulator antagonist in vivo or ex vivo. As used herein, an "expression vector" refers to a viral or non-viral vector comprising a polynucleotide encoding one or more polypeptide chains corresponding to the monospecific, bispecific or trispecific checkpoint regulator antagonists of the present disclosure in a form suitable for expression from the polynucleotide(s) in a host cell for antibody preparation purposes or for direct administration as a therapeutic agent.

A nucleic acid sequence is "operably linked" to another nucleic acid sequence when the former is placed into a functional relationship with the latter. For example, a DNA for a presequence or signal peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a signal peptide, contiguous and in reading phase. However, enhancers do not have to be contiguous. Linking is accomplished by ligation at convenient restriction sites. If such sites do not exist, synthetic oligonucleotide adaptors or linkers may be used in accordance with conventional practice.

Nucleic acid sequences for expressing the checkpoint regulator antagonists typically include an amino terminal signal peptide sequence, which is removed from the mature protein. Since the signal peptide sequences can affect the levels of expression, the polynucleotides may encode any one of a variety of different N-terminal signal peptide sequences. It will be appreciated by those skilled in the art that the design of the expression vector can depend on such factors as the choice of the host cell to be transformed, the level of expression of protein desired, and the like.

The above described "regulatory sequences" refer to DNA sequences necessary for the expression of an operably linked coding sequence in one or more host organisms. The term "regulatory sequences" is intended to include promoters, enhancers and other expression control elements (e.g., polyadenylation signals). Regulatory sequences include those which direct constitutive expression of a nucleotide sequence in many types of host cells or those which direct expression of the nucleotide sequence only in certain host cells (e.g., tissue-specific regulatory sequences). Expression vectors generally contain sequences for transcriptional termination, and may additionally contain one or more elements positively affecting mRNA stability.

The expression vector contains one or more transcriptional regulatory elements, including promoters and/or enhancers, for directing the expression of checkpoint regulator antagonists. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. A promoter may contain a genomic fragment or it may contain a chimera of one or more TREs combined together.

Preferred promoters are those capable of directing high-level expression in a target cell of interest. The promoters may include constitutive promoters (e.g., HCMV, SV40, elongation factor-1.alpha. (EF-1.alpha.)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the antibody producing cell. Cell or tissue-specific transcriptional regulatory elements (TREs) can be incorporated into expression vectors to restrict expression to desired cell types. Pol III promoters (H1 or U6) are particularly useful for expressing shRNAs from which siRNAs are expressed. An expression vector may be designed to facilitate expression of the checkpoint regulator antagonist in one or more cell types.

In certain embodiments, one or more expression vectors may be engineered to express both the checkpoint regulator antagonist and one or more siRNA targeting the Tie2 pathway, the VEGF pathway or an immune checkpoint regulator.

An siRNA is a double-stranded RNA that can be engineered to induce sequence-specific post-transcriptional gene silencing of mRNAs. Synthetically produced siRNAs structurally mimic the types of siRNAs normally processed in cells by the enzyme Dicer. When expressed from an expression vector, the expression vector is engineered to transcribe a short double-stranded hairpin-like RNA (shRNA) that is processed into a targeted siRNA inside the cell. Synthetic siRNAs and shRNAs may be designed using well known algorithms and synthesized using a conventional DNA/RNA synthesizer.

To co-express the individual chains of the checkpoint regulator antagonist, a suitable splice donor and splice acceptor sequences may be incorporated for expressing both products. Alternatively, an internal ribosome binding sequence (IRES) or a 2A peptide sequence, may be employed for expressing multiple products from one promoter. An IRES provides a structure to which the ribosome can bind that does not need to be at the 5' end of the mRNA. It can therefore direct a ribosome to initiate translation at a second initiation codon within a mRNA, allowing more than one polypeptide to be produced from a single mRNA. A 2A peptide contains short sequences mediating co-translational self-cleavage of the peptides upstream and downstream from the 2A site, allowing production of two different proteins from a single transcript in equimolar amounts. CHYSEL is a non-limiting example of a 2A peptide, which causes a translating eukaryotic ribosome to release the growing polypeptide chain that it is synthesizing without dissociating from the mRNA. The ribosome continues translating, thereby producing a second polypeptide.

An expression vector may comprise a viral vector or a non-viral vector. A viral vectors may be derived from an adeno-associated virus (AAV), adenovirus, herpesvirus, vaccinia virus, poliovirus, poxvirus, a retrovirus (including a lentivirus, such as HIV-1 and HIV-2), Sindbis and other RNA viruses, alphavirus, astrovirus, coronavirus, orthomyxovirus, papovavirus, paramyxovirus, parvovirus, picornavirus, togaviruses and the like. A non-viral vector is simply a "naked" expression vector that is not packaged with virally derived components (e.g., capsids and/or envelopes).

In certain cases, these vectors may be engineered to target certain diseases or cell populations by using the targeting characteristics inherent to the virus vector or engineered into the virus vector. Specific cells may be "targeted" for delivery of polynucleotides, as well as expression. Thus, the term "targeting", in this case, may be based on the use of endogenous or heterologous binding agents in the form of capsids, envelope proteins, antibodies for delivery to specific cells, the use of tissue-specific regulatory elements for restricting expression to specific subset(s) of cells, or both.

In some embodiments, expression of the antibody chains is under the control of the regulatory element such as a tissue specific or ubiquitous promoter. In some embodiments, a ubiquitous promoter such as a CMV promoter, CMV-chicken beta-actin hybrid (CAG) promoter, a tissue specific or tumor-specific promoter to control the expression of a particular antibody heavy or light chain or single-chain derivative therefrom.

Non-viral expression vectors can be utilized for non-viral gene transfer, either by direct injection of naked DNA or by encapsulating the checkpoint regulator antagonist-encoding polynucleotides in liposomes, microparticles, microcapsules, virus-like particles, or erythrocyte ghosts. Such compositions can be further linked by chemical conjugation to targeting domains to facilitate targeted delivery and/or entry of nucleic acids into desired cells of interest. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin.

Alternatively, naked DNA may be employed. Uptake efficiency of naked DNA may be improved by compaction or by using biodegradable latex beads. Such delivery may be improved further by treating the beads to increase hydrophobicity and thereby facilitate disruption of the endosome and release of the DNA into the cytoplasm.

Methods for Producing Monospecific or Multispecific Antibodies

In another aspect, the present application provides host cells transformed with the anti-TIGIT, anti-PD-1 and/or anti-PD-L1 HCVRs and/or LCVRs encoding nucleic acids or expression vectors. The host cells can be any bacterial or eukaryotic cell capable of expressing the anti-TIGIT, anti-PD-1 and/or anti-PD-L1 HCVRs and/or LCVRs encoding nucleic acids or expression vectors or any of the other co-administered antibodies or antagonists described herein.

In another aspect, a method of producing a checkpoint regulator antagonist comprises culturing a host cell transformed with one or more anti-TIGIT, anti-PD-1 and/or anti-PD-L1 HCVRs and/or LCVRs encoding nucleic acids or expression vectors under conditions that allows production of the antibody or fragment, and purifying the antibody from the cell.

In a further aspect, the present application provides a method for producing an antibody comprising culturing a cell transiently or stably expressing one or more constructs encoding one or more polypeptide chains in the antibody; and purifying the antibody from the cultured cells. Any cell capable of producing a functional antibody may be used. In preferred embodiments, the antibody-expressing cell is of eukaryotic or mammalian origin, preferably a human cell. Cells from various tissue cell types may be used to express the antibodies. In other embodiments, the cell is a yeast cell, an insect cell or a bacterial cell. Preferably, the antibody-producing cell is stably transformed with a vector expressing the antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the antibody along with a selectable marker facilitating selection of stably transformed clones expressing the antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR$^-$ cells and mouse LTV cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In one embodiment, the cell line comprises a stably transformed *Leishmania* cell line, such as *Leishmania tarentolae*. *Leishmania* are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

In some embodiments, the cell lines expresses at least 1 mg, at least 2 mg, at least 5 mg, at least 10 mg, at least 20 mg, at least 50 mg, or at least 100 mg of the antibody/liter of culture.

The antibodies in the present application may be isolated from antibody expressing cells following culture and maintenance in any appropriate culture medium, such as RPMI, DMEM, and AIM V®. The antibodies can be purified using conventional protein purification methodologies (e.g., affinity purification, chromatography, etc.), including the use of Protein-A or Protein-G immunoaffinity purification. In some embodiments, antibodies are engineered for secretion into culture supernatants for isolation therefrom.

Pharmaceutical Compositions and Methods of Treatment

Another aspect of the present application relates to pharmaceutical compositions and methods for treating a cell proliferative disorder, such as cancer, chronic infections, or immunologically compromised disease states. In one embodiment, the pharmaceutical composition comprises a checkpoint regulator antagonist of the present application. In some embodiments, the checkpoint regulator antagonist comprises an anti-TIGIT antibody, an anti-PD-1 antibody, an anti-PD-L1 antibody, a bispecific checkpoint regulator antagonist, a trispecific checkpoint regulator antagonist, or an antigen-binding fragment thereof as described herein, formulated together with a pharmaceutically acceptable carrier. Such compositions may include one or more different antibodies, one or more multispecific antibodies, one or more immunoconjugates, or a combination thereof as described herein.

As described above, methods for using the pharmaceutical compositions described herein comprise administering to a subject in need thereof an effective amount of the pharmaceutical composition according to the present disclosure.

Any suitable route or mode of administration can be employed for providing the patient with a therapeutically or prophylactically effective dose of the antibody or antagonist. Exemplary routes or modes of administration include parenteral (e.g., intravenous, intraarterial, intramuscular, subcutaneous, intratumoral), oral, topical (nasal, transdermal, intradermal or intraocular), mucosal (e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising an antibody or antagonist in accordance with the present disclosure may be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions may comprise suitable solid or gel phase carriers or excipients. Exemplary carriers or excipients include but are not limited to, calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agents.

The checkpoint regulator antagonist can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

Therapeutic checkpoint regulator antagonist preparations can be lyophilized and stored as sterile powders, preferably under vacuum, and then reconstituted in bacteriostatic water (containing, for example, benzyl alcohol preservative) or in sterile water prior to injection. Pharmaceutical composition may be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the checkpoint regulator antagonist to elicit a desired response in the individual, previous therapy, the age, weight and sex of the patient, the patient's clinical history and response to the antibody, the type of the checkpoint regulator antagonist used, discretion of the attending physician, etc. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the checkpoint regulator antagonist are derived from the same host in which they are to be administered in order to reduce inflammatory responses against the administered therapeutic agents.

The checkpoint regulator antagonist is suitably administered to the patent at one time or over a series of treatments and may be administered to the patient at any time from diagnosis onwards. The checkpoint regulator antagonist may be administered as the sole treatment or in conjunction with other drugs or therapies useful in treating the condition in question.

As a general proposition, a therapeutically effective amount or prophylactically effective amount of the checkpoint regulator antagonist will be administered in a range from about 1 ng/kg body weight/day to about 100 mg/kg body weight/day whether by one or more administrations. In a particular embodiment, each checkpoint regulator antagonist is administered in the range of from about 1 ng/kg body weight/day to about 10 mg/kg body weight/day, about 1 ng/kg body weight/day to about 1 mg/kg body weight/day, about 1 ng/kg body weight/day to about 100 µg/kg body weight/day, about 1 ng/kg body weight/day to about 10 µg/kg body weight/day, about 1 ng/kg body weight/day to about 1 µg/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 µg/kg body weight/day, about 10 ng/kg body weight/day to about 10 µg/kg body weight/day, about 10 ng/kg body weight/day to about 1 µg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 µg/kg body weight/day, about 100 ng/kg body weight/day to about 10 µg/kg body weight/day, about 100 ng/kg body weight/day to about 1 µg/kg body weight/day, about 1 µg/kg body weight/day to about 100 mg/kg body weight/day, about 1 µg/kg body weight/day to about 10 mg/kg body weight/day, about 1 µg/kg body weight/day to about 1 mg/kg body weight/day, about 1 µg/kg body weight/day to about 100 µg/kg body weight/day, about 1 µg/kg body weight/day to about 10 µg/kg body weight/day, about 10 µg/kg body weight/day to about 100 mg/kg body weight/day, about 10 µg/kg body weight/day to about 10 mg/kg body weight/day, about 10 µg/kg body weight/day to about 1 mg/kg body weight/day, about 10 µg/kg body weight/day to about 100 µg/kg body weight/day, about 100 µg/kg body weight/day to about 100 mg/kg body weight/day, about 100 µg/kg body weight/day to about 10 mg/kg body weight/day, about 100 µg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the checkpoint regulator antagonist is administered at a dose of 500 µg to 20 g every three days, or 25 mg/kg body weight every three days.

In other embodiments, each checkpoint regulator antagonist is administered in the range of about 10 ng to about 100 ng per individual administration, about 10 ng to about 1 µg per individual administration, about 10 ng to about 10 µg per individual administration, about 10 ng to about 100 µs per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 µg per individual administration, about 100 ng to about 10 µg per individual administration, about 100 ng to about 100 µg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 µg to about 10 µg per individual administration, about 1 µg to about 100 µg per individual administration, about 1 µg to about 1 mg per individual administration, about 1 µg to about 10 mg per individual administration, about 1 µg to about 100 mg per individual administration, about 1 µg to about 1000 mg per injection, about 1 µg to about 10,000 mg per individual administration, about 10 µg to about 100 µg per individual administration, about 10 µg to about 1 mg per individual administration, about 10 µg to about 10 mg per individual administration, about 10 µg to about 100 mg per individual administration, about 10 µg to about 1000 mg per injection, about 10 µg to about 10,000 mg per individual administration, about 100 µg to about 1 mg per individual administration, about 100 µg to about 10 mg per individual administration, about 100 µg to about 100 mg per individual administration, about 100 µg to about 1000 mg per injection, about 100 µg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The checkpoint regulator antagonist may be administered daily, every 2, 3, 4, 5, 6 or 7 days, or every 1, 2, 3 or 4 weeks.

In other particular embodiments, the amount of the checkpoint regulator antagonist may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for a checkpoint regulator antagonist are incorporated into a suitable expression vector (e.g., viral or non-viral vector) for expressing an effective amount of the checkpoint regulator antagonist in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

The present invention is further illustrated by the following examples which should not be construed as limiting. The contents of all references, patents and published patent applications cited throughout this application, as well as the Figures and Tables are incorporated herein by reference.

EXAMPLES

Example 1: Generation of Monoclonal Antibodies

Monoclonal antibodies (mAbs) of the present application are generated and screened using techniques well known in the art, see, e.g., Harlow and Lane (1988) Antibodies, A Laboratory Manual, Cold Spring Harbor Publications, New York. The antigen specific hybridoma mabs are cloned, sequenced and engineered using techniques well known in the art, see e.g., Lo. B. K. C Methods in Molecular Biology™. Volume 248 2004. Antibody Engineering.

Example 2: TIGIT Binder Screening Assay

1 µg/ml TIGIT-His protein was coated overnight at 4° C. and blocked with 1% BSA in PBS for 1 hour at room temperature and then incubated with 50 µl hybridoma supernatant for 1 hour at room temperature, mouse IgG was detected by anti-mouse IgG HRP for 30 mins, TMB substrate was then added and reaction was stopped by adding a 2N $H_2SO_4$ solution. Wells with OD values at least five times over the background were selected as positive binders.

Example 3: TIGIT Blocker Screening Assay $3 \times 10^4$ TIGIT+CHO-K1 cells were incubated in 50 ul hybridoma supernatant for 20 mins at 4° C. and then human PVR human Fc tag fusion protein was added to a final concentration of 0.6 µ/ml; after 30 mins incubation at 4° C., cells were washed with FACS buffer (0.5% BSA, 2 mM EMTA in PBS) and then cells were incubated with 1 µg/ml PE labeled anti-human Fc antibody for 20 mins at 4° C. Cells were then washed with FACS buffer and then resuspended in 7-amino-actinomycin D (7AAD) solution before analysis with iQue intellicyt system. Wells that completely blocked TIGIT and PVR (Fc tag) binding were selected as blockers. In the first screening, 18 blockers were identified out of 65 binders. In the second screening, 17 blockers were identified out of 30 binders. FIG. 1 shows exemplary results of a competition assay of various mouse anti-TIGIT mabs.

Example 4: Anti-TIGIT Mab Blocking/IC50 Assay

CHO-K1 cells stably expressing human TIGIT were washed with FACS buffer (0.5% BSA, 2 mM EMTA in PBS) and resuspended at a concentration of 10 6 cells/ml. Biotinylated hPVR-mIg (Cat #:555-030, Ancell) was added to the resuspended cells at 1 µg/ml; mixed well; without incubation, 20,000 of these CHO-K1 cell (with human CD155/PVR protein) in 20 µl FACS buffer to 96-well round bottom plates; 20 µl 2-fold serial dilutions of anti-human TIGIT mab was added to the cells and incubated at 4 C for 30 min. The cells were washed 2 times before staining with PE streptavidin (BioLegend) for 20 min at 4 C. The cells were then washed, resuspended in 30 µl 7 AAD solution, and 35 µl of 10% neutral buffered formalin solution was added. The cells were then incubated for 15 min. Flow cytometry was performed and IC50 was calculated using iQue intellicyt system. Table 2 shows the IC50 of various anti-hu TIGIT mabs. Table 3 shows binding constants for several anti-hu TIGIT mabs.

TABLE 2

| Antibody | IC50 (nM) |
| --- | --- |
| T-01 | 0.29-0.56 |
| T-02 | 0.35-0.71 |
| T-03 | 0.26-0.52 |
| T-04 | 0.12-0.31 |
| T-05 | 0.20-0.46 |
| T-06 | 0.84 |
| T-07 | 0.50 |
| T-08 | 0.40-1.67 |
| T-09 | 0.36-0.42 |
| T-10 | 0.10-0.63 |

TABLE 3

| mAb | Binding Affinity | | |
| --- | --- | --- | --- |
| | $K_D$ (nM) | $K_a$ (M$^{-1}$ s$^{-1}$) | Kd (s$^{-1}$) |
| T-10 | 2.01 | 8.56E+05 | 1.72E-03 |
| T-04 | 0.67 | 8.09E+05 | 5.38E-04 |
| T-08 | 5.44 | 6.90E+05 | 3.76E-03 |
| BM | 22 | 9.71E+05 | 2.13E-02 |

Example 5: Anti-TIGIT Mabs Binding Assay

Figure 6:
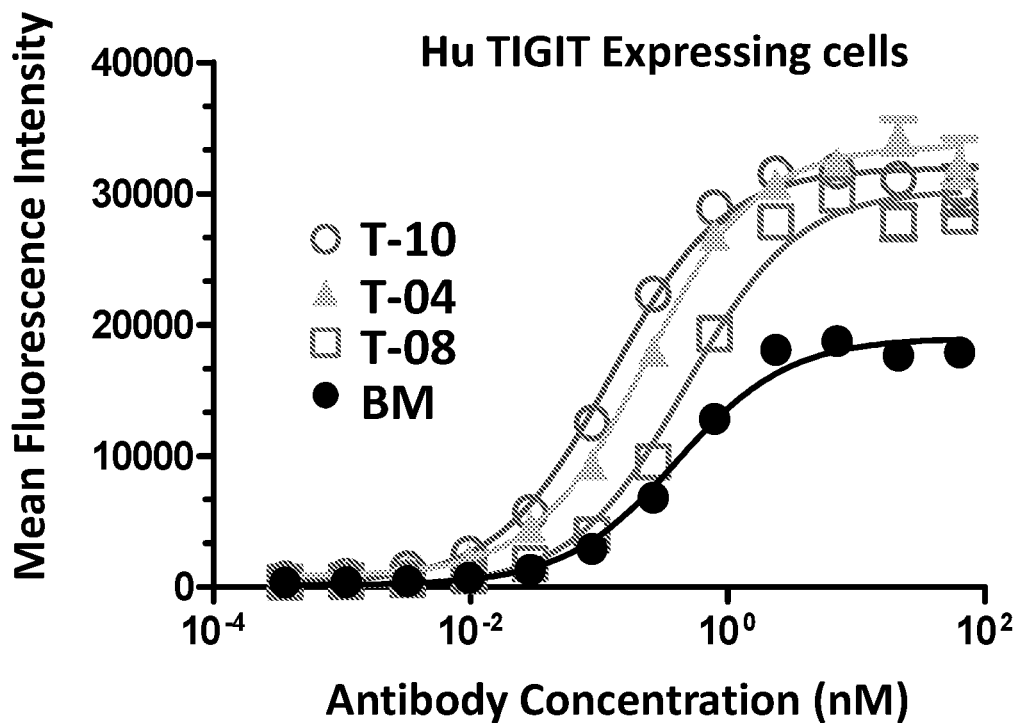
FIG. 6 depicts the binding of anti-TIGIT mouse mabs to cells expressing full-length human TIGIT (hu TIGIT).

FIG. 6 shows the binding of anti-TIGIT mouse mabs to cells expressing full-length human TIGIT (hu TIGIT). Briefly, serial dilutions of anti-TIGIT mabs were added to CHO-K1 cells (20,000 cells/well) overexpressing human or cyno TIGIT. The mixtures were incubated at 4 C for 20 min and washed 3 times. The mixtures were stained with the secondary antibody, PE labeled F(ab')2-Goat anti-human IgG Fc (Thermo H10104) at 4° C. for 20 min. Cells were washed and resuspended in 7AAD solution and fixed in 10% neutral buffered formalin solution for 15 minutes before analysis with the iQue Intellicyt system.

Figure 7:
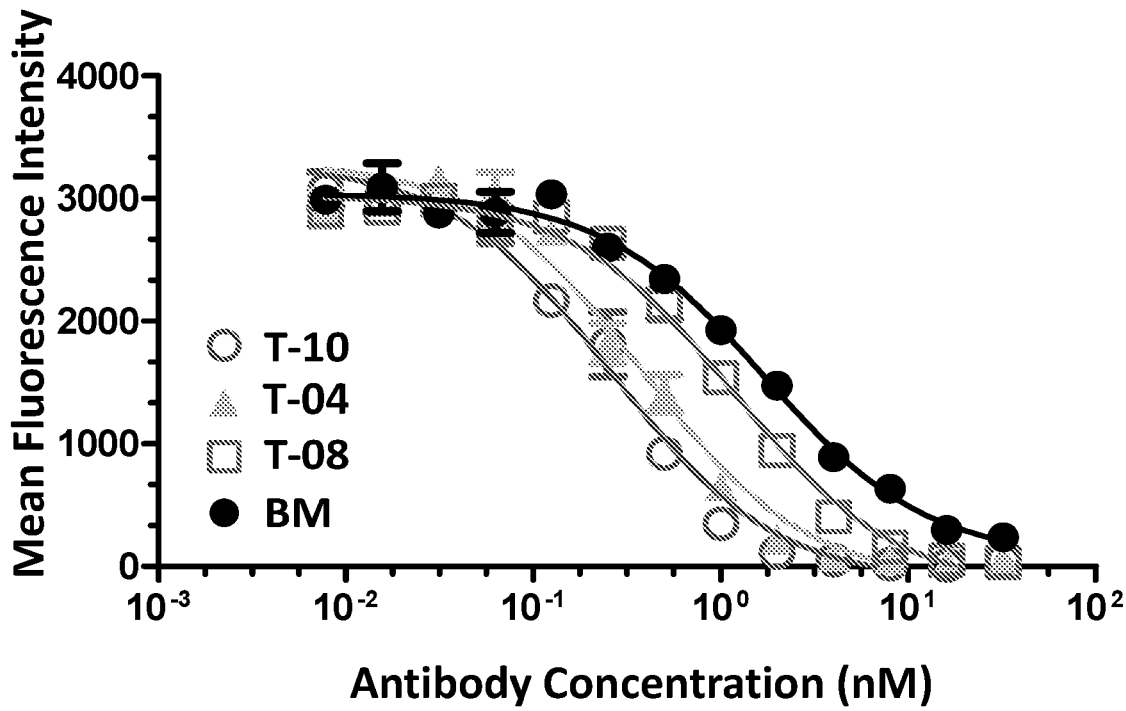
FIG. 7 shows that anti-TIGIT mabs block the interaction between hu TIGIT and its ligand, human PVR (CD155) in a cell-based assay.

Example 6: Anti-TIGIT Mabs Block the Interaction Between Hu TIGIT and its Ligand Using the cell-based blocking assay described in Example 4, anti-TIGIT mabs were evaluated for their ability to block the interaction between hu TIGIT and its ligand, human PVR (CD155). The results of this assay are shown in FIG. 7.

Example 7: Human T Cell Assay with PBMC from Normal Donor and PVR Signal from Pre-Coated PVR-mIgG Two human T cell assays were performed to show the functionality of the anti-TIGIT antibodies. Briefly, normal healthy human PBMC were activated with SEB (Toxin Technology, Cat #: BT202) or anti-CD3+Anti-CD28 for 5 to 7 days in 6-well plates with PBMCs expressing high levels of TIGIT. 96-well flat-bottom plates were coated with huPVR/CD155 Mouse IgG2a Fc Tag (ACRO Biosystems) overnight at 4° C.

Figure 8:
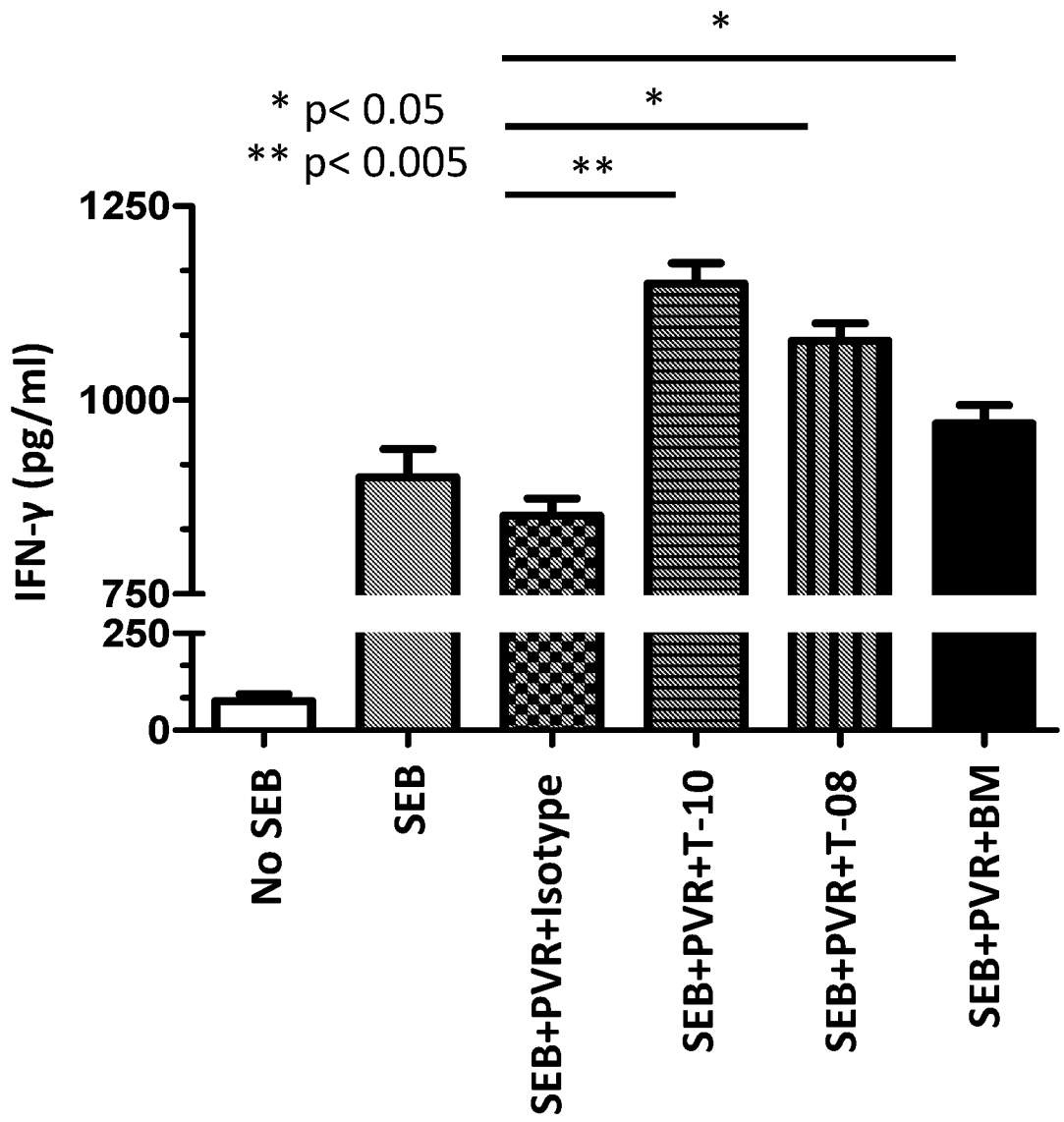
FIG. 8 shows the enhancement of IFN-γ production from human PBMCs by anti-TIGIT mabs.

To assay for IFN-γ production, 100,000 cells were plated into the pre-coated wells and re-stimulated with 0.5 ug/ml Staphylococcal enterotoxin B (SEB). 66 µg/ml of anti-TIGIT mAbs or isotype control Ab was added. 3 to 5 days later, the supernatant was examined for IFN-γ by ELISA. FIG. 8 shows that the anti-TIGIT mabs induced IFN-γ production from the human PBMCs.

Figure 9:
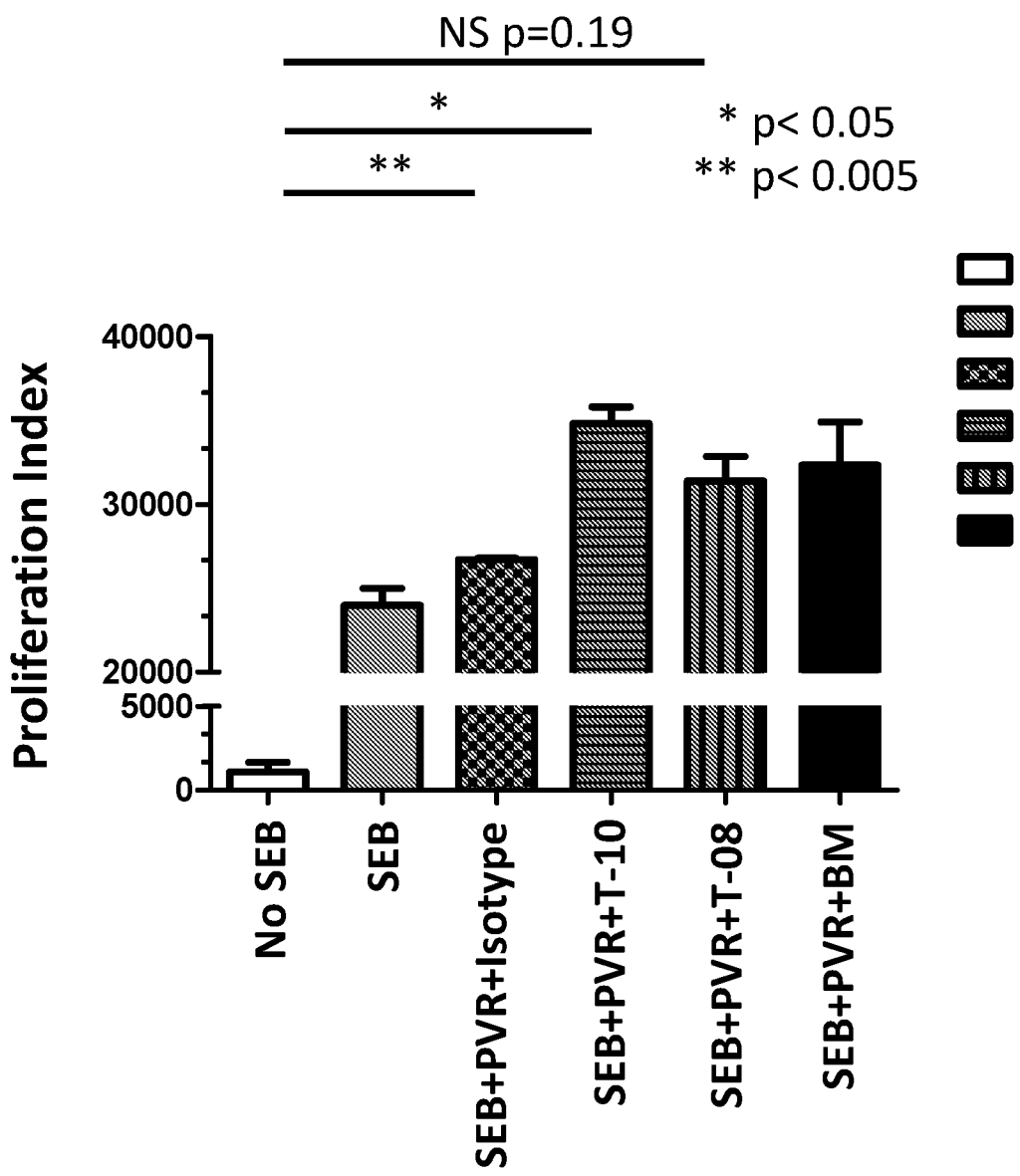
FIG. 9 shows the enhancement of primary human T cell proliferation by anti-TIGIT mabs.

To assay for T cell proliferation, CellTrace Far Red labeled 100,000 cells were plated into the pre-coated wells and re-stimulated with 0.5 ug/ml SEB. 66 ug/ml of anti-TIGIT or an isotype-matched control antibody were added into wells with coated human CD155/PVR. Total volume per well was 200 µl. The plates were incubated at 37° C. At 4 or 5 days post stimulation, PBMC cells were stained with FITC labeled anti-human CD3 Ab (BioLegend) and analyzed using the iQue intellicyt system. T cell proliferation indices were calculated based on the reduction of MFI (Mean Fluorescence Intensity) of CellTrace Far Red signal on gated CD3+ T cells. As shown in FIG. 9, the results from this assay showed that the anti-TIGIT mabs induced the proliferation of T cells.

Example 8: Binding of Anti-TIGIT Mabs to Hu TIGIT- and Cyno-Hu TIGIT

Figure 10A:
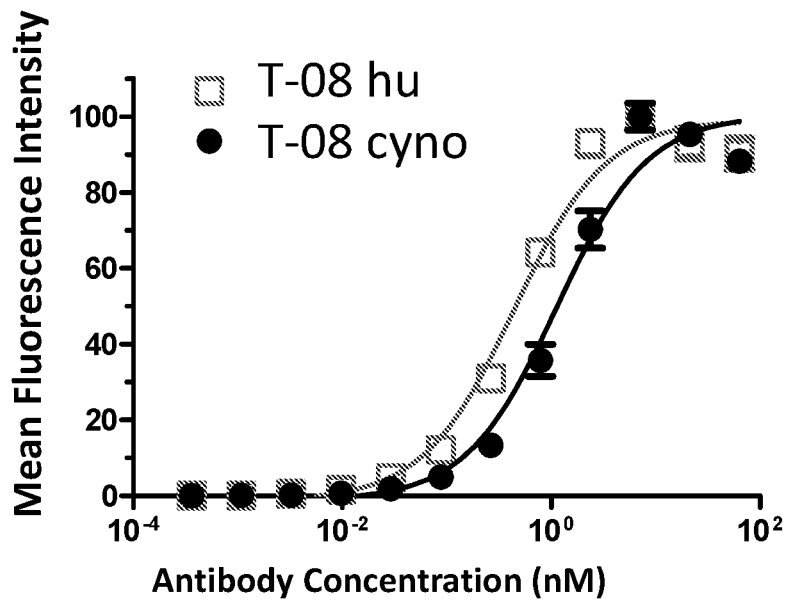
FIG. 10A shows binding of anti-TIGIT mabs to hu TIGIT- and cyno-hu TIGIT in cell based assays.
Figure 10B:
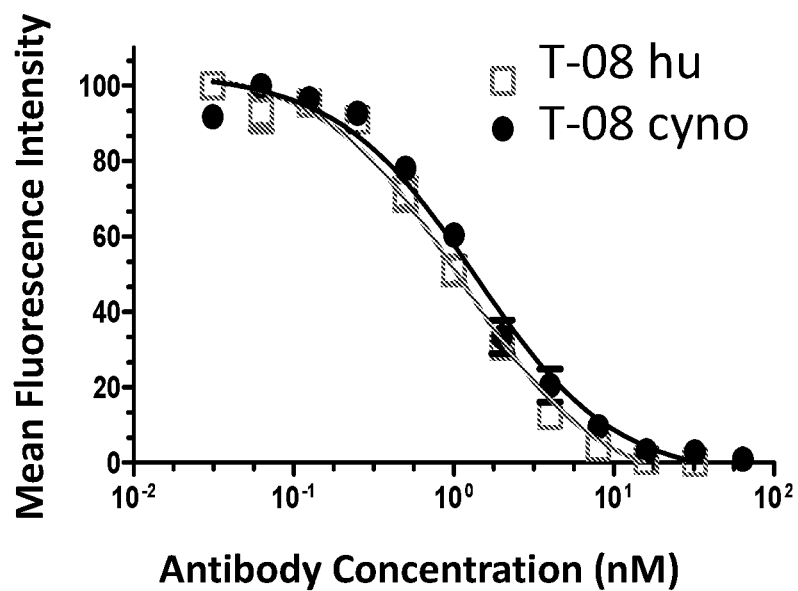
FIG. 10B shows inhibition of antibody binding to hu TIGIT- and cyno-hu TIGIT by anti-TIGIT mabs in cell based assays.

FIG. 10A shows binding of anti-TIGIT mabs to hu TIGIT- and cyno-hu TIGIT using the binding assay described in Example 5. FIG. 10B shows inhibition of antibody binding to hu TIGIT- and cyno-hu TIGIT by anti-TIGIT mabs using the blocking assay described in Example 4.

Example 9: PD-1 Binder Screening Assay

1 µg/ml huPD-1-His protein was coated in wells overnight at 4° C. and blocked with 1% BSA in PBS for 1 hour at room temperature and then incubated with 50 µl hybridoma supernatant for 1 hour at room temperature. Mouse IgG was detected by incubating the wells with anti-mouse IgG HRP for 30 mins, adding TMB substrate, and stopping the reaction with 2N sulfuric acid solution. Wells with OD450 value at least five times over the background were selected as positive binders.

Example 10: PD-1 Blocker Screening Assay

3×10$^4$ huPD1+CHO-K1 cells were incubated in 50 µl hybridoma supernatant for 20 mins at 4° C. and then human PD-L1 human Fc tag fusion protein was added to a final concentration of 0.6 µg/ml. After a 30 min incubation at 4° C., the cells were washed with FACS buffer (0.5% BSA, 2 mM EMTA in PBS) and then incubated with 1 µg/ml PE labeled anti-human Fc antibody for 20 mins at 4° C. Cells were then washed with FACS buffer and then re-suspended in 7AAD solution before analysis with iQue intellicyt system. Wells that completely blocked PD-1 and PD-L1 (Fc tag) binding were selected as blockers.

Example 11: Anti-PD-1 Mab Blocking/IC50 Assay

Figure 11A:
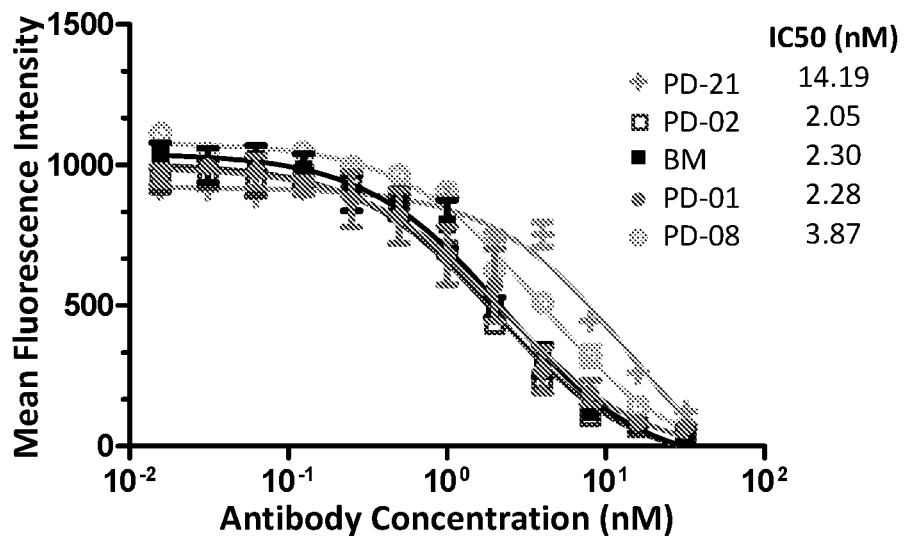
FIG. 11A shows that anti-PD-1 mabs block the interaction between human PD-1 and human PD-L1.
Figure 11B:
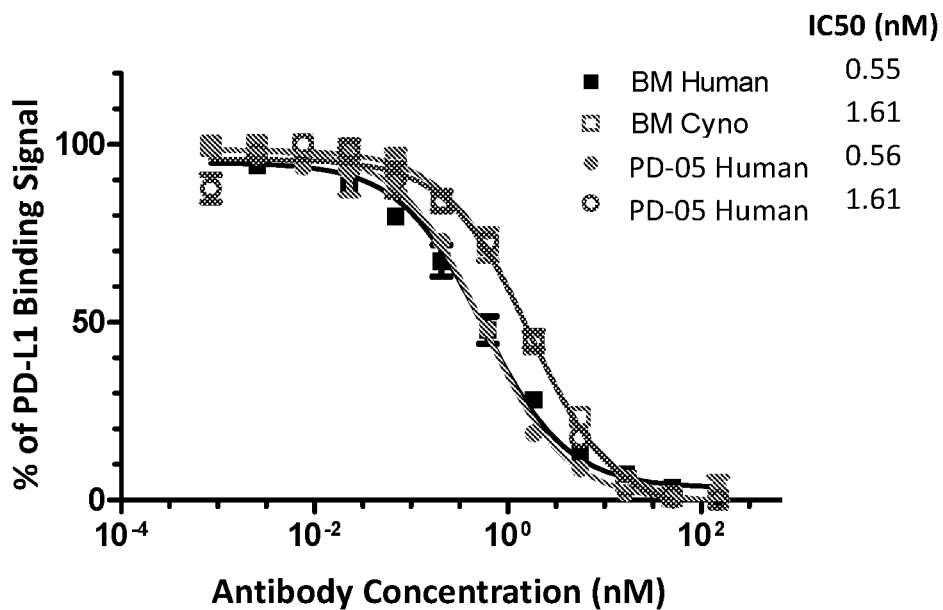
FIG. 11B shows that anti-PD-1 mabs block the interaction between cyno hu PD-1 and cyno PD-L1.
Figure 12A:
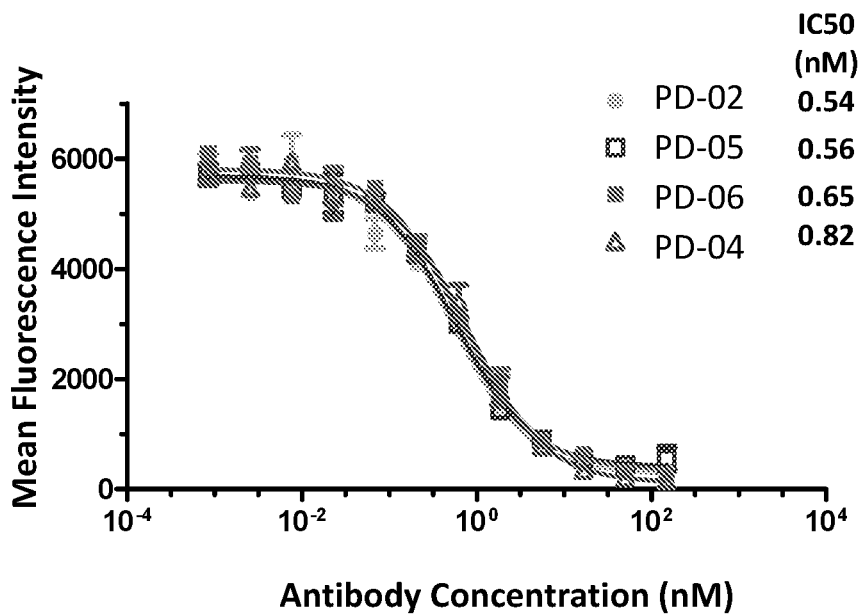
FIG. 12A shows the binding of anti-PD-1 mabs to hu PD-L1.
Figure 12B:
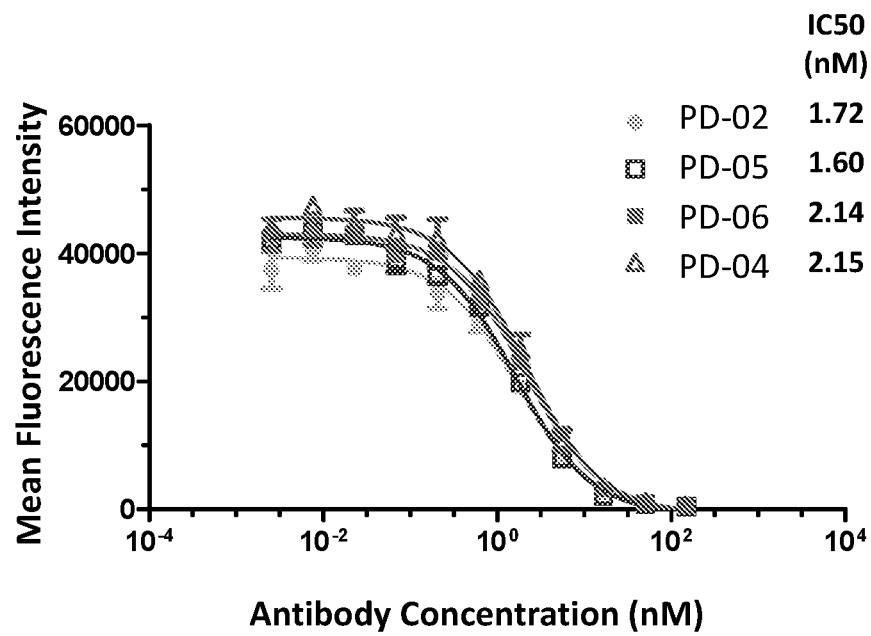
FIG. 12B shows the binding of anti-PD-1 mabs to cyno-hu PD-L1.

A blocking assay was carried out to calculate the IC50 for selected anti-PD-1 antibodies. Briefly, 2 or 3 fold serial dilutions of anti-human PD-1 mAb or bispecific Ab (Highest Ab concentration: 128 nM; Triplicates for each mAb) were prepared. Human or Cyno PD-1 transfected CHO-K1 cells were washed with FACS buffer (0.5% BSA 2 mM EDTA in PBS) and re-suspended at a concentration of 10$^6$ cells/ml. FITC labeled human PD-L1-Fc protein was added to the human or cyno PD-1 transfected CHO-K1 cells at a final concentration of 7 µg/ml and mixed well. Without incubation, 2,000 of these CHO-K1 cells (with PD-L1 Protein) in 20 µl FACS buffer was immediately added to a 96-well round bottom plate and 20 µl or 2 or 3 fold serial diluted anti-human PD-1 mAbs were immediately added to the cells and incubated at 4° C. for 30 mins. The cells were then washed and re-suspended in 30 µl 7 AAD solution; 35 µl 10% neutral buffered formalin solution was then added and incubated for 15 mins. before analysis using the iQue intellicyt system. FIGS. 11A, 12A and 12B show the results demonstrating the ability of several anti-PD-1 mabs to block the interaction between human PD-1 and human PD-L1. FIG. 11B shows the ability of anti-PD-1 mabs to block the interaction between cyno hu PD-1 and cyno PD-L1.

Example 12: Anti-PD-1 Antibody/Kinetic Analysis by Bio-Layer Interferometry

Figure 13A:
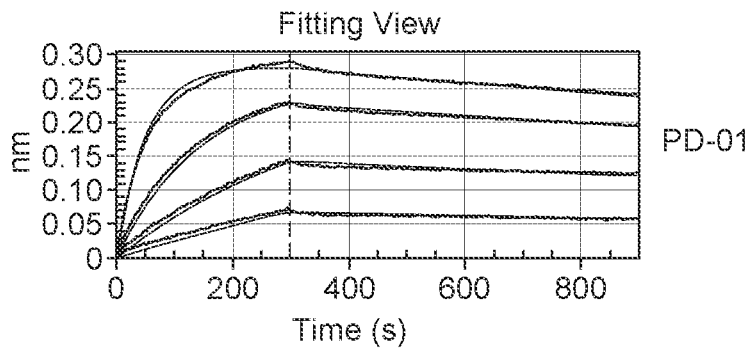
FIGS. 13A-C shows the binding affinity of anti-PD-1 antibodies to human PD-1, including PD-01 mab (FIG. 13A), PD-02 mab (FIG. 13B) and a benchmark (BM) anti-PD-1 mab (FIG. 13C).
Figure 13B:
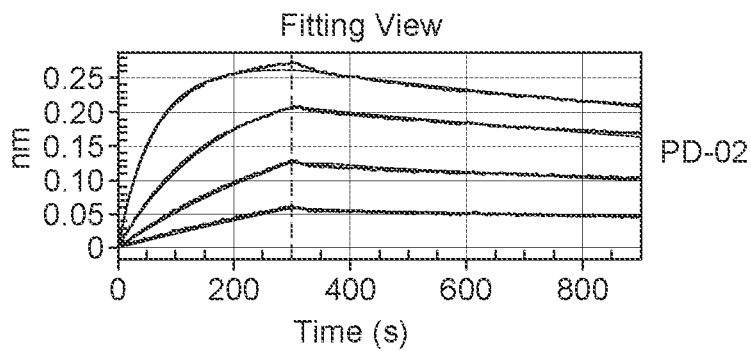
Figure 13C:
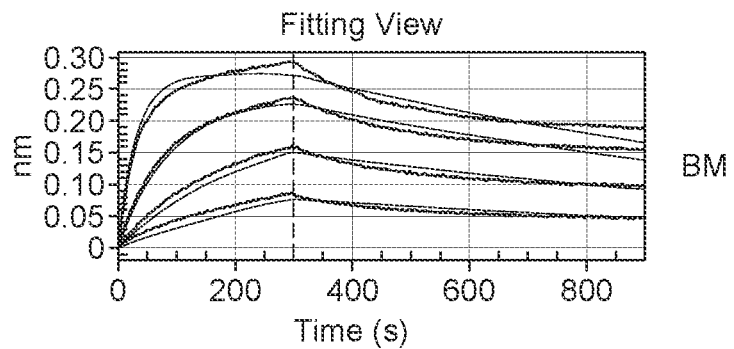

Bio-light interferometry was carried out using the Octet RED96 system (ForteBio Octet RED96 System) to characterize the binding kinetics of antibodies against His tagged human PD-1 protein. 20 nM of antibody was loaded onto the anti-human IgG capture biosensors. Association of analyte (His tagged human PD-1 protein) was observed by placing the biosensors in wells containing 2 or 3 fold serial dilution of analytes (72 nM being the highest concentration) for 5 mins. Dissociation was measured after transfer of the biosensors into kinetic buffer alone and monitoring of the interferometry signal for 10 minutes. The observed on and off rates (Ka and Kd) were fit using a 1:1 binding global fit model comprising at least 5 concentrations tested, and the equilibrium binding constant $K_D$ was then calculated. FIGS. 13A-C shows the binding affinity of PD-01 mab (FIG. 13A), PD-02 mab (FIG. 13B), and benchmark (BM) anti-PD-1 mab (FIG. 13C).

Figure 14:
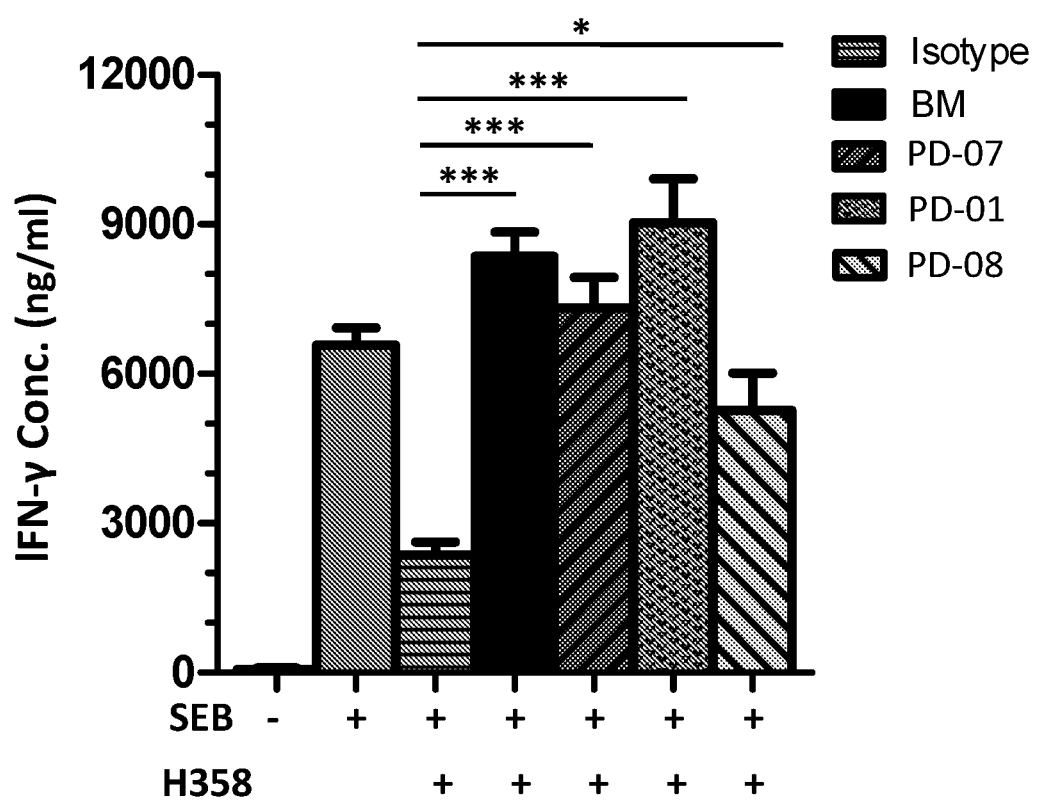
FIG. 14 shows the enhancement of IFN-γ production from human PBMCs by anti-PD-1 mabs.
Figure 15:
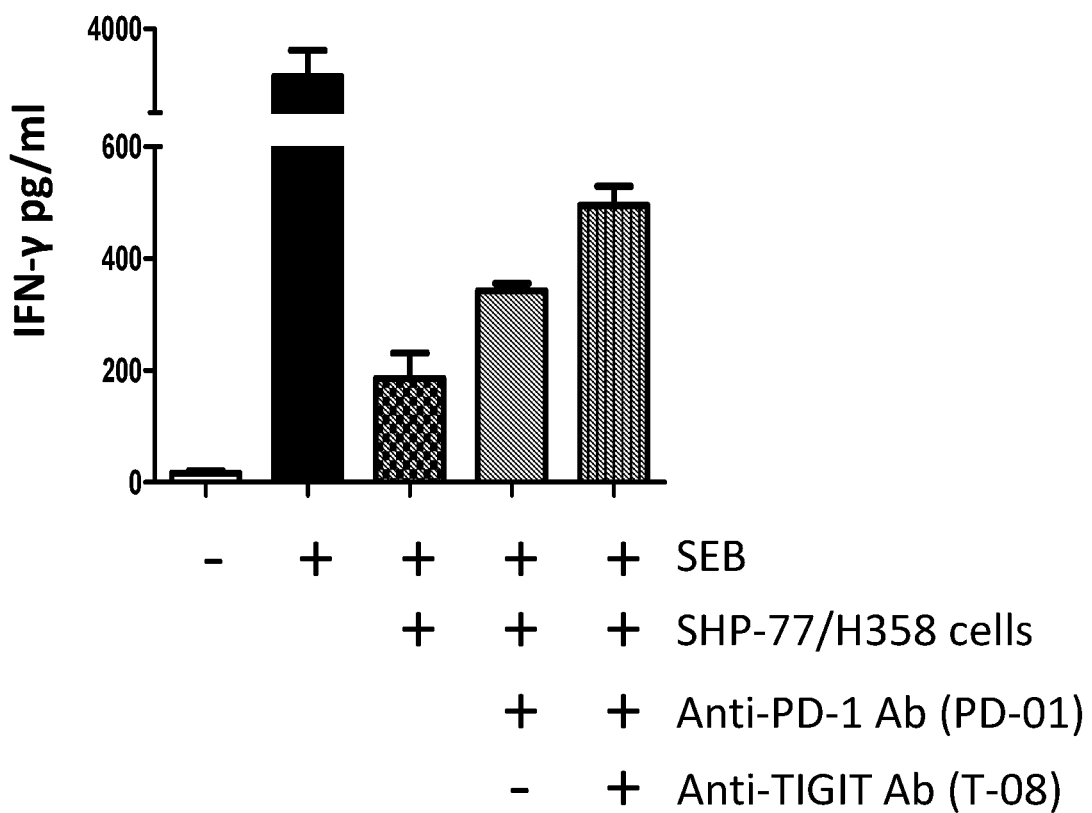
FIG. 15 shows increased IFN-γ production from human PBMCs by a combination of anti-TIGIT- and anti-PD-1 mabs.
Figure 16A:
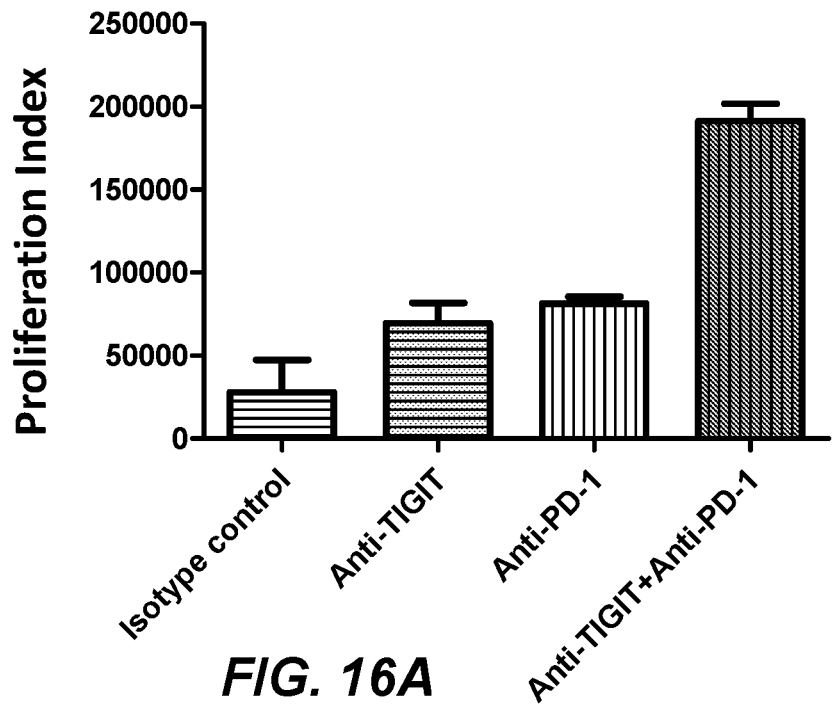
FIGS. 16A and 16B show increased proliferation of human T cell proliferation by a combination of anti-TIGIT- and anti-PD-1 mabs.
Figure 16B:
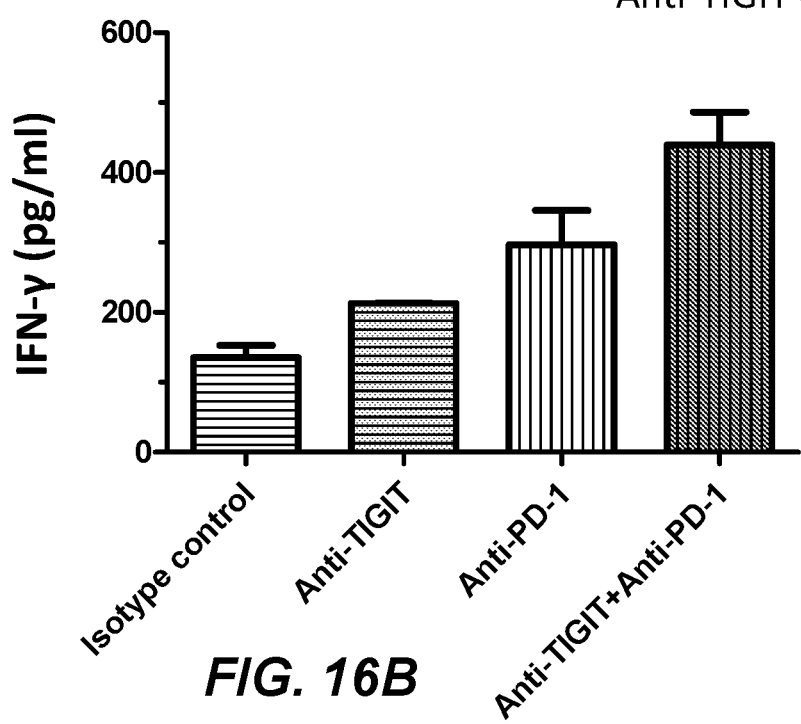
Figure 18A:
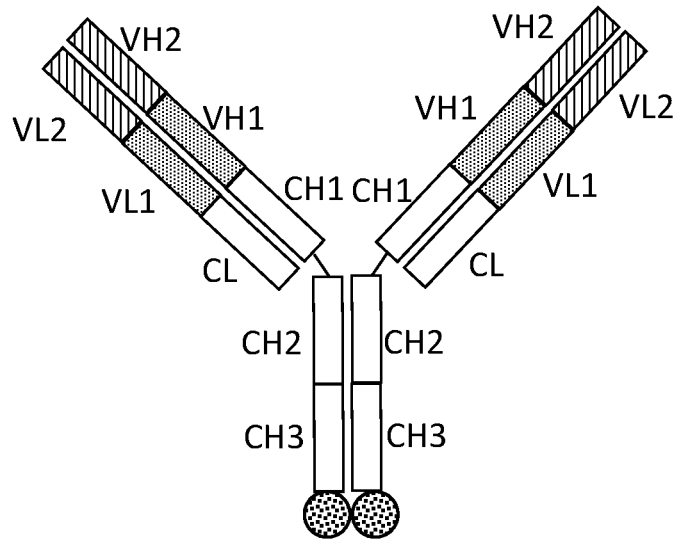
Figure 18B:
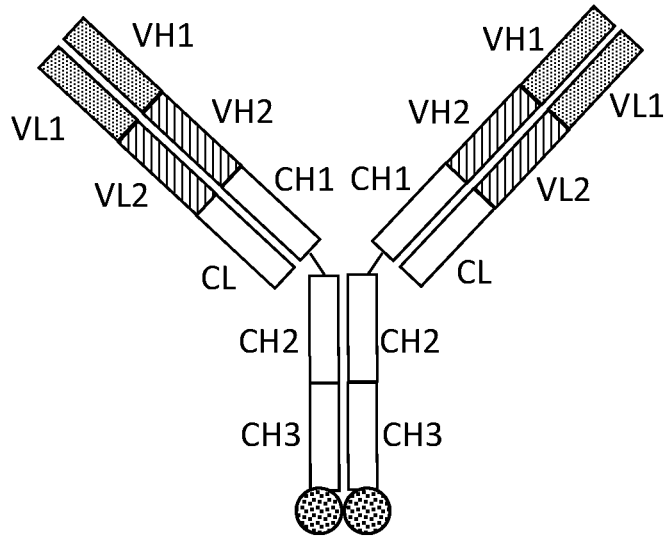
Figure 18E:
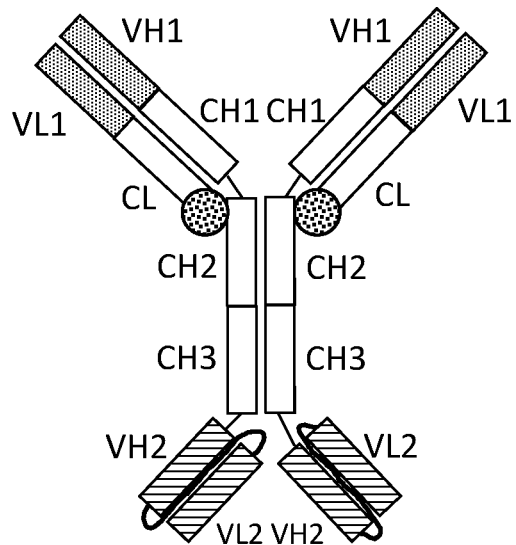
Figure 18F:
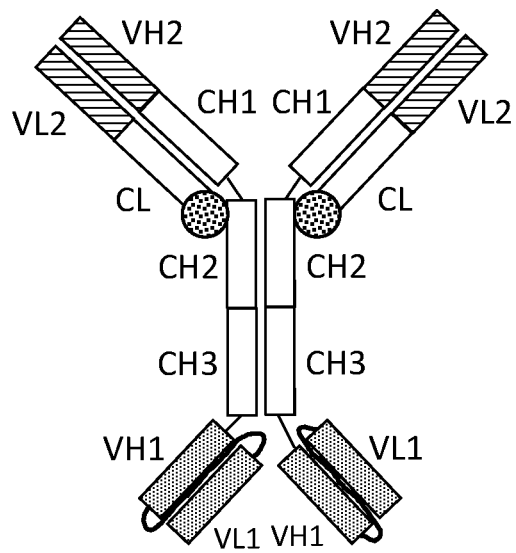

Example 13: Enhanced IFN-γ Production by Anti-PD-1 Mabs Alone or in Combination with Anti-TIGIT Mab To show the ability of the anti-PD-1 antibodies to induce IFN-γ production, 100,000 normal healthy human PBMC were activated with SEB (Toxin Technology). H358 cancer cell lines were added to provide PD-L1 ligand signals. 10 µg/ml of anti-PD-1 mAbs or isotype control Ab were added. 3 days later, supernatant were examined for IFN-γ by ELISA. FIG. 14 shows the enhancement of IFN-γ production from human PBMCs by the anti-PD-1 mabs depicted. FIGS. 15 AND 16B show that a combination of anti-TIGIT (T-08) and anti-PD-1 (PD-01) mabs further increased IFN-γ production from human PBMCs over the level of the anti-PD-1 antibody alone.

Example 14: Enhanced T Cell Proliferation by Anti-PD-1 Mabs Alone or in Combination with Anti-TIGIT Mab To evaluate the ability of the anti-PD-1 antibodies to induce T cell proliferation, an assay was carried out similar to the assay described in Example 7, except that H358 cancer cell lines were added to provide PD-L1 ligand signals. FIGS. 16A and 16B show increased proliferation of human T cell proliferation by a combination of anti-TIGIT- and anti-PD-1 mabs.

Example 15: Screening Assays for Selection of Bispecific Antibodies

Figure 19A:
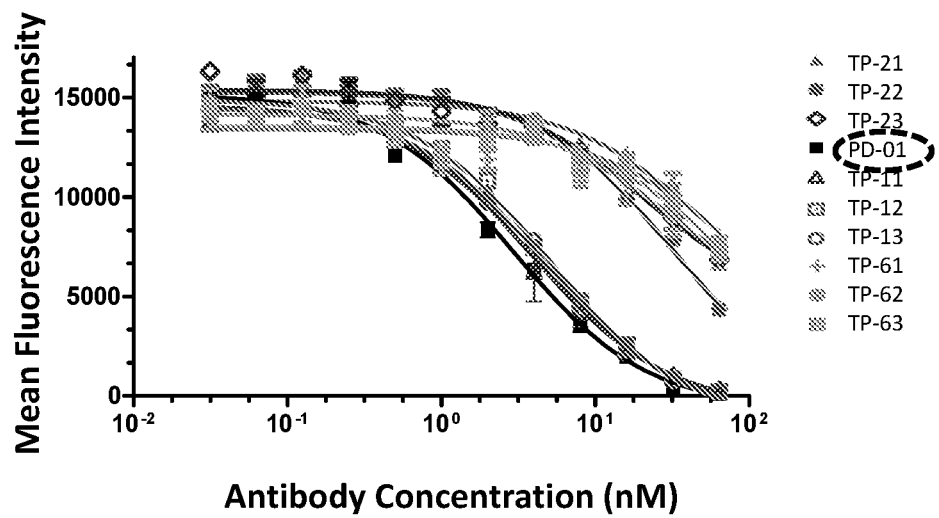
FIGS. 19A-D shows the results of screening assays to identify bispecific antibodies capable of blocking PD-1 binding (FIG. 19A, FIG. 19B) and TIGIT binding (FIG. 19C, FIG. 19D).
Figure 19B:
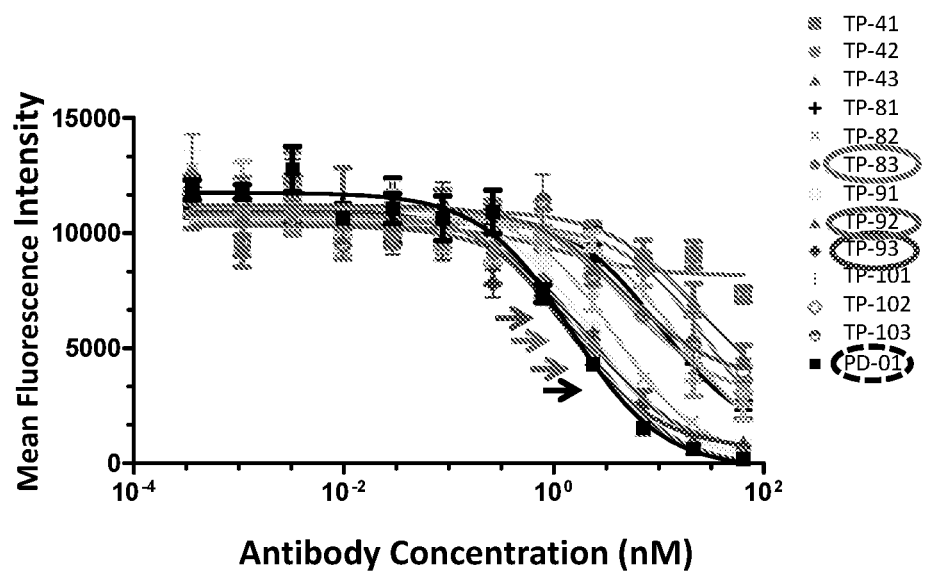
Figure 19C:
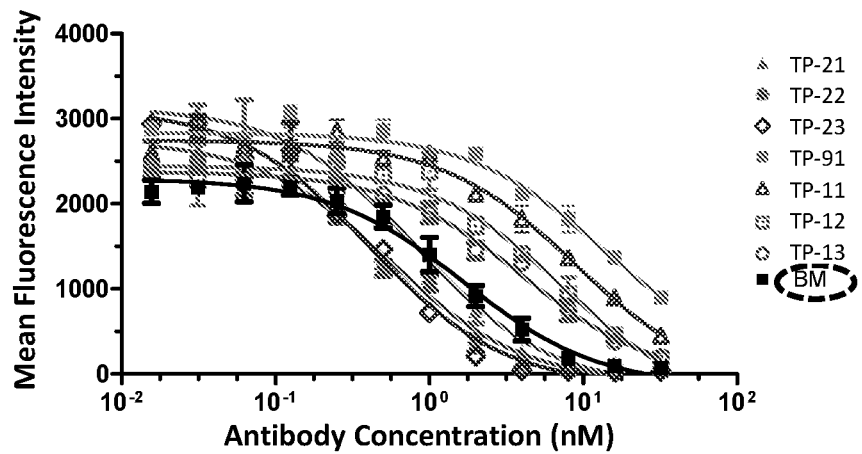
Figure 19D:
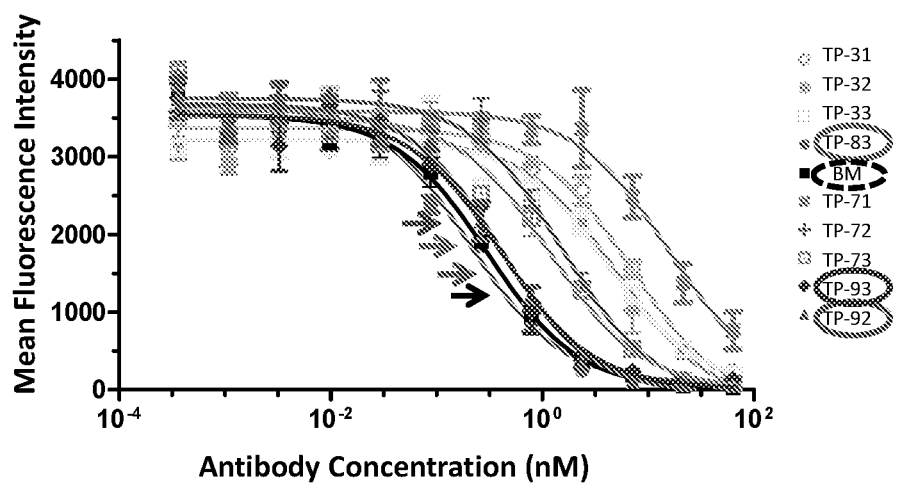

FIGS. 19A-D shows the results of screening assays to identify bispecific antibody configurations capable of blocking both PD-1 binding (FIG. 19A, FIG. 19B) and TIGIT binding (FIG. 19C, FIG. 19D). These screening assays employed the IC50 blocking assays described in Example 6 and 11. Antibody configurations exhibiting effective binding are shown in FIG. 17.

Example 16: Expression and Functional Evaluation of Bispecific Antibodies

Figure 20A:
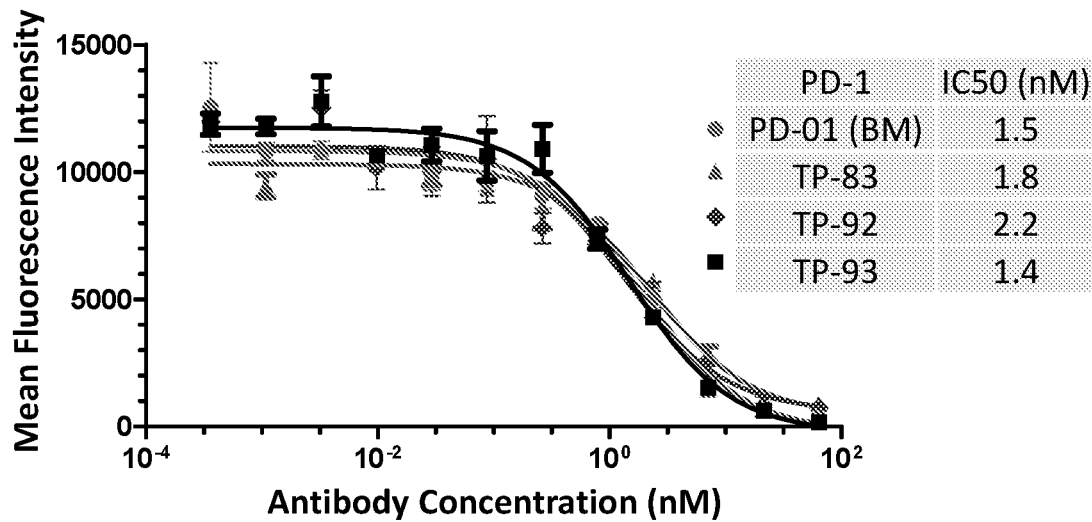
FIGS. 20A and 20B shows the ability of bispecific antibodies (TP-83, TP-92 and TP-93) to block binding of PD-L1 to PD-1 (FIG. 20A) and block binding of PVR to TIGIT (FIG. 20 B).
Figure 20B:
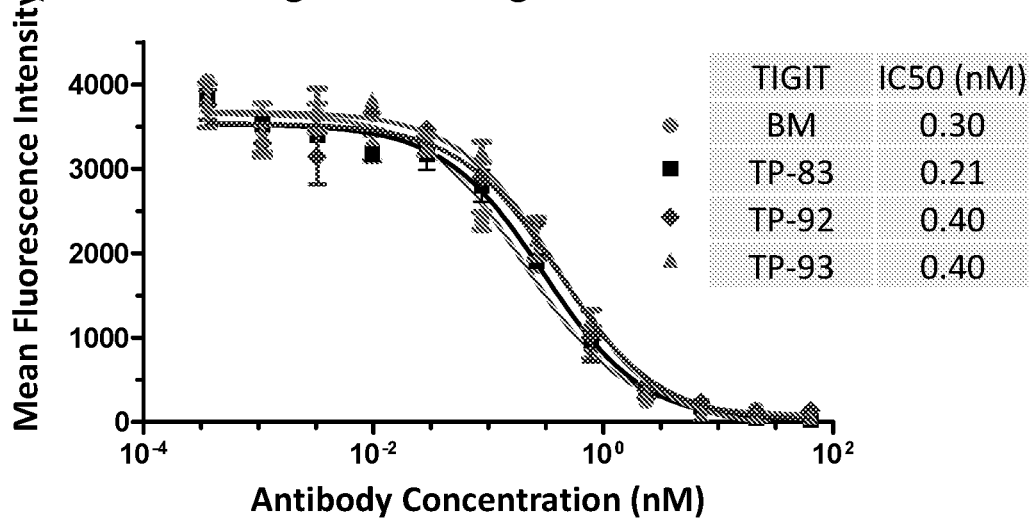
Figure 21A:
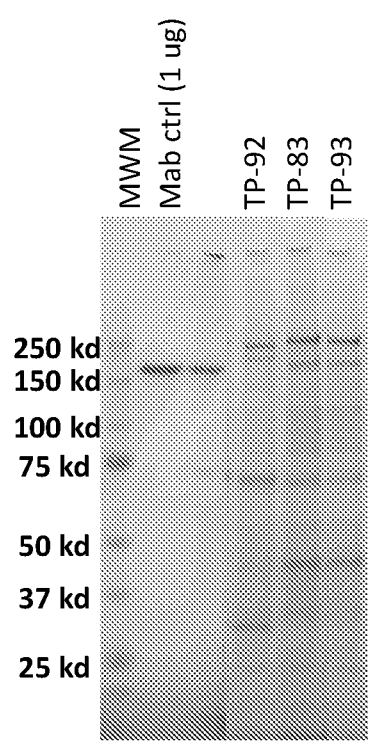
FIGS. 21A and 21B show Coomasie stained gels showing production of bispecific antibodies, TP-83, TP-92 and TP-93.
Figure 21B:
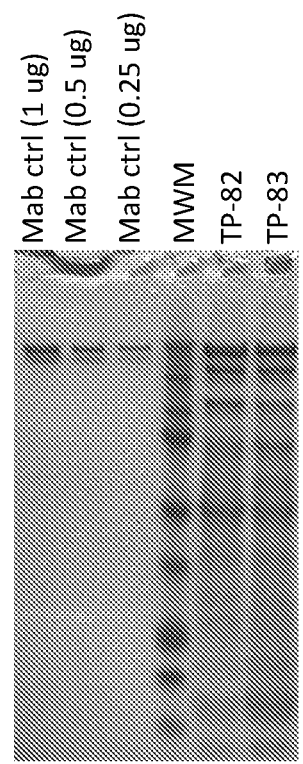

The blocking assay in Example 11 was used to calculate the IC50 for three exemplary bispecific checkpoint regulator antagonists, TP-83, TP-92 and TP-93. FIGS. 20A-B shows the ability of these bispecific checkpoint regulator antagonists to block binding of PD-L1 to PD-1 (FIG. 20A) and block binding of PVR to TIGIT (FIG. 20B). These figures further show the calculated IC50s for blocking the binding of PD-L1 to PD-1 (FIG. 20A) and for blocking the binding of PVR to TIGIT (FIG. 20B). FIG. 21 shows a Coomasie stained gel showing production of bispecific antibodies, TP-83, TP-92 and TP-93.

Figure 22:
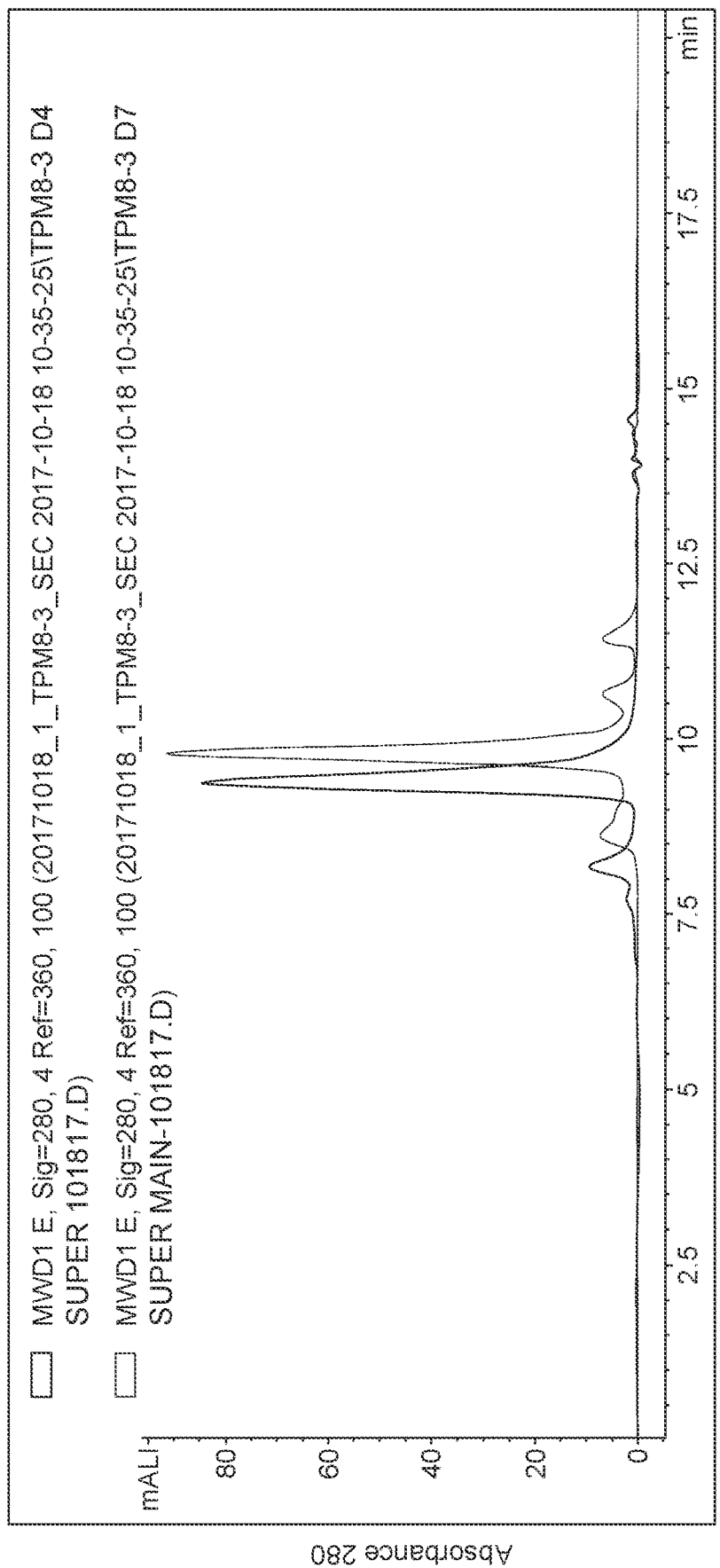
FIG. 22 shows an exemplary size exclusion chromatograph (SEC) profile for bispecific checkpoint antagonists, TP-93 and TP-83, illustrating manufacturability of the molecules after one step purification.

Example 17: Exemplary Size Exclusion Chromatography (SEC) Profile of Bispecific Checkpoint Regulator Antagonists FIG. 22 shows an exemplary SEC profile for exemplary bispecific checkpoint regulator antagonists after one step purification. Briefly, a 20 µg sample (either TP-93 or TP-83) was loaded onto a Zenix SEC-300 column (3 µm, 300 .ANG., 7.8×300 mm). The mobile phase (150 mM sodium phosphate, pH 7.0) was delivered at a flow rate of 0.80 mL/min. UV absorbance was monitored at 280 nm. The main peaks represent the desired products (86% for TP-93 and 74% for TP-83). The minor peaks represent either incorrectly aggregated or assembled products. This analysis underscores the manufacturability of the bispecific checkpoint regulator antagonists according to the present application.

Example 18: Increased Up-Regulation of IFN-γ Production by Bispecific Checkpoint Regulator Antagonists To evaluate the ability of a bispecific checkpoint regulator antagonist (TP-93) to induce T cell proliferation as compared to monospecific anti-TIGIT (T-08) and anti-PD-1 (PD-01) mabs, a CMV antigen specific recall assay was performed. Briefly, PBMCs from individual donors pre-screened for CMV antigen reactivity (Donor 333 and Donor 287) were purchased from Astarte Biologics. Cell lysates from CMV-infected cells (used as CMV antigen) were also purchased from Astarte Biologics. 1) For IFN-g production: 250,000 PBMCs were plated and the antigen-specific stimulation was performed by the addition of 0.1m/ml of CMV Ag, which stimulates the CMV reactive T cells. SHP-77 cells were co-cultured with PBMC to provide an immune function inhibitory environment. IgG4 control, anti-TIGIT Ab, anti-PD-1 Ab, anti-TIGIT Ab plus anti-PD-1 Ab, and bispecific Ab were separately added to each plate. 5 days later, supernatants were examined for IFN-γ production by ELISA. 2) For T-cell proliferation, 250,000 PBMCs were plated and activated with 0.1m/ml of CMV Ag for 2 days and then labeled with CellTrace Far Red. 100,000 labeled PBMC were then re-plated and re-stimulated with 1 μg/ml CMV Ag. 128 nM of IgG4 control, anti-TIGIT Ab, the anti-PD-1 Ab, anti-TIGIT Ab plus anti-PD-1 Ab, or bispecific Ab were separately added to each plate. Total volume per well was 200 μl. The plates were incubated at 37° C. or 5 days post-stimulation and the PBMC cells were stained with PE labeled anti-human CD4 Ab (BioLegend) and analyzed by the iQue intellicyt system. T cell proliferation indices were calculated based on the reduction of mean fluorescence intensity (MFI) of CellTrace Far Red signal on gated CD4+ T cells. 3) T cell surface expression of TIGIT and PD-1 was also examined by FACS at day 5 with APC labeled anti-human CD3, PE labeled anti-TIGIT and FITC labeled anti-PD-1 Abs (data not shown).

Figure 23A:
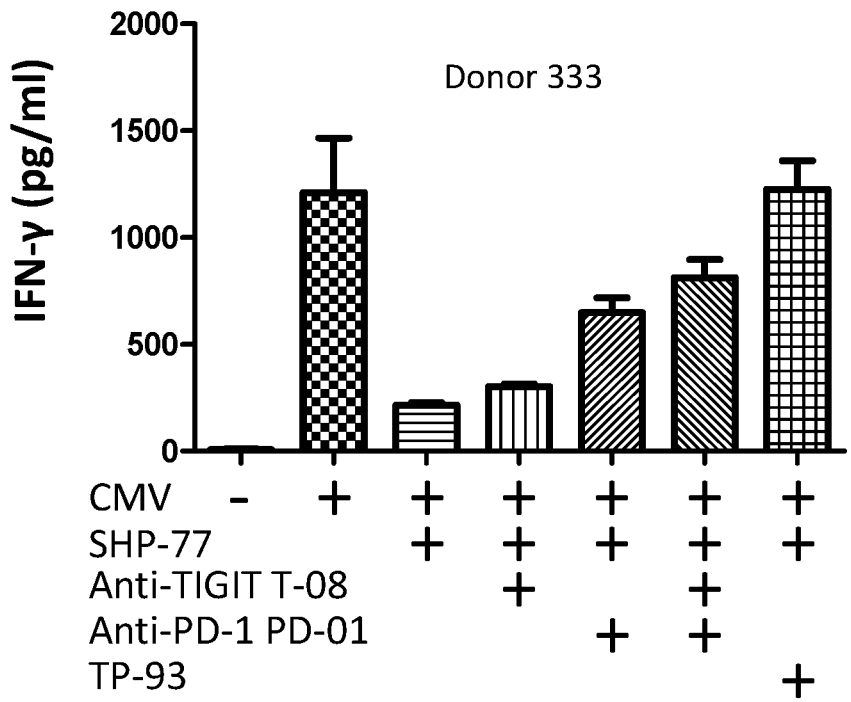
FIGS. 23A-D show increased IFN-γ production from human PBMCs (Donor 333, FIG. 23A, FIG. 23C; Donor 287, FIG. 23B, FIG. 23D) with a bispecific mab (TP-93) relative to individual anti-TIGIT (T-08) and anti-PD-1 (PD-01) mabs.
Figure 23B:
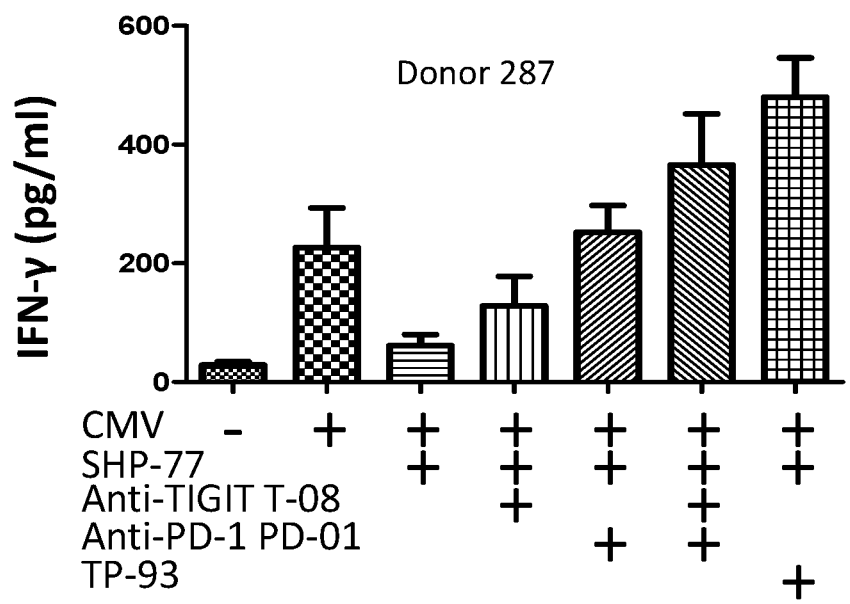
Figure 23C:
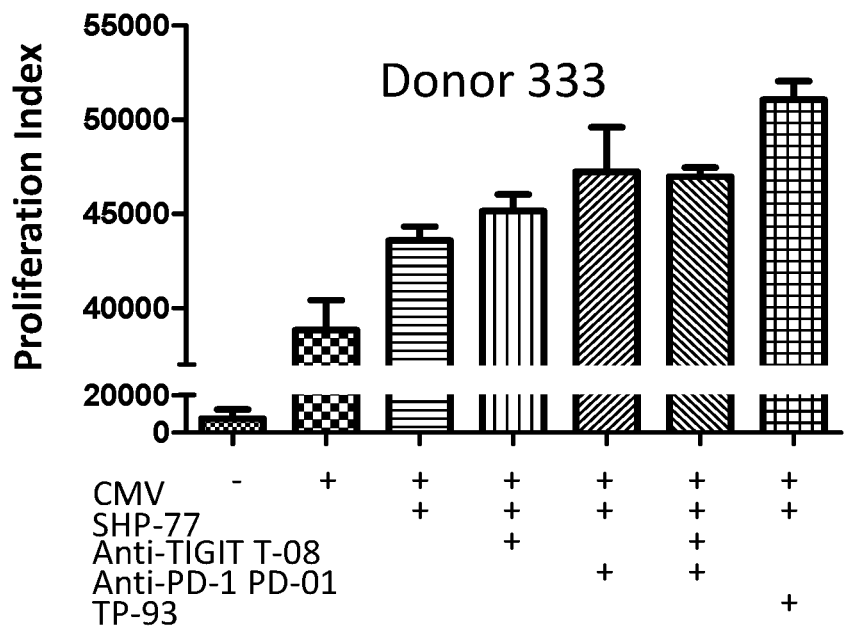
Figure 23D:
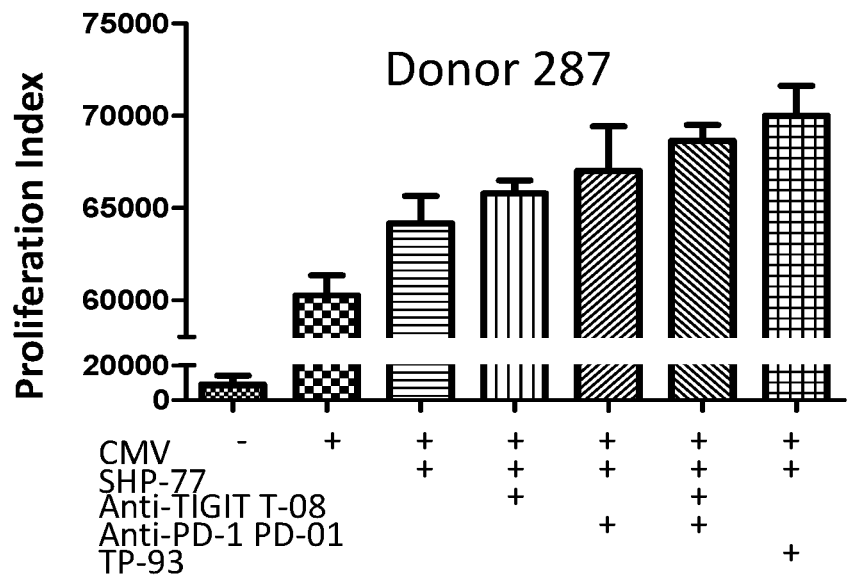

FIGS. 23A and 23B show that the bispecific checkpoint regulator antagonist, TP-93, increased IFN-γ production to a greater extent than the monospecific anti-TIGIT (T-08) and anti-PD-1 (PD-01) mabs alone or a combination of the monospecific anti-TIGIT and anti-PD-1 antibodies using two different human PBMC cell populations (Donor 333, FIG. 23A; Donor 287, FIG. 23B). FIGS. 23C and 23D show that the bispecific checkpoint regulator antagonist, TP-93, exhibited a higher T cell proliferation index than the monospecific anti-TIGIT (T-08) and anti-PD-1 (PD-01) mabs alone or a combination of the monospecific anti-TIGIT and anti-PD-1 antibodies using two different human PBMC cell populations (Donor 333, FIG. 23C; Donor 287, FIG. 23D).

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An antibody, or an antigen-binding portion thereof, comprising:
   (1) a heavy chain variable region, wherein the heavy chain variable region comprises three complementarity determining regions (HCDRs): HCDR1, HCDR2 and HCDR3,
   wherein HCDR1 has an amino acid sequence selected from the group consisting of SEQ ID NOS: 76, 79, 85 and 88,
   wherein HCDR2 has an amino acid sequence selected from the group consisting of SEQ ID NOS: 77, 80, 82, 84, 86 and 89, and
   wherein HCDR3 has an amino acid sequence selected from the group consisting of SEQ ID NOS: 78, 81, 83, 87 and 90; and
   (2) a light chain variable region, wherein the light chain variable region comprises three complementarity determining regions (LCDRs): LCDR1, LCDR2 and LCDR3,
   wherein LCDR1 has an amino acid sequence selected from the group consisting of SEQ ID NOS: 91, 94, 98, 101 and 104,
   wherein LCDR2 has an amino acid sequence selected from the group consisting of SEQ ID NOS: 92, 95, 99, 102 and 105, and
   wherein LCDR3 has an amino acid sequence selected from the group consisting of SEQ ID NOS: 93, 96, 97, 100, 103 and 106, and
   wherein the antibody, or the antigen-binding portion thereof, binds specifically to human PD-L1.

2. A bispecific checkpoint regulator antagonist, comprising an antigen binding domain comprising the antigen-binding portion of the antibody of claim 1.

3. A nucleic acid encoding the bispecific checkpoint regulator antagonist of claim 2.

4. An expression vector comprising the nucleic acid of claim 3.

5. A nucleic acid encoding the antibody, or an antigen-binding portion thereof, of claim 1.

6. An expression vector comprising the nucleic acid of claim 5.

7. The antibody, or an antigen-binding portion thereof, of claim 1, comprising:
   (1) a heavy chain variable region, wherein the heavy chain variable region comprises three complementarity determining regions (HCDRs): HCDR1, HCDR2 and HCDR3,
   wherein HCDR1 has the amino acid sequence of SEQ ID NO:76,
   wherein HCDR2 has the amino acid sequence of SEQ ID NO:77, and
   wherein HCDR3 has the amino acid sequence of SEQ ID NO:78; and
   (2) a light chain variable region, wherein the light chain variable region comprises three complementarity determining regions (LCDRs): LCDR1, LCDR2 and LCDR3,
   wherein LCDR1 has the amino acid sequence of SEQ ID NO:91,
   wherein LCDR2 has the amino acid sequence of SEQ ID NO:92, and
   wherein LCDR3 has the amino acid sequence of SEQ ID NO:93.

8. The antibody, or an antigen-binding portion thereof, of claim 1, comprising:
   (1) a heavy chain variable region, wherein the heavy chain variable region comprises three complementarity determining regions (HCDRs): HCDR1, HCDR2 and HCDR3,
   wherein HCDR1 has the amino acid sequence of SEQ ID NO:79,
   wherein HCDR2 has the amino acid sequence of SEQ ID NO:80, and
   wherein HCDR3 has the amino acid sequence of SEQ ID NO:81; and (2) a light chain variable region, wherein the light chain variable region comprises three complementarity determining regions (LCDRs): LCDR1, LCDR2 and LCDR3,
wherein LCDR1 has the amino acid sequence of SEQ ID NO:94,
wherein LCDR2 has the amino acid sequence of SEQ ID NO:95, and
wherein LCDR3 has the amino acid sequence of SEQ ID NO:96.

9. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:78,
wherein HCDR2 has the amino acid sequence of SEQ ID NO:79, and
wherein HCDR3 has the amino acid sequence of SEQ ID NO:84; and
(2) a light chain variable region, wherein the light chain variable region comprises three complementarity determining regions (LCDRs): LCDR1, LCDR2 and LCDR3,
wherein LCDR1 has the amino acid sequence of SEQ ID NO:92,
wherein LCDR2 has the amino acid sequence of SEQ ID NO:94, and
wherein LCDR3 has the amino acid sequence of SEQ ID NO:96.

10. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:78,
wherein HCDR2 has the amino acid sequence of SEQ ID NO:79, and
wherein HCDR3 has the amino acid sequence of SEQ ID NO:84; and
(2) a light chain variable region, wherein the light chain variable region comprises three complementarity determining regions (LCDRs): LCDR1, LCDR2 and LCDR3,
wherein LCDR1 has the amino acid sequence of SEQ ID NO:92,
wherein LCDR2 has the amino acid sequence of SEQ ID NO:94, and
wherein LCDR3 has the amino acid sequence of SEQ ID NO:97.

11. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:85,
wherein HCDR2 has the amino acid sequence of SEQ ID NO:86, and
wherein HCDR3 has the amino acid sequence of SEQ ID NO:87; and (2) a light chain variable region, wherein the light chain variable region comprises three complementarity determining regions (LCDRs): LCDR1, LCDR2 and LCDR3,
wherein LCDR1 has the amino acid sequence of SEQ ID NO:98,
wherein LCDR2 has the amino acid sequence of SEQ ID NO:99, and
wherein LCDR3 has the amino acid sequence of SEQ ID NO:100.

12. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:88,
wherein HCDR2 has the amino acid sequence of SEQ ID NO:89, and
wherein HCDR3 has the amino acid sequence of SEQ ID NO:90; and
(2) a light chain variable region, wherein the light chain variable region comprises three complementarity determining regions (LCDRs): LCDR1, LCDR2 and LCDR3,
wherein LCDR1 has the amino acid sequence of SEQ ID NO:101,
wherein LCDR2 has the amino acid sequence of SEQ ID NO: 102, and
wherein LCDR3 has the amino acid sequence of SEQ ID NO:103.

13. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:88,
wherein HCDR2 has the amino acid sequence of SEQ ID NO:89, and
wherein HCDR3 has the amino acid sequence of SEQ ID NO:90; and
(2) a light chain variable region, wherein the light chain variable region comprises three complementarity determining regions (LCDRs): LCDR1, LCDR2 and LCDR3,
wherein LCDR1 has the amino acid sequence of SEQ ID NO:104,
wherein LCDR2 has the amino acid sequence of SEQ ID NO: 105, and
wherein LCDR3 has the amino acid sequence of SEQ ID NO:106.

14. The antibody, or an antigen-binding portion thereof, of claim 1, comprising:
(1) a heavy chain variable region, wherein the heavy chain variable region comprises three complementarity determining regions (HCDRs): HCDR1, HCDR2 and HCDR3,
wherein HCDR1 has the amino acid sequence of SEQ ID NO:79,
wherein HCDR2 has the amino acid sequence of SEQ ID NO:82, and
wherein HCDR3 has the amino acid sequence of SEQ ID NO:83; and (2) a light chain variable region, wherein the light chain variable region comprises three complementarity determining regions (LCDRs): LCDR1, LCDR2 and LCDR3, wherein LCDR1 has the amino acid sequence of SEQ ID NO:91, wherein LCDR2 has the amino acid sequence of SEQ ID NO:92, and wherein LCDR3 has the amino acid sequence of SEQ ID NO:93.

15. An antibody, or an antigen-binding portion thereof, comprising:
   (1) a heavy chain variable region having an amino acid sequence selected from the group consisting of SEQ ID NOS: 139, 141, 143, 145, 147, 149, 151 and 153; and
   (2) a light chain variable region having an amino acid sequence sequence selected from the group consisting of SEQ ID NOS: 140, 142, 144, 146, 148, 150, 152 and 154,
   wherein the antibody, or the antigen-binding portion thereof, binds specifically to human PD-L1.

16. A bispecific checkpoint regulator antagonist, comprising an antigen binding domain comprising the antigen-binding portion of the antibody of claim 15.

* * * * *

```
                        SEQUENCE LISTING

Sequence total quantity: 192
SEQ ID NO: 1            moltype = AA  length = 6
FEATURE                 Location/Qualifiers
REGION                  1..6
                        note = Synthetic: HCDR1; TIGIT
source                  1..6
                        mol_type = protein
                        organism = synthetic construct
SEQUENCE: 1
SDYAWN                                                                    6

SEQ ID NO: 2            moltype = AA  length = 16
FEATURE                 Location/Qualifiers
REGION                  1..16
                        note = Synthetic: HCDR2; TIGIT
source                  1..16
                        mol_type = protein
                        organism = synthetic construct
SEQUENCE: 2
YISYSGSTGY NPSLKS                                                        16

SEQ ID NO: 3            moltype = AA  length = 9
FEATURE                 Location/Qualifiers
REGION                  1..9
                        note = Synthetic: HCDR3; TIGIT
source                  1..9
                        mol_type = protein
                        organism = synthetic construct
SEQUENCE: 3
RMIGYAMDY                                                                 9

SEQ ID NO: 4            moltype = AA  length = 17
FEATURE                 Location/Qualifiers
REGION                  1..17
                        note = Synthetic: HCDR2; TIGIT
source                  1..17
                        mol_type = protein
                        organism = synthetic construct
SEQUENCE: 4
YITYSGGSTS YNPSLKS                                                       17

SEQ ID NO: 5            moltype = AA  length = 9
FEATURE                 Location/Qualifiers
REGION                  1..9
                        note = Synthetic: HCDR3; TIGIT
source                  1..9
                        mol_type = protein
                        organism = synthetic construct
SEQUENCE: 5
RQIGLGFTY                                                                 9

SEQ ID NO: 6            moltype = AA  length = 5
```

```
FEATURE                 Location/Qualifiers
REGION                  1..5
                        note = Synthetic: HCDR1; TIGIT
source                  1..5
                        mol_type = protein
                        organism = synthetic construct
SEQUENCE: 6
DHTIH                                                                      5

SEQ ID NO: 7            moltype = AA  length = 17
FEATURE                 Location/Qualifiers
REGION                  1..17
                        note = Synthetic: HCDR2; TIGIT
source                  1..17
                        mol_type = protein
                        organism = synthetic construct
SEQUENCE: 7
YFYPRDGSTK YNEKFKG                                                        17

SEQ ID NO: 8            moltype = AA  length = 8
FEATURE                 Location/Qualifiers
REGION                  1..8
                        note = Synthetic: HCDR3; TIGIT
source                  1..8
                        mol_type = protein
                        organism = synthetic construct
SEQUENCE: 8
GMLRWFAD                                                                   8

SEQ ID NO: 9            moltype = AA  length = 17
FEATURE                 Location/Qualifiers
REGION                  1..17
                        note = Synthetic: HCDR2; TIGIT
source                  1..17
                        mol_type = protein
                        organism = synthetic construct
SEQUENCE: 9
YIYPRDGSSK YNVKFKG                                                        17

SEQ ID NO: 10           moltype = AA  length = 8
FEATURE                 Location/Qualifiers
REGION                  1..8
                        note = Synthetic: HCDR3; TIGIT
source                  1..8
                        mol_type = protein
                        organism = synthetic construct
SEQUENCE: 10
GMLRWFAY                                                                   8

SEQ ID NO: 11           moltype = AA  length = 5
FEATURE                 Location/Qualifiers
REGION                  1..5
                        note = Synthetic: HCDR1; TIGIT
source                  1..5
                        mol_type = protein
                        organism = synthetic construct
SEQUENCE: 11
DQAIH                                                                      5

SEQ ID NO: 12           moltype = AA  length = 17
FEATURE                 Location/Qualifiers
REGION                  1..17
                        note = Synthetic: HCDR2; TIGIT
source                  1..17
                        mol_type = protein
                        organism = synthetic construct
SEQUENCE: 12
YIYPRDGSTK YNETFKG                                                        17

SEQ ID NO: 13           moltype = AA  length = 16
FEATURE                 Location/Qualifiers
REGION                  1..16
                        note = Synthetic: HCDR2; TIGIT
source                  1..16
                        mol_type = protein
                        organism = synthetic construct
SEQUENCE: 13
YITYSGSTSY NPSLKS                                                         16
```

```
SEQ ID NO: 14              moltype = AA   length = 9
FEATURE                    Location/Qualifiers
REGION                     1..9
                           note = Synthetic: HCDR3; TIGIT
source                     1..9
                           mol_type = protein
                           organism = synthetic construct
SEQUENCE: 14
RQVGLGFAY                                                                    9

SEQ ID NO: 15              moltype = AA   length = 6
FEATURE                    Location/Qualifiers
REGION                     1..6
                           note = Synthetic: HCDR1; TIGIT
source                     1..6
                           mol_type = protein
                           organism = synthetic construct
SEQUENCE: 15
SDSAWN                                                                       6

SEQ ID NO: 16              moltype = AA   length = 16
FEATURE                    Location/Qualifiers
REGION                     1..16
                           note = Synthetic: HCDR2; TIGIT
source                     1..16
                           mol_type = protein
                           organism = synthetic construct
SEQUENCE: 16
YITYSGSTNY NPSLRS                                                           16

SEQ ID NO: 17              moltype = AA   length = 5
FEATURE                    Location/Qualifiers
REGION                     1..5
                           note = Synthetic: HCDR1; TIGIT
source                     1..5
                           mol_type = protein
                           organism = synthetic construct
SEQUENCE: 17
NYGMN                                                                        5

SEQ ID NO: 18              moltype = AA   length = 17
FEATURE                    Location/Qualifiers
REGION                     1..17
                           note = Synthetic: HCDR2; TIGIT
source                     1..17
                           mol_type = protein
                           organism = synthetic construct
SEQUENCE: 18
WINTYTGEPT YADDFKG                                                          17

SEQ ID NO: 19              moltype = AA   length = 12
FEATURE                    Location/Qualifiers
REGION                     1..12
                           note = Synthetic: HCDR3; TIGIT
source                     1..12
                           mol_type = protein
                           organism = synthetic construct
SEQUENCE: 19
APPYGYDVRF AY                                                               12

SEQ ID NO: 20              moltype = AA   length = 7
FEATURE                    Location/Qualifiers
REGION                     1..7
                           note = Synthetic: HCDR1; TIGIT
source                     1..7
                           mol_type = protein
                           organism = synthetic construct
SEQUENCE: 20
TFAMGVG                                                                      7

SEQ ID NO: 21              moltype = AA   length = 16
FEATURE                    Location/Qualifiers
REGION                     1..16
                           note = Synthetic: HCDR2; TIGIT
source                     1..16
                           mol_type = protein
                           organism = synthetic construct
SEQUENCE: 21
HIWWDDDKYY NPALKS                                                           16
```

```
SEQ ID NO: 22              moltype = AA   length = 11
FEATURE                    Location/Qualifiers
REGION                     1..11
                           note = Synthetic: HCDR3; TIGIT
source                     1..11
                           mol_type = protein
                           organism = synthetic construct
SEQUENCE: 22
MDYSYFAWFA Y                                                                    11

SEQ ID NO: 23              moltype = AA   length = 5
FEATURE                    Location/Qualifiers
REGION                     1..5
                           note = Synthetic: HCDR1; TIGIT
source                     1..5
                           mol_type = protein
                           organism = synthetic construct
SEQUENCE: 23
SYYMH                                                                            5

SEQ ID NO: 24              moltype = AA   length = 16
FEATURE                    Location/Qualifiers
REGION                     1..16
                           note = Synthetic: HCDR2; TIGIT
source                     1..16
                           mol_type = protein
                           organism = synthetic construct
SEQUENCE: 24
INPSGGRTSY AQMFQG                                                               16

SEQ ID NO: 25              moltype = AA   length = 13
FEATURE                    Location/Qualifiers
REGION                     1..13
                           note = Synthetic: HCDR3; TIGIT
source                     1..13
                           mol_type = protein
                           organism = synthetic construct
SEQUENCE: 25
DREEQWPVGG FDY                                                                  13

SEQ ID NO: 26              moltype = AA   length = 11
FEATURE                    Location/Qualifiers
REGION                     1..11
                           note = Synthetic: LCDR1; TIGIT
source                     1..11
                           mol_type = protein
                           organism = synthetic construct
SEQUENCE: 26
KASQDVSTVV A                                                                    11

SEQ ID NO: 27              moltype = AA   length = 7
FEATURE                    Location/Qualifiers
REGION                     1..7
                           note = Synthetic: LCDR2; TIGIT
source                     1..7
                           mol_type = protein
                           organism = synthetic construct
SEQUENCE: 27
SASYRYT                                                                          7

SEQ ID NO: 28              moltype = AA   length = 9
FEATURE                    Location/Qualifiers
REGION                     1..9
                           note = Synthetic: LCDR3; TIGIT
source                     1..9
                           mol_type = protein
                           organism = synthetic construct
SEQUENCE: 28
QQHYSTPWT                                                                        9

SEQ ID NO: 29              moltype = AA   length = 11
FEATURE                    Location/Qualifiers
REGION                     1..11
                           note = Synthetic: LCDR1; TIGIT
source                     1..11
                           mol_type = protein
                           organism = synthetic construct
SEQUENCE: 29
```

```
KASQDLSTAV A                                                                    11

SEQ ID NO: 30          moltype = AA   length = 7
FEATURE                Location/Qualifiers
REGION                 1..7
                       note = Synthetic: LCDR2; TIGIT
source                 1..7
                       mol_type = protein
                       organism = synthetic construct
SEQUENCE: 30
SSSYRYT                                                                         7

SEQ ID NO: 31          moltype = AA   length = 11
FEATURE                Location/Qualifiers
REGION                 1..11
                       note = Synthetic: LCDR1; TIGIT
source                 1..11
                       mol_type = protein
                       organism = synthetic construct
SEQUENCE: 31
KASQDVSTTV A                                                                    11

SEQ ID NO: 32          moltype = AA   length = 9
FEATURE                Location/Qualifiers
REGION                 1..9
                       note = Synthetic: LCDR3; TIGIT
source                 1..9
                       mol_type = protein
                       organism = synthetic construct
SEQUENCE: 32
QQHYSTPLT                                                                       9

SEQ ID NO: 33          moltype = AA   length = 11
FEATURE                Location/Qualifiers
REGION                 1..11
                       note = Synthetic: LCDR1; TIGIT
source                 1..11
                       mol_type = protein
                       organism = synthetic construct
SEQUENCE: 33
KASQDVFTAV A                                                                    11

SEQ ID NO: 34          moltype = AA   length = 9
FEATURE                Location/Qualifiers
REGION                 1..9
                       note = Synthetic: LCDR3; TIGIT
source                 1..9
                       mol_type = protein
                       organism = synthetic construct
SEQUENCE: 34
QQHYSIPLT                                                                       9

SEQ ID NO: 35          moltype = AA   length = 11
FEATURE                Location/Qualifiers
REGION                 1..11
                       note = Synthetic: LCDR1; TIGIT
source                 1..11
                       mol_type = protein
                       organism = synthetic construct
SEQUENCE: 35
KASQDVSTAV A                                                                    11

SEQ ID NO: 36          moltype = AA   length = 7
FEATURE                Location/Qualifiers
REGION                 1..7
                       note = Synthetic: LCDR2; TIGIT
source                 1..7
                       mol_type = protein
                       organism = synthetic construct
SEQUENCE: 36
SASYHYT                                                                         7

SEQ ID NO: 37          moltype = AA   length = 7
FEATURE                Location/Qualifiers
REGION                 1..7
                       note = Synthetic: LCDR2; TIGIT
source                 1..7
                       mol_type = protein
                       organism = synthetic construct
```

```
SEQUENCE: 37
SASYRFT                                                                            7

SEQ ID NO: 38         moltype = AA   length = 9
FEATURE               Location/Qualifiers
REGION                1..9
                      note = Synthetic: LCDR3; TIGIT
source                1..9
                      mol_type = protein
                      organism = synthetic construct
SEQUENCE: 38
QHHYSTPWT                                                                          9

SEQ ID NO: 39         moltype = AA   length = 16
FEATURE               Location/Qualifiers
REGION                1..16
                      note = Synthetic: LCDR1; TIGIT
source                1..16
                      mol_type = protein
                      organism = synthetic construct
SEQUENCE: 39
RSSQSIVHSN GNTYLE                                                                 16

SEQ ID NO: 40         moltype = AA   length = 7
FEATURE               Location/Qualifiers
REGION                1..7
                      note = Synthetic: LCDR2; TIGIT
source                1..7
                      mol_type = protein
                      organism = synthetic construct
SEQUENCE: 40
KVSDRFS                                                                            7

SEQ ID NO: 41         moltype = AA   length = 9
FEATURE               Location/Qualifiers
REGION                1..9
                      note = Synthetic: LCDR3; TIGIT
source                1..9
                      mol_type = protein
                      organism = synthetic construct
SEQUENCE: 41
FQGSHVPWT                                                                          9

SEQ ID NO: 42         moltype = AA   length = 14
FEATURE               Location/Qualifiers
REGION                1..14
                      note = Synthetic: LCDR1; TIGIT
source                1..14
                      mol_type = protein
                      organism = synthetic construct
SEQUENCE: 42
RSSTGAVTTS NYAN                                                                   14

SEQ ID NO: 43         moltype = AA   length = 7
FEATURE               Location/Qualifiers
REGION                1..7
                      note = Synthetic: LCDR2; TIGIT
source                1..7
                      mol_type = protein
                      organism = synthetic construct
SEQUENCE: 43
GTNNRAP                                                                            7

SEQ ID NO: 44         moltype = AA   length = 9
FEATURE               Location/Qualifiers
REGION                1..9
                      note = Synthetic: LCDR3; TIGIT
source                1..9
                      mol_type = protein
                      organism = synthetic construct
SEQUENCE: 44
ALWYSNHWV                                                                          9

SEQ ID NO: 45         moltype = AA   length = 11
FEATURE               Location/Qualifiers
REGION                1..11
                      note = Synthetic: LCDR1; TIGIT
source                1..11
                      mol_type = protein
```

```
                                    -continued

SEQUENCE: 45
RASQSIRRYL N                                                              11

SEQ ID NO: 46            moltype = AA   length = 7
FEATURE                  Location/Qualifiers
REGION                   1..7
                         note = Synthetic: LCDR2; TIGIT
source                   1..7
                         mol_type = protein
                         organism = synthetic construct
SEQUENCE: 46
SASNLQS                                                                    7

SEQ ID NO: 47            moltype = AA   length = 9
FEATURE                  Location/Qualifiers
REGION                   1..9
                         note = Synthetic: LCDR3; TIGIT
source                   1..9
                         mol_type = protein
                         organism = synthetic construct
SEQUENCE: 47
QQSYIIPPT                                                                  9

SEQ ID NO: 48            moltype = AA   length = 5
FEATURE                  Location/Qualifiers
REGION                   1..5
                         note = Synthetic: HCDR1; PD-1
source                   1..5
                         mol_type = protein
                         organism = synthetic construct
SEQUENCE: 48
NFLMS                                                                      5

SEQ ID NO: 49            moltype = AA   length = 17
FEATURE                  Location/Qualifiers
REGION                   1..17
                         note = Synthetic: HCDR2; PD-1
source                   1..17
                         mol_type = protein
                         organism = synthetic construct
SEQUENCE: 49
TISGGGRDTY YVDSVKG                                                        17

SEQ ID NO: 50            moltype = AA   length = 8
FEATURE                  Location/Qualifiers
REGION                   1..8
                         note = Synthetic: HCDR3; PD-1
source                   1..8
                         mol_type = protein
                         organism = synthetic construct
SEQUENCE: 50
RTTYSMDY                                                                   8

SEQ ID NO: 51            moltype = AA   length = 5
FEATURE                  Location/Qualifiers
REGION                   1..5
                         note = Synthetic: HCDR1; PD-1
source                   1..5
                         mol_type = protein
                         organism = synthetic construct
SEQUENCE: 51
NSYLY                                                                      5

SEQ ID NO: 52            moltype = AA   length = 17
FEATURE                  Location/Qualifiers
REGION                   1..17
                         note = Synthetic: HCDR2; PD-1
source                   1..17
                         mol_type = protein
                         organism = synthetic construct
SEQUENCE: 52
GINPSNGGTN FNEKFKT                                                        17

SEQ ID NO: 53            moltype = AA   length = 11
FEATURE                  Location/Qualifiers
REGION                   1..11
                         note = Synthetic: HCDR3; PD-1
source                   1..11
```

```
SEQUENCE: 53
RDYNYDGGFD S                                                              11

SEQ ID NO: 54          moltype = AA   length = 5
FEATURE                Location/Qualifiers
REGION                 1..5
                       note = Synthetic: HCDR1; PD-1
source                 1..5
                       mol_type = protein
                       organism = synthetic construct
SEQUENCE: 54
NSYIY                                                                      5

SEQ ID NO: 55          moltype = AA   length = 12
FEATURE                Location/Qualifiers
REGION                 1..12
                       note = Synthetic: HCDR3; PD-1
source                 1..12
                       mol_type = protein
                       organism = synthetic construct
SEQUENCE: 55
RRDYRYDGGF DS                                                             12

SEQ ID NO: 56          moltype = AA   length = 5
FEATURE                Location/Qualifiers
REGION                 1..5
                       note = Synthetic: HCDR1; PD-1
source                 1..5
                       mol_type = protein
                       organism = synthetic construct
SEQUENCE: 56
TYYIY                                                                      5

SEQ ID NO: 57          moltype = AA   length = 17
FEATURE                Location/Qualifiers
REGION                 1..17
                       note = Synthetic: HCDR2; PD-1
source                 1..17
                       mol_type = protein
                       organism = synthetic construct
SEQUENCE: 57
GINPGNGGTN FNEKFKI                                                        17

SEQ ID NO: 58          moltype = AA   length = 11
FEATURE                Location/Qualifiers
REGION                 1..11
                       note = Synthetic: HCDR3; PD-1
source                 1..11
                       mol_type = protein
                       organism = synthetic construct
SEQUENCE: 58
RYHGYDGGLD Y                                                              11

SEQ ID NO: 59          moltype = AA   length = 5
FEATURE                Location/Qualifiers
REGION                 1..5
                       note = Synthetic: HCDR1; PD-1
source                 1..5
                       mol_type = protein
                       organism = synthetic construct
SEQUENCE: 59
SYYIH                                                                      5

SEQ ID NO: 60          moltype = AA   length = 17
FEATURE                Location/Qualifiers
REGION                 1..17
                       note = Synthetic: HCDR2; PD-1
source                 1..17
                       mol_type = protein
                       organism = synthetic construct
SEQUENCE: 60
WIFPGSGNSK YNENFKG                                                        17

SEQ ID NO: 61          moltype = AA   length = 13
FEATURE                Location/Qualifiers
REGION                 1..13
                       note = Synthetic: HCDR3; PD-1
```

```
source                  1..13
                        mol_type = protein
                        organism = synthetic construct
SEQUENCE: 61
SDYGSSPYYY FDY                                                       13

SEQ ID NO: 62           moltype = AA  length = 11
FEATURE                 Location/Qualifiers
REGION                  1..11
                        note = Synthetic: LCDR1; PD-1
source                  1..11
                        mol_type = protein
                        organism = synthetic construct
SEQUENCE: 62
LASQTIGTWL A                                                         11

SEQ ID NO: 63           moltype = AA  length = 7
FEATURE                 Location/Qualifiers
REGION                  1..7
                        note = Synthetic: LCDR2; PD-1
source                  1..7
                        mol_type = protein
                        organism = synthetic construct
SEQUENCE: 63
AATSLAD                                                               7

SEQ ID NO: 64           moltype = AA  length = 9
FEATURE                 Location/Qualifiers
REGION                  1..9
                        note = Synthetic: LCDR3; PD-1
source                  1..9
                        mol_type = protein
                        organism = synthetic construct
SEQUENCE: 64
QQFYSIPWT                                                             9

SEQ ID NO: 65           moltype = AA  length = 12
FEATURE                 Location/Qualifiers
REGION                  1..12
                        note = Synthetic: LCDR1; PD-1
source                  1..12
                        mol_type = protein
                        organism = synthetic construct
SEQUENCE: 65
RASSTLYSNY LH                                                        12

SEQ ID NO: 66           moltype = AA  length = 7
FEATURE                 Location/Qualifiers
REGION                  1..7
                        note = Synthetic: LCDR2; PD-1
source                  1..7
                        mol_type = protein
                        organism = synthetic construct
SEQUENCE: 66
RASFLAS                                                               7

SEQ ID NO: 67           moltype = AA  length = 9
FEATURE                 Location/Qualifiers
REGION                  1..9
                        note = Synthetic: LCDR3; PD-1
source                  1..9
                        mol_type = protein
                        organism = synthetic construct
SEQUENCE: 67
QQGSSIPLT                                                             9

SEQ ID NO: 68           moltype = AA  length = 12
FEATURE                 Location/Qualifiers
REGION                  1..12
                        note = Synthetic: LCDR1; PD-1
source                  1..12
                        mol_type = protein
                        organism = synthetic construct
SEQUENCE: 68
SASSSLYSSY LH                                                        12

SEQ ID NO: 69           moltype = AA  length = 12
FEATURE                 Location/Qualifiers
REGION                  1..12
```

```
                        note = Synthetic: LCDR1; PD-1
source                  1..12
                        mol_type = protein
                        organism = synthetic construct
SEQUENCE: 69
RASSSLYSNY LH                                                             12

SEQ ID NO: 70           moltype = AA  length = 15
FEATURE                 Location/Qualifiers
REGION                  1..15
                        note = Synthetic: LCDR1; PD-1
source                  1..15
                        mol_type = protein
                        organism = synthetic construct
SEQUENCE: 70
RASKSVSTSG FSYIH                                                          15

SEQ ID NO: 71           moltype = AA  length = 7
FEATURE                 Location/Qualifiers
REGION                  1..7
                        note = Synthetic: LCDR2; PD-1
source                  1..7
                        mol_type = protein
                        organism = synthetic construct
SEQUENCE: 71
LASNLES                                                                    7

SEQ ID NO: 72           moltype = AA  length = 9
FEATURE                 Location/Qualifiers
REGION                  1..9
                        note = Synthetic: LCDR3; PD-1
source                  1..9
                        mol_type = protein
                        organism = synthetic construct
SEQUENCE: 72
QHTWELPNT                                                                  9

SEQ ID NO: 73           moltype = AA  length = 11
FEATURE                 Location/Qualifiers
REGION                  1..11
                        note = Synthetic: LCDR1; PD-1
source                  1..11
                        mol_type = protein
                        organism = synthetic construct
SEQUENCE: 73
KASQNVGTNV A                                                              11

SEQ ID NO: 74           moltype = AA  length = 7
FEATURE                 Location/Qualifiers
REGION                  1..7
                        note = Synthetic: LCDR2; PD-1
source                  1..7
                        mol_type = protein
                        organism = synthetic construct
SEQUENCE: 74
SASYRYS                                                                    7

SEQ ID NO: 75           moltype = AA  length = 9
FEATURE                 Location/Qualifiers
REGION                  1..9
                        note = Synthetic: LCDR3; PD-1
source                  1..9
                        mol_type = protein
                        organism = synthetic construct
SEQUENCE: 75
QQYYSYPYT                                                                  9

SEQ ID NO: 76           moltype = AA  length = 5
FEATURE                 Location/Qualifiers
REGION                  1..5
                        note = Synthetic: HCDR1; PD-L1
source                  1..5
                        mol_type = protein
                        organism = synthetic construct
SEQUENCE: 76
NYWMH                                                                      5

SEQ ID NO: 77           moltype = AA  length = 17
FEATURE                 Location/Qualifiers
```

```
REGION                  1..17
                        note = Synthetic: HCDR2; PD-L1
source                  1..17
                        mol_type = protein
                        organism = synthetic construct
SEQUENCE: 77
MIHPNTNNYN YNEKFKS                                                      17

SEQ ID NO: 78           moltype = AA  length = 12
FEATURE                 Location/Qualifiers
REGION                  1..12
                        note = Synthetic: HCDR3; PD-L1
source                  1..12
                        mol_type = protein
                        organism = synthetic construct
SEQUENCE: 78
SDYGSSPYYF DY                                                           12

SEQ ID NO: 79           moltype = AA  length = 5
FEATURE                 Location/Qualifiers
REGION                  1..5
                        note = Synthetic: HCDR1; PD-L1
source                  1..5
                        mol_type = protein
                        organism = synthetic construct
SEQUENCE: 79
SYWMH                                                                    5

SEQ ID NO: 80           moltype = AA  length = 17
FEATURE                 Location/Qualifiers
REGION                  1..17
                        note = Synthetic: HCDR2; PD-L1
source                  1..17
                        mol_type = protein
                        organism = synthetic construct
SEQUENCE: 80
MIHPNVGSTN YNEKFKS                                                      17

SEQ ID NO: 81           moltype = AA  length = 12
FEATURE                 Location/Qualifiers
REGION                  1..12
                        note = Synthetic: HCDR3; PD-L1
source                  1..12
                        mol_type = protein
                        organism = synthetic construct
SEQUENCE: 81
SRYGSSPYYF DY                                                           12

SEQ ID NO: 82           moltype = AA  length = 17
FEATURE                 Location/Qualifiers
REGION                  1..17
                        note = Synthetic: HCDR2; PD-L1
source                  1..17
                        mol_type = protein
                        organism = synthetic construct
SEQUENCE: 82
MIHPNSGGNN YNEKFKS                                                      17

SEQ ID NO: 83           moltype = AA  length = 12
FEATURE                 Location/Qualifiers
REGION                  1..12
                        note = Synthetic: HCDR3; PD-L1
source                  1..12
                        mol_type = protein
                        organism = synthetic construct
SEQUENCE: 83
SWYGSSPYYF DY                                                           12

SEQ ID NO: 84           moltype = AA  length = 17
FEATURE                 Location/Qualifiers
REGION                  1..17
                        note = Synthetic: HCDR2; PD-L1
source                  1..17
                        mol_type = protein
                        organism = synthetic construct
SEQUENCE: 84
MIHPTGVSTD YNEKFKS                                                      17

SEQ ID NO: 85           moltype = AA  length = 6
```

```
FEATURE                 Location/Qualifiers
REGION                  1..6
                        note = Synthetic: HCDR1; PD-L1
source                  1..6
                        mol_type = protein
                        organism = synthetic construct
SEQUENCE: 85
SDYAWN                                                                  6

SEQ ID NO: 86           moltype = AA  length = 16
FEATURE                 Location/Qualifiers
REGION                  1..16
                        note = Synthetic: HCDR2; PD-L1
source                  1..16
                        mol_type = protein
                        organism = synthetic construct
SEQUENCE: 86
YISDSGSTSY NPSLKS                                                      16

SEQ ID NO: 87           moltype = AA  length = 11
FEATURE                 Location/Qualifiers
REGION                  1..11
                        note = Synthetic: HCDR3; PD-L1
source                  1..11
                        mol_type = protein
                        organism = synthetic construct
SEQUENCE: 87
SFLRLRSYFD H                                                           11

SEQ ID NO: 88           moltype = AA  length = 5
FEATURE                 Location/Qualifiers
REGION                  1..5
                        note = Synthetic: HCDR1; PD-L1
source                  1..5
                        mol_type = protein
                        organism = synthetic construct
SEQUENCE: 88
SYGIN                                                                   5

SEQ ID NO: 89           moltype = AA  length = 17
FEATURE                 Location/Qualifiers
REGION                  1..17
                        note = Synthetic: LCDR1; PD-L1
source                  1..17
                        mol_type = protein
                        organism = synthetic construct
SEQUENCE: 89
CIYIGNDYTN YNEKFKG                                                     17

SEQ ID NO: 90           moltype = AA  length = 9
FEATURE                 Location/Qualifiers
REGION                  1..9
                        note = Synthetic: LCDR2; PD-L1
source                  1..9
                        mol_type = protein
                        organism = synthetic construct
SEQUENCE: 90
AYYGSRVDY                                                               9

SEQ ID NO: 91           moltype = AA  length = 11
FEATURE                 Location/Qualifiers
REGION                  1..11
                        note = Synthetic: LCDR1; PD-L1
source                  1..11
                        mol_type = protein
                        organism = synthetic construct
SEQUENCE: 91
RASQDIDNYL N                                                           11

SEQ ID NO: 92           moltype = AA  length = 7
FEATURE                 Location/Qualifiers
REGION                  1..7
                        note = Synthetic: LCDR2; PD-L1
source                  1..7
                        mol_type = protein
                        organism = synthetic construct
SEQUENCE: 92
YTSRLHS                                                                 7
```

```
SEQ ID NO: 93           moltype = AA  length = 9
FEATURE                 Location/Qualifiers
REGION                  1..9
                        note = Synthetic: LCDR3; PD-L1
source                  1..9
                        mol_type = protein
                        organism = synthetic construct
SEQUENCE: 93
QQGYTLPWT                                                                      9

SEQ ID NO: 94           moltype = AA  length = 11
FEATURE                 Location/Qualifiers
REGION                  1..11
                        note = Synthetic: LCDR1; PD-L1
source                  1..11
                        mol_type = protein
                        organism = synthetic construct
SEQUENCE: 94
RASQDISNYL N                                                                  11

SEQ ID NO: 95           moltype = AA  length = 7
FEATURE                 Location/Qualifiers
REGION                  1..7
                        note = Synthetic: LCDR2; PD-L1
source                  1..7
                        mol_type = protein
                        organism = synthetic construct
SEQUENCE: 95
YTSRLQS                                                                        7

SEQ ID NO: 96           moltype = AA  length = 9
FEATURE                 Location/Qualifiers
REGION                  1..9
                        note = Synthetic: LCDR3; PD-L1
source                  1..9
                        mol_type = protein
                        organism = synthetic construct
SEQUENCE: 96
QQGNTLPWT                                                                      9

SEQ ID NO: 97           moltype = AA  length = 9
FEATURE                 Location/Qualifiers
REGION                  1..9
                        note = Synthetic: LCDR3; PD-L1
source                  1..9
                        mol_type = protein
                        organism = synthetic construct
SEQUENCE: 97
QQGDTLPWT                                                                      9

SEQ ID NO: 98           moltype = AA  length = 11
FEATURE                 Location/Qualifiers
REGION                  1..11
                        note = Synthetic: LCDR1; PD-L1
source                  1..11
                        mol_type = protein
                        organism = synthetic construct
SEQUENCE: 98
KASQDVNVAV A                                                                  11

SEQ ID NO: 99           moltype = AA  length = 7
FEATURE                 Location/Qualifiers
REGION                  1..7
                        note = Synthetic: LCDR2; PD-L1
source                  1..7
                        mol_type = protein
                        organism = synthetic construct
SEQUENCE: 99
WASTRHI                                                                        7

SEQ ID NO: 100          moltype = AA  length = 9
FEATURE                 Location/Qualifiers
REGION                  1..9
                        note = Synthetic: LCDR3; PD-L1
source                  1..9
                        mol_type = protein
                        organism = synthetic construct
SEQUENCE: 100
QQHYSTPYT                                                                      9
```

```
SEQ ID NO: 101           moltype = AA   length = 11
FEATURE                  Location/Qualifiers
REGION                   1..11
                         note = Synthetic: LCDR1; PD-L1
source                   1..11
                         mol_type = protein
                         organism = synthetic construct
SEQUENCE: 101
KASQDINKYI A                                                             11

SEQ ID NO: 102           moltype = AA   length = 7
FEATURE                  Location/Qualifiers
REGION                   1..7
                         note = Synthetic: LCDR2; PD-L1
source                   1..7
                         mol_type = protein
                         organism = synthetic construct
SEQUENCE: 102
YTSTLQP                                                                   7

SEQ ID NO: 103           moltype = AA   length = 8
FEATURE                  Location/Qualifiers
REGION                   1..8
                         note = Synthetic: LCDR3; PD-L1
source                   1..8
                         mol_type = protein
                         organism = synthetic construct
SEQUENCE: 103
LQYDNLYT                                                                  8

SEQ ID NO: 104           moltype = AA   length = 8
FEATURE                  Location/Qualifiers
REGION                   1..8
                         note = Synthetic: LCDR1; PD-L1
source                   1..8
                         mol_type = protein
                         organism = synthetic construct
SEQUENCE: 104
QSISDYLH                                                                  8

SEQ ID NO: 105           moltype = AA   length = 8
FEATURE                  Location/Qualifiers
REGION                   1..8
                         note = Synthetic: LCDR2; PD-L1
source                   1..8
                         mol_type = protein
                         organism = synthetic construct
SEQUENCE: 105
CASQSISG                                                                  8

SEQ ID NO: 106           moltype = AA   length = 9
FEATURE                  Location/Qualifiers
REGION                   1..9
                         note = Synthetic: LCDR3; PD-L1
source                   1..9
                         mol_type = protein
                         organism = synthetic construct
SEQUENCE: 106
QNGHSFPYT                                                                 9

SEQ ID NO: 107           moltype = AA   length = 118
FEATURE                  Location/Qualifiers
REGION                   1..118
                         note = Synthetic: HCVR; TIGIT
source                   1..118
                         mol_type = protein
                         organism = synthetic construct
SEQUENCE: 107
QVQLQESGPG LVKPSQTLSL TCTVSGYSIT SDYAWNWIRQ PPGKGLEWIG YISYSGSTGY          60
NPSLKSRVTI SVDTSKNQFS LKLSSVTAAD TAVYYCARRM IGYAMDYWGQ GTSVTVSS          118

SEQ ID NO: 108           moltype = AA   length = 115
FEATURE                  Location/Qualifiers
REGION                   1..115
                         note = Synthetic: LCVR; TIGIT
source                   1..115
                         mol_type = protein
                         organism = synthetic construct
```

```
SEQUENCE: 108
DIQMTQSPSS LSASVGDRVT ITCKASQDVS TVVAWHQQKP GKAPKLLIYS ASYRYTGVPS    60
RFSGSGSGTD FTLTISSLQP EDFATYYCQQ SYSTPQQHYS TPWTFGGGTK LEIKR        115

SEQ ID NO: 109             moltype = AA   length = 118
FEATURE                    Location/Qualifiers
REGION                     1..118
                           note = Synthetic: HCVR; TIGIT
source                     1..118
                           mol_type = protein
                           organism = synthetic construct
SEQUENCE: 109
QVKLQESGPG LVKPSQTLSL TCTVTGYSIT SDYAWNWIRQ PPGKGLEWIG YITYSGGTSY    60
NPSLKSRVTI SVDTSKNQFS LKLSSVTAAD TAVYSCARRQ IGLGFTYWGQ GTLVTVSA    118

SEQ ID NO: 110             moltype = AA   length = 114
FEATURE                    Location/Qualifiers
REGION                     1..114
                           note = Synthetic: LCVR; TIGIT
source                     1..114
                           mol_type = protein
                           organism = synthetic construct
SEQUENCE: 110
DIQMTQSPSS LSASVGDRVT IPCKASQDLS TAVAWYQQKP GKAPKLLIYS SSYRYTGVPS    60
RFSGSGSGTD FTLTISSLQP EDFATYYCQQ SYSTPQQHYS TPWTFGEGTK LEIK         114

SEQ ID NO: 111             moltype = AA   length = 118
FEATURE                    Location/Qualifiers
REGION                     1..118
                           note = Synthetic: HCVR; TIGIT
source                     1..118
                           mol_type = protein
                           organism = synthetic construct
SEQUENCE: 111
EVQLVQSGAE VKKPGATVKI SCKVSGYTFT DHTIHWVQQA PGKGLEWMGY FYPRDGSTKY    60
NEKFKGRVTI TADTSTDTAY MELSSLRSED TAVYYCATGM LRWFADWGQG TLITVSVA    118

SEQ ID NO: 112             moltype = AA   length = 107
FEATURE                    Location/Qualifiers
REGION                     1..107
                           note = Synthetic: LCVR; TIGIT
source                     1..107
                           mol_type = protein
                           organism = synthetic construct
SEQUENCE: 112
DIQMTQSPSS LSASVGDRVT ITCKASQDVS TTVAWYQQKP GKAPKLLIYS ASYRYTGVPS    60
RFSGSGSGTD FTLTISSLQP EDFATYYCQQ HYSTPLTFGA GTKLELK                 107

SEQ ID NO: 113             moltype = AA   length = 117
FEATURE                    Location/Qualifiers
REGION                     1..117
                           note = Synthetic: HCVR; TIGIT
source                     1..117
                           mol_type = protein
                           organism = synthetic construct
SEQUENCE: 113
EVQLVQSGAE VKKPGATVKI SCKVSGYTFT DHTIHWVQQA PGKGLEWMGY IYPRDGSSKY    60
NVKFKGRVTI TADTSTDTAY MELSSLRSED TAVYYCATGM LRWFAYWGQG TLVTVSS     117

SEQ ID NO: 114             moltype = AA   length = 107
FEATURE                    Location/Qualifiers
REGION                     1..107
                           note = Synthetic: LCVR; TIGIT
source                     1..107
                           mol_type = protein
                           organism = synthetic construct
SEQUENCE: 114
DIQMTQSPSS LSASVGDRVT ITCKASQDVF TAVAWYQQKP GKAPKLLIYS ASYRYTGVPS    60
RFSGSGSGTD FTFTISSLQP EDIATYYCQQ HYSIPLTFGA GTKLEIK                 107

SEQ ID NO: 115             moltype = AA   length = 117
FEATURE                    Location/Qualifiers
REGION                     1..117
                           note = Synthetic: HCVR; TIGIT
source                     1..117
                           mol_type = protein
                           organism = synthetic construct
SEQUENCE: 115
EVQLKQSGAE VKKPGATVKI SCKVSGYTFT DQAIHWVQQA PGKGLEWMGY IYPRDGSTKY    60
```

```
NETFKGRVTI TADTSTDTAY MELSSLRSED TAVYFCARGM LRWFAYWGQG TLVTVSS         117

SEQ ID NO: 116          moltype = AA  length = 107
FEATURE                 Location/Qualifiers
REGION                  1..107
                        note = Synthetic: LCVR; TIGIT
source                  1..107
                        mol_type = protein
                        organism = synthetic construct
SEQUENCE: 116
DIQMTQSPSS LSASVGDRVT ITCKASQDVS TAVAWYQQKP GKAPKLLIYS ASYRYTGVPS      60
RFSGSGSGTD FTLTISSLQP EDFATYYCQQ HYSTPLTFGA GTKLELK                   107

SEQ ID NO: 117          moltype = AA  length = 118
FEATURE                 Location/Qualifiers
REGION                  1..118
                        note = Synthetic: HCVR; TIGIT
source                  1..118
                        mol_type = protein
                        organism = synthetic construct
SEQUENCE: 117
QVQLQESGPG LVKPSQTLSL TCTVSGGSVS SDYAWNWIRQ PPGKGLEWIG YITYSGSTSY      60
NPSLKSRVTI SVDTSKNQFS LKLSSVTAAD TAVYYCARRQ VGLGFAYWGQ GTLVTVSA       118

SEQ ID NO: 118          moltype = AA  length = 107
FEATURE                 Location/Qualifiers
REGION                  1..107
                        note = Synthetic: LCVR; TIGIT
source                  1..107
                        mol_type = protein
                        organism = synthetic construct
SEQUENCE: 118
DIQMTQSPSS LSASVGDRVT ITCKASQDVS TAVAWYQQKP GKAPKLLIYS ASYHYTGVPS      60
RFSGSGSGTD FTLTISSLQP EDFATYYCQQ HYSTPWTFGG GTKLEIK                   107

SEQ ID NO: 119          moltype = AA  length = 118
FEATURE                 Location/Qualifiers
REGION                  1..118
                        note = Synthetic: HCVR; TIGIT
source                  1..118
                        mol_type = protein
                        organism = synthetic construct
SEQUENCE: 119
EVQLQESGPG LVKPSDTLSL TCAVSGYSIT SDSAWNWIRQ PPGKGLEWIG YITYSGSTNY      60
NPSLRSRVTM SVDTSKNQFS LKLSSVTAVD TAVYYCTRRQ VGLGFAYWGQ GTLVTVSA       118

SEQ ID NO: 120          moltype = AA  length = 107
FEATURE                 Location/Qualifiers
REGION                  1..107
                        note = Synthetic: LCVR; TIGIT
source                  1..107
                        mol_type = protein
                        organism = synthetic construct
SEQUENCE: 120
DIQMTQSPSS LSASVGDRVT ITCKASQDVS TAVAWYQQKP GKAPKLLIYS ASYRFTGAPS      60
RFSGSGSGTD FTLTISSLQP EDFGIYYCQH HYSTPWTFGG GTKLEFK                   107

SEQ ID NO: 121          moltype = AA  length = 121
FEATURE                 Location/Qualifiers
REGION                  1..121
                        note = Synthetic: HCVR; TIGIT
source                  1..121
                        mol_type = protein
                        organism = synthetic construct
SEQUENCE: 121
QVQLVQSGSE LKKPGASVKV SCKASGYTFT NYGMNWVRQA PGQGLEWMGW INTYTGEPTY      60
ADDFKGRFVF SLDTSVSTAY LQISSLKAED TAVYYCARAP PYGYDVRFAY WGQGTLVTVS     120
S                                                                    121

SEQ ID NO: 122          moltype = AA  length = 112
FEATURE                 Location/Qualifiers
REGION                  1..112
                        note = Synthetic: LCVR; TIGIT
source                  1..112
                        mol_type = protein
                        organism = synthetic construct
SEQUENCE: 122
DVVMTQSPLS LPVTLGQPAS ISCRSSQSIV HSNGNTYLEW FQQRPGQSPR VLIYKVSDRF      60
SGVPDRFSGS GSGTDFTLKI SRVEAEDVGV YYCFQGSHVP WTFGRGTKLE IK             112
```

```
SEQ ID NO: 123          moltype = AA   length = 121
FEATURE                 Location/Qualifiers
REGION                  1..121
                        note = Synthetic: HCVR; TIGIT
source                  1..121
                        mol_type = protein
                        organism = synthetic construct
SEQUENCE: 123
QVTLKESGPT LVKPTQTLTL TCTFSGFSLS TFAMGVGWIR QPPGKALEWL AHIWWDDDKY    60
YNPALKSRLT ITKDTSKNQV VLTMTNMDPV DTATYYCARM DYSYFAWFAY WGQGTLVTVS   120
S                                                                   121

SEQ ID NO: 124          moltype = AA   length = 109
FEATURE                 Location/Qualifiers
REGION                  1..109
                        note = Synthetic: LCVR; TIGIT
source                  1..109
                        mol_type = protein
                        organism = synthetic construct
SEQUENCE: 124
QAVVTQEPSL TVSPGGTVTL TCRSSTGAVT TSNYANWVQQ KPGQLFRGLI GGTNNRAPWV    60
PARFSGSLIG DKAALTLSGV QPEDEAEYFC ALWYSNHWVF GGGTKLTVL               109

SEQ ID NO: 125          moltype = AA   length = 122
FEATURE                 Location/Qualifiers
REGION                  1..122
                        note = Synthetic: HCVR; TIGIT
source                  1..122
                        mol_type = protein
                        organism = synthetic construct
SEQUENCE: 125
QVQLVQSGAE VKKPGASVKV SCKASGYTFT SYYMHWVRQA PGQGLEWMGI INPSGGRTSY    60
AQMFQGRVTM TRDTSTSTVY MELSSLRSED TAVYYCARDR EEQWPVGGFD YWGQGTLVTV   120
SS                                                                  122

SEQ ID NO: 126          moltype = AA   length = 108
FEATURE                 Location/Qualifiers
REGION                  1..108
                        note = Synthetic: LCVR; TIGIT
source                  1..108
                        mol_type = protein
                        organism = synthetic construct
SEQUENCE: 126
DIQMTQSPSS LSASVGDRVT ITCRASQSIR RYLNWYQQKP GKAPKLLIYS ASNLQSGVPS    60
RFSGSGSGTD FTLTISSLQP EDFATYYCQQ SYIIPPTFGQ GTKVEIRR                108

SEQ ID NO: 127          moltype = AA   length = 117
FEATURE                 Location/Qualifiers
REGION                  1..117
                        note = Synthetic: HCVR; PD-1
source                  1..117
                        mol_type = protein
                        organism = synthetic construct
SEQUENCE: 127
EVQLVESGGG LVQPGGSLRL SCAASGFTFS NFLMSWVRQA PGKGLEWVST ISGGGRDTYY    60
VDSVKGRFTI SRDNSKNTLY LQMNSLRAED TAVYYCAKRT TYSMDYWGQG TSVTVSS      117

SEQ ID NO: 128          moltype = AA   length = 107
FEATURE                 Location/Qualifiers
REGION                  1..107
                        note = Synthetic: LCVR; PD-1
source                  1..107
                        mol_type = protein
                        organism = synthetic construct
SEQUENCE: 128
DIQMTQSPSS VSASVGDRVT ITCLASQTIG TWLAWYQQKP GKAPKLLIYA ATSLADGVPS    60
RFSGSGSGTD FTLTISSLQP EDFATYYCQQ FYSIPWTFGG GTKLEIK                 107

SEQ ID NO: 129          moltype = AA   length = 120
FEATURE                 Location/Qualifiers
REGION                  1..120
                        note = Synthetic: HCVR; PD-1
source                  1..120
                        mol_type = protein
                        organism = synthetic construct
SEQUENCE: 129
QVQLVQSGAE VKKPGASVKV SCKASDYTFT NSYLYWLRQA PGQGLEWMGG INPSNGGTNF    60
NEKFKTRTTS TRDTSISTAY MELSRLRSDD TVVYYCTRRD YNYDGGFDSW GQGTLVTVSS   120
```

```
SEQ ID NO: 130          moltype = AA  length = 108
FEATURE                 Location/Qualifiers
REGION                  1..108
                        note = Synthetic: LCVR; PD-1
source                  1..108
                        mol_type = protein
                        organism = synthetic construct
SEQUENCE: 130
DIQMTQSPSS LSASVGDRVT FTCRASSTLY SNYLHWYQQK PGKAPKLLIY RASFLASGVP    60
SRFSGSGSGT DFTLTISSLQ PEDFATYYCQ QGSSIPLTFG GGTKVEIK                108

SEQ ID NO: 131          moltype = AA  length = 120
FEATURE                 Location/Qualifiers
REGION                  1..120
                        note = Synthetic: HCVR; PD-1
source                  1..120
                        mol_type = protein
                        organism = synthetic construct
SEQUENCE: 131
QVQLVQSGAE VKKPGASVKV SCKASDYTFT NSYIYWVRQA PGQGLEWMGG INPSNGGTNF    60
NEKFKTRVTS TRDTSISTAY MELSRLRSDD TVVYYCARRD YRYDGGFDSW GQGTTLTVSS   120

SEQ ID NO: 132          moltype = AA  length = 108
FEATURE                 Location/Qualifiers
REGION                  1..108
                        note = Synthetic: LCVR; PD-1
source                  1..108
                        mol_type = protein
                        organism = synthetic construct
SEQUENCE: 132
DIQMTQSPSS LSASVGDRVT ITCSASSSLY SSYLHWYQQK PGKAPKLLIY RASFLASGVP    60
SRFSGSGSGT DFTLTISSLQ PEDFATYYCQ QGSSIPLTFG AGTKLDLK                108

SEQ ID NO: 133          moltype = AA  length = 120
FEATURE                 Location/Qualifiers
REGION                  1..120
                        note = Synthetic: HCVR; PD-1
source                  1..120
                        mol_type = protein
                        organism = synthetic construct
SEQUENCE: 133
QVQLVQSGAE VKKPGASVKV SCKASDYTFT NSYIYWVRQA PGQGLEWMGG INPSNGGTNF    60
NEKFKTRVTS TRDTSISTAY MELSRLRSDD TVVYYCARRD YNYDGGFDSW GQGTLVTVSS   120

SEQ ID NO: 134          moltype = AA  length = 108
FEATURE                 Location/Qualifiers
REGION                  1..108
                        note = Synthetic: LCVR; PD-1
source                  1..108
                        mol_type = protein
                        organism = synthetic construct
SEQUENCE: 134
DIQMTQSPSS LSASVGDRVT FTCRASSSLY SNYLHWYQQK PGKAPKLLIY RASFLASGVP    60
SRFSGSGSGT DFTLTISSLQ PEDFATYYCQ QGSSIPLTFG GGTKVEIK                108

SEQ ID NO: 135          moltype = AA  length = 120
FEATURE                 Location/Qualifiers
REGION                  1..120
                        note = Synthetic: HCVR; PD-1
source                  1..120
                        mol_type = protein
                        organism = synthetic construct
SEQUENCE: 135
QVQLVQSGAE VKKPGASVKV SCKASGYTFT TYYIYWVRQA PGQGLEWMGG INPGNGGTNF    60
NEKFKIRVTM TRDTSISTAY MELSSLRSED TAVYYCARRY HGYDGGLDYW GQGTLVTVSS   120

SEQ ID NO: 136          moltype = AA  length = 111
FEATURE                 Location/Qualifiers
REGION                  1..111
                        note = Synthetic: LCVR; PD-1
source                  1..111
                        mol_type = protein
                        organism = synthetic construct
SEQUENCE: 136
DIVLTQSPAS LAVSPGQRAT ITCRASKSVS TSGFSYIHWY QQKPGQPPKL IYLASNLES    60
GVPARFSGSG SGTDFTLTIN PVEANDTANY YCQHTWELPN TFGGGTKVEI K            111

SEQ ID NO: 137          moltype = AA  length = 117
```

```
FEATURE                 Location/Qualifiers
REGION                  1..117
                        note = Synthetic: HCVR; PD-1
source                  1..117
                        mol_type = protein
                        organism = synthetic construct
SEQUENCE: 137
QVQLVQSGAE VKKPGASVKV SCKASGYTFT SYYIHWVRQA PGQRLEWMGW IFPGSGNSKY    60
NENFKGRVTI TRDTSASTAY MELSSLRSED TAVYFCASET YDYGDYWGQG TLVTVSS      117

SEQ ID NO: 138          moltype = AA  length = 107
FEATURE                 Location/Qualifiers
REGION                  1..107
                        note = Synthetic: LCVR; PD-1
source                  1..107
                        mol_type = protein
                        organism = synthetic construct
SEQUENCE: 138
DIQMTQSPSS LSASVGDRVT ITCKASQNVG TNVAWYQQKP GKAPKSLIYS ASYRYSGVPS    60
RFSGSGSGTD FTLTISSLQP EDFATYFCQQ YYSYPYTFGQ GTKLEIK                 107

SEQ ID NO: 139          moltype = AA  length = 121
FEATURE                 Location/Qualifiers
REGION                  1..121
                        note = Synthetic: HCVR; PD-L1
source                  1..121
                        mol_type = protein
                        organism = synthetic construct
SEQUENCE: 139
QVQLVQSGAE VKKPGASVKV SCKASGYTFT NYWMHWMKQA PGQGLEWMGM IHPNTNNYNY    60
NEKFKSRVTS TRDTSISTAY MELSRLRSDD TVVYYCARSD YGSSPYYFDY WGQGTLVTVS   120
S                                                                  121

SEQ ID NO: 140          moltype = AA  length = 107
FEATURE                 Location/Qualifiers
REGION                  1..107
                        note = Synthetic: LCVR; PD-L1
source                  1..107
                        mol_type = protein
                        organism = synthetic construct
SEQUENCE: 140
DIQMTQSPSS LSASVGDRVT ISCRASQDID NYLNWYQQKP GKAPKLLIKY TSRLHSGVPS    60
RFSGSGSGTD FTLTISSLQP EDFATYFCQQ GYTLPWTFGG GTKVEIK                 107

SEQ ID NO: 141          moltype = AA  length = 121
FEATURE                 Location/Qualifiers
REGION                  1..121
                        note = Synthetic: HCVR; PD-L1
source                  1..121
                        mol_type = protein
                        organism = synthetic construct
SEQUENCE: 141
QVQLVQSGAE VKKPGASVKV SCKASGYTFT SYWMHWVRQA PGQGLEWMGM IHPNVGSTNY    60
NEKFKSKATM TRDKSSSTVY MELSSLRSED TAVYYCARSR YGSSPYYFDY WGQGTLVTVS   120
S                                                                  121

SEQ ID NO: 142          moltype = AA  length = 107
FEATURE                 Location/Qualifiers
REGION                  1..107
                        note = Synthetic: LCVR; PD-L1
source                  1..107
                        mol_type = protein
                        organism = synthetic construct
SEQUENCE: 142
DIQMTQSPSS LSASVGDRVT ISCRASQDIS NYLNWYQQKP GKAPKLLIYY TSRLQSGVPS    60
RFSGSGSGTD FTFTISSLQP EDIATYFCQQ GNTLPWTFGQ GTKVEIK                 107

SEQ ID NO: 143          moltype = AA  length = 121
FEATURE                 Location/Qualifiers
REGION                  1..121
                        note = Synthetic: HCVR; PD-L1
source                  1..121
                        mol_type = protein
                        organism = synthetic construct
SEQUENCE: 143
QVQLVQSGAE VKKPGASVKV SCKASGYTFT SYWMHWVRQA PGQGLEWMGM IHPNSGGNNY    60
NEKFKSRVTM TRDTSISTAY MELSRLRSDD TAVYYCARSW YGSSPYYFDY WGQGTLVTVS   120
S                                                                  121
```

```
SEQ ID NO: 144          moltype = AA  length = 107
FEATURE                 Location/Qualifiers
REGION                  1..107
                        note = Synthetic: LCVR; PD-L1
source                  1..107
                        mol_type = protein
                        organism = synthetic construct
SEQUENCE: 144
DIQMTQSPSS LSASVGDRVT ISCRASQDIS NYLNWYQQKP GKAPKLLIYY TSRLHSGVPS   60
RFSGSGSGTD FTFTISSLQP EDIATYFCQQ GNTLPWTFGQ GTKVEIK                107

SEQ ID NO: 145          moltype = AA  length = 121
FEATURE                 Location/Qualifiers
REGION                  1..121
                        note = Synthetic: HCVR; PD-L1
source                  1..121
                        mol_type = protein
                        organism = synthetic construct
SEQUENCE: 145
QVQLVQSGAE VKKPGASVKV SCKASGYTFT SYWMHWVRQA PGQGLEWMGM IHPTGVSTDY   60
NEKFKSRVTM TRDTSTSTVY MELSSLRSED TAVYYCARSD YGSSPYYFDY WGQGTLVTVS  120
S                                                                 121

SEQ ID NO: 146          moltype = AA  length = 107
FEATURE                 Location/Qualifiers
REGION                  1..107
                        note = Synthetic: LCVR; PD-L1
source                  1..107
                        mol_type = protein
                        organism = synthetic construct
SEQUENCE: 146
DIQMTQSPSS LSASVGDRVT ISCRASQDIS NYLNWYQQKP GKAPKLLIKY TSRLHSGVPS   60
RFSGSGSGTD FTLTISSLQP EDFATYFCQQ GDTLPWTFGG GTKVEIK                107

SEQ ID NO: 147          moltype = AA  length = 120
FEATURE                 Location/Qualifiers
REGION                  1..120
                        note = Synthetic: HCVR; PD-L1
source                  1..120
                        mol_type = protein
                        organism = synthetic construct
SEQUENCE: 147
DVQLQESGPG LVKPSQSLSL TCTVTGYSIT SDYAWNWIRQ FPGNKLEWMG YISDSGSTSY   60
NPSLKSRISI TRDTSKNQFF LQLNSVTTED TATYYCANSF LRLRSYFDHW GQGTTLTVSS  120

SEQ ID NO: 148          moltype = AA  length = 107
FEATURE                 Location/Qualifiers
REGION                  1..107
                        note = Synthetic: LCVR; PD-L1
source                  1..107
                        mol_type = protein
                        organism = synthetic construct
SEQUENCE: 148
DIVMTQSHKF MSTSVGDRVS ITCKASQDVN VAVAWYQQKP GQSPKLLIFW ASTRHIGVPD   60
RFTGSGSGTD YTLTISSVQA EDLALYYCQQ HYSTPYTFGG GTKLEIK                107

SEQ ID NO: 149          moltype = AA  length = 119
FEATURE                 Location/Qualifiers
REGION                  1..119
                        note = Synthetic: HCVR; PD-L1
source                  1..119
                        mol_type = protein
                        organism = synthetic construct
SEQUENCE: 149
QVQLVQSGAE VKKPGASVKV SCKASGYTFT SYGINWVRQA PGQRLEWMGW CIYIGNDYTN   60
YNEKFKGRVT ITRDTSASTA YMELSSLRSE DTAVYYCARA YYGSRVDYWG QGTLVTVSS   119

SEQ ID NO: 150          moltype = AA  length = 106
FEATURE                 Location/Qualifiers
REGION                  1..106
                        note = Synthetic: LCVR; PD-L1
source                  1..106
                        mol_type = protein
                        organism = synthetic construct
SEQUENCE: 150
DIQMTQSPSS LSAFVGDRVT ITCKASQDIN KYIAWYQQKP GKAPKLLIHY TSTLQPGVPS   60
RFSGSGSGRD FTFTISSLQP EDIATYYCLQ YDNLYTFGGG TKVEIK                 106

SEQ ID NO: 151          moltype = AA  length = 119
```

```
FEATURE                     Location/Qualifiers
REGION                      1..119
                            note = Synthetic: HCVR; PD-L1
source                      1..119
                            mol_type = protein
                            organism = synthetic construct
SEQUENCE: 151
QVQLVQSGAE VKKPGASVKV SCKASGYTFT SYGINWVRQA PGQRLEWMGW CIYIGNDYTN   60
YNEKFKGRVT ITRDTSASTA YMELSSLRSE DTAVYYCARA YYGSRVDYWG QGTLVTVSS   119

SEQ ID NO: 152              moltype = AA  length = 104
FEATURE                     Location/Qualifiers
REGION                      1..104
                            note = Synthetic: LCVR; PD-L1
source                      1..104
                            mol_type = protein
                            organism = synthetic construct
SEQUENCE: 152
EIVLTQSPVT LSLSPGERAT LSCQSISDYL HWYLQKPGQA PRLLIKCASQ SISGIPARFS   60
GSGSGSDFTL TISSLEPEDF AVYYCQNGHS FPYTFGGGTK VEIK                   104

SEQ ID NO: 153              moltype = AA  length = 121
FEATURE                     Location/Qualifiers
REGION                      1..121
                            note = Synthetic: HCVR; PD-L1
source                      1..121
                            mol_type = protein
                            organism = synthetic construct
SEQUENCE: 153
QVQLVQSGAE VKKPGASVKV SCKASGYTFT SYWMHWVRQA PGQGLEWMGM IHPNSGGNNY   60
NEKFKSRVTM TRDTSISTAY MELSRLRSDD TAVYYCARSW YGSSPYYFDY WGQGTLVTVS  120
S                                                                 121

SEQ ID NO: 154              moltype = AA  length = 107
FEATURE                     Location/Qualifiers
REGION                      1..107
                            note = Synthetic: LCVR; PD-L1
source                      1..107
                            mol_type = protein
                            organism = synthetic construct
SEQUENCE: 154
DIQMTQSPSS LSASVGDRVT ISCRASQDID NYLNWYQQKP GKAPKLLIKY TSRLHSGVPS   60
RFSGSGSGTD FTLTISSLQP EDFATYFCQQ GYTLPWTFGG GTKVEIK                107

SEQ ID NO: 155              moltype = AA  length = 246
FEATURE                     Location/Qualifiers
REGION                      1..246
                            note = Synthetic: VH; TP-M2T8P5
source                      1..246
                            mol_type = protein
                            organism = synthetic construct
SEQUENCE: 155
QVQLVQSGSE LKKPGASVKV SCKASGYTFT NYGMNWVRQA PGQGLEWMGW INTYTGEPTY   60
ADDFKGRFVF SLDTSVSTAY LQISSLKAED TAVYYCARAP PYGYDVRFAY WGQGTLVTVS  120
SGGGGSQVQL VQSGAEVKKP GASVKVSCKA SGYTFTTYYI YWVRQAPGQG LEWMGGINPG  180
NGGTNFNEKF KIRVTMTRDT SISTAYMELS SLRSEDTAVY YCARRYHGYD GGLDYWGQGT  240
LVTVSS                                                            246

SEQ ID NO: 156              moltype = AA  length = 238
FEATURE                     Location/Qualifiers
REGION                      1..238
                            note = Synthetic: VL; TP-M2T8P5
source                      1..238
                            mol_type = protein
                            organism = synthetic construct
SEQUENCE: 156
DVVMTQSPLS LPVTLGQPAS ISCRSSQSIV HSNGNTYLEW FQQRPGQSPR VLIYKVSDRF   60
SGVPDRFSGS GSGTDFTLKI SRVEAEDVGV YYCFQGSHVP WTFGRGTKLE IKGGGGSGGG  120
GSGGGGSDIV LTQSPASLAV SPGQRATITC RASKSVSTSG FSYIHWYQQK PGQPPKLLIY  180
LASNLESGVP ARFSGSGSGT DFTLTINPVE ANDTANYYCQ HTWELPNTFG GGTKVEIK    238

SEQ ID NO: 157              moltype = AA  length = 245
FEATURE                     Location/Qualifiers
REGION                      1..245
                            note = Synthetic: VL2/VH1; TP-M4T8P5
source                      1..245
                            mol_type = protein
                            organism = synthetic construct
SEQUENCE: 157
```

```
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IKRTVAAPSV   120
FIFPPPQVQLV QSGAEVKKPG ASVKVSCKAS GYTFTTYYIY WVRQAPGQGL EWMGGINPGN  180
GGTNFNEKFK IRVTMTRDTS ISTAYMELSS LRSEDTAVYY CARRYHGYDG GLDYWGQGTL   240
VTVSS                                                              245

SEQ ID NO: 158         moltype = AA   length = 245
FEATURE                Location/Qualifiers
REGION                 1..245
                       note = Synthetic: VH2/VL1; TP-M4T8P5
source                 1..245
                       mol_type = protein
                       organism = synthetic construct
SEQUENCE: 158
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPDIVLTQ SPASLAVSPG QRATITCRAS KSVSTSGFSY IHWYQQKPGQ   180
PPKLLIYLAS NLESGVPARF SGSGSGTDFT LTINPVEAND TANYYCQHTW ELPNTFGGGT   240
KVEIK                                                              245

SEQ ID NO: 159         moltype = AA   length = 679
FEATURE                Location/Qualifiers
REGION                 1..679
                       note = Synthetic: VH; TP-M6T8P5
source                 1..679
                       mol_type = protein
                       organism = synthetic construct
SEQUENCE: 159
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGGGG SGGGGSGGGG SDIVLTQSPA SLAVSPGQRA   480
TITCRASKSV STSGFSYIHW YQQKPGQPPK LLIYLASNLE SGVPARFSGS GSGTDFTLTI   540
NPVEANDTAN YYCQHTWELP NTFGGGTKVE IKRTVAAPSV FIFPPSDEQL KSGTASVVCL   600
LNNFYPREAK VQWKVDNALQ SGNSQESVTE QDSKDSTYSL SSTLTLSKAD YEKHKVYACE   660
VTHQGLSSPV TKSFNRGEC                                               679

SEQ ID NO: 160         moltype = AA   length = 219
FEATURE                Location/Qualifiers
REGION                 1..219
                       note = Synthetic: VL2/CL; TP-M6T8P5
source                 1..219
                       mol_type = protein
                       organism = synthetic construct
SEQUENCE: 160
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 161         moltype = AA   length = 237
FEATURE                Location/Qualifiers
REGION                 1..237
                       note = Synthetic: VH1/CH1; TP-M6T8P5
source                 1..237
                       mol_type = protein
                       organism = synthetic construct
SEQUENCE: 161
QVQLVQSGAE VKKPGASVKV SCKASGYTFT TYYIYWVRQA PGQGLEWMGG INPGNGGTNF    60
NEKFKIRVTM TRDTSISTAY MELSSLRSED TAVYYCARRY HGYDGGLDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGG      237

SEQ ID NO: 162         moltype = AA   length = 675
FEATURE                Location/Qualifiers
REGION                 1..675
                       note = Synthetic: VH; TP-M6T8L8
source                 1..675
                       mol_type = protein
                       organism = synthetic construct
SEQUENCE: 162
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
```

```
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGGGG SGGGGSGGGG SDIQMTQSPS SLSASVGDRV   480
TISCRASQDI DNYLNWYQQK PGKAPKLLIK YTSRLHSGVP SRFSGSGSGT DFTLTISSLQ   540
PEDFATYFCQ QGYTLPWTFG GGTKVEIKRT VAAPSVFIFP PSDEQLKSGT ASVVCLLNNF   600
YPREAKVQWK VDNALQSGNS QESVTEQDSK DSTYSLSSTL TLSKADYEKH KVYACEVTHQ   660
GLSSPVTKSF NRGEC                                                   675

SEQ ID NO: 163          moltype = AA   length = 219
FEATURE                 Location/Qualifiers
REGION                  1..219
                        note = Synthetic: VL2/CL; TP-M6T8L8
source                  1..219
                        mol_type = protein
                        organism = synthetic construct
SEQUENCE: 163
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 164          moltype = AA   length = 238
FEATURE                 Location/Qualifiers
REGION                  1..238
                        note = Synthetic: VH1/CH1; TP-M6T8L8
source                  1..238
                        mol_type = protein
                        organism = synthetic construct
SEQUENCE: 164
QVQLVQSGAE VKKPGASVKV SCKASGYTFT SYWMHWVRQA PGQGLEWMGM IHPNSGGNNY    60
NEKFKSRVTM TRDTSISTAY MELSRLRSDD TAVYYCARSW YGSSPYYFDY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGG     238

SEQ ID NO: 165          moltype = AA   length = 122
FEATURE                 Location/Qualifiers
REGION                  1..122
                        note = Synthetic: VH; TP-M8T10P1 (TP-83)
source                  1..122
                        mol_type = protein
                        organism = synthetic construct
SEQUENCE: 165
QVQLVQSGAE VKKPGASVKV SCKASGYTFT SYYMHWVRQA PGQGLEWMGI INPSGGRTSY    60
AQMFQGRVTM TRDTSTSTVY MELSSLRSED TAVYYCARDR EEQWPVGGFD YWGQGTLVTV   120
SS                                                                 122

SEQ ID NO: 166          moltype = AA   length = 463
FEATURE                 Location/Qualifiers
REGION                  1..463
                        note = Synthetic: LC; TP-M8T10P1 (TP-83)
source                  1..463
                        mol_type = protein
                        organism = synthetic construct
SEQUENCE: 166
DIQMTQSPSS LSASVGDRVT ITCRASQSIR RYLNWYQQKP GKAPKLLIYS ASNLQSGVPS    60
RFSGSGSGTD FTLTISSLQP EDFATYYCQQ SYIIPPTFGQ GTKVEIRRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSEVQLVE SGGGLVQPGG   240
SLRLSCAASG FTFSNFLMSW VRQAPGKGLE WVSTISGGGR DTYYVDSVKG RFTISRDNSK   300
NTLYLQMNSL RAEDTAVYYC AKRTTYSMDY WGQGTSVTVS SGGGGSGGGG SGGGGSDIQM   360
TQSPSSVSAS VGDRVTITCL ASQTIGTWLA WYQQKPGKAP KLLIDAATSL ADGVPSRFSG   420
SGSGTDFTLT ISSLQPEDFA TYYCQQFYSI PWTFGGGTKL EIK                    463

SEQ ID NO: 167          moltype = AA   length = 698
FEATURE                 Location/Qualifiers
REGION                  1..698
                        note = Synthetic: HC; TP-M9T10P1 (TP-93)
source                  1..698
                        mol_type = protein
                        organism = synthetic construct
SEQUENCE: 167
EVQLVESGGG LVQPGGSLRL SCAASGFTFS NFLMSWVRQA PGKGLEWVST ISGGGRDTYY    60
VDSVKGRFTI SRDNSKNTLY LQMNSLRAED TAVYYCAKRT TYSMDYWGQG TSVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
```

```
SCSVMHEALH NHYTQKSLSL SLGKGGGGSG GGGSQVQLVQ SGAEVKKPGA SVKVSCKASG    480
YTFTSYYMHW VRQAPGQGLE WMGIINPSGG RTSYAQMFQG RVTMTRDTST STVYMELSSL    540
RSEDTAVYYC ARDREEQWPV GGFDYWGQGT LVTVSSGGGG SGGGGSGGGG SDIQMTQSPS    600
SLSASVGDRV TITCRASQSI RRYLNWYQQK PGKAPKLLIY SASNLQSGVP SRFSGSGSGT    660
DFTLTISSLQ PEDFATYYCQ QSYIIPPTFG QGTKVEIK                           698

SEQ ID NO: 168           moltype = AA  length = 214
FEATURE                  Location/Qualifiers
REGION                   1..214
                         note = Synthetic: LC; TP-M9T10P1 (TP-93)
source                   1..214
                         mol_type = protein
                         organism = synthetic construct
SEQUENCE: 168
DIQMTQSPSS VSASVGDRVT ITCLASQTIG TWLAWYQQKP GKAPKLLIDA ATSLADGVPS    60
RFSGSGSGTD FTLTISSLQP EDFATYYCQQ FYSIPWTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 169           moltype = AA  length = 699
FEATURE                  Location/Qualifiers
REGION                   1..699
                         note = Synthetic: HC; TP-M9T10P5
source                   1..699
                         mol_type = protein
                         organism = synthetic construct
SEQUENCE: 169
QVQLVQSGAE VKKPGASVKV SCKASGYTFT TYYIYWVRQA PGQGLEWMGG INPGNGGTNF    60
NEKFKIRVTM TRDTSISTAY MELSSLRSED TAVYYCARRY HGYDGGLDYW GQGTLVTVSS    120
ASTKGPSVFP LAPCSRSTSE STAALGCLVK DYFPEPVTVS WNSGALTSGV HTFPAVLQSS    180
GLYSLSSVVT VPSSSLGTKT YTCNVDHKPS NTKVDKRVES KYGPPCPPCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLGGGGS GGGGSQVQLV QSGAEVKPG ASVKVSCKAS    480
GYTFTSYYMH WVRQAPGQGL EWMGIINPSG GRTSYAQMFQ GRVTMTRDTS TSTVYMELSS    540
LRSEDTAVYY CARDREEQWP VGGFDYWGQG TLVTVSSGGG GSGGGGSGGG GSDIQMTQSP    600
SSLSASVGDR VTITCRASQS IRRYLNWYQQ KPGKAPKLLI YSASNLQSGV PSRFSGSGSG    660
TDFTLTISSL QPEDFATYYC QQSYIIPPTF GQGTKVEIK                          699

SEQ ID NO: 170           moltype = AA  length = 111
FEATURE                  Location/Qualifiers
REGION                   1..111
                         note = Synthetic: LC; TP-M9T10P5
source                   1..111
                         mol_type = protein
                         organism = synthetic construct
SEQUENCE: 170
DIVLTQSPAS LAVSPGQRAT ITCRASKSVS TSGFSYIHWY QQKPGQPPKL LIYLASNLES    60
GVPARFSGSG SGTDFTLTIN PVEANDTANY YCQHTWELPN TFGGGTKVEI K             111

SEQ ID NO: 171           moltype = AA  length = 704
FEATURE                  Location/Qualifiers
REGION                   1..704
                         note = Synthetic: HC; TP-M10T8P5 (TP-92)
source                   1..704
                         mol_type = protein
                         organism = synthetic construct
SEQUENCE: 171
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFLGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLGKGG GGSGGGGSQV QLVQSGAEVK KPGASVKVSC    480
KASGYTFTTY YIYWVRQAPG QGLEWMGGIN PGNGGTNFNE KFKIRVTMTR DTSISTAYME    540
LSSLRSEDTA VYYCARRYHG YDGGLDYWGQ GTLVTVSSGG GGSGGGGSGG GGSDIVLTQS    600
PASLAVSPGQ RATITCRASK SVSTSGFSYI HWYQQKPGQP PKLLIYLASN LESGVPARFS    660
GSGSGTDFTL TINPVEANDT ANYYCQHTWE LPNTFGGGTK VEIK                    704

SEQ ID NO: 172           moltype = AA  length = 112
FEATURE                  Location/Qualifiers
REGION                   1..112
                         note = Synthetic: VL; TP-M10T8P5 (TP-92)
source                   1..112
                         mol_type = protein
                         organism = synthetic construct
```

```
SEQUENCE: 172
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IK           112

SEQ ID NO: 173          moltype = AA  length = 701
FEATURE                 Location/Qualifiers
REGION                  1..701
                        note = Synthetic: TP-M10T8L8
source                  1..701
                        mol_type = protein
                        organism = synthetic construct
SEQUENCE: 173
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGKGG GGSGGGGSQV QLVQSGAEVK KPGASVKVSC   480
KASGYTFTSY WMHWVRQAPG QGLEWMGMIH PNSGGNNYNE KFKSRVTMTR DTSISTAYME   540
LSRLRSDDTA VYYCARSWYG SSPYYFDYWG QGTLVTVSSG GGGSGGGGSG GGGSDIQMTQ   600
SPSSLSASVG DRVTISCRAS QDIDNYLNWY QQKPGKAPKL LIKYTSRLHS GVPSRFSGSG   660
SGTDFTLTIS SLQPEDFATY FCQQGYTLPW TFGGGTKVEI K                      701

SEQ ID NO: 174          moltype = AA  length = 448
FEATURE                 Location/Qualifiers
REGION                  1..448
                        note = Synthetic: VH2/CH1; TP-M14T8P5
source                  1..448
                        mol_type = protein
                        organism = synthetic construct
SEQUENCE: 174
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLK SDGSFFLYSR LTVDKSRWQE   420
GNVFSCSVMH EALHNHYTQK SLSLSLGK                                      448

SEQ ID NO: 175          moltype = AA  length = 438
FEATURE                 Location/Qualifiers
REGION                  1..438
                        note = Synthetic: VL1/CH1; TP-M14T8P5
source                  1..438
                        mol_type = protein
                        organism = synthetic construct
SEQUENCE: 175
DIVLTQSPAS LAVSPGQRAT ITCRASKSVS TSGFSYIHWY QQKPGQPPKL LIYLASNLES    60
GVPARFSGSG SGTDFTLTIN PVEANDTANY YCQHTWELPN TFGGGTKVEI KASTKGPSVF   120
PLAPCSRSTS ESTAALGCLV KDYFPEPVTV SWNSGALTSG VHTFPAVLQS SGLYSLSSVV   180
TVPSSSLGTK TYTCNVDHKP SNTKVDKRVE SKYGPPCPPC PAPEFLGGPS VFLFPPKPKD   240
TLMISRTPEV TCVVVDVSQE DPEVQFNWYV DGVEVHNAKT KPREEQFNST YRVVSVLTVL   300
HQDWLNGKEY KCKVSNKGLP SSIEKTISKA KGQPREPQVY TLPPSQEEMT KNQVSLTCLV   360
EGFYPSDIAV EWESNGQPEN NYATTPPVLD SDGSFFLYSD LTVDKSRWQE GNVFSCSVMH   420
EALHNHYTQK SLSLSLGK                                                 438

SEQ ID NO: 176          moltype = AA  length = 219
FEATURE                 Location/Qualifiers
REGION                  1..219
                        note = Synthetic: VL2/CL; TP-M14T8P5
source                  1..219
                        mol_type = protein
                        organism = synthetic construct
SEQUENCE: 176
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 177          moltype = AA  length = 232
FEATURE                 Location/Qualifiers
REGION                  1..232
                        note = Synthetic: VH1/CL; TP-M14T8P5
source                  1..232
                        mol_type = protein
                        organism = synthetic construct
```

```
SEQUENCE: 177
QVQLVQSGAE VKKPGASVKV SCKASGYTFT TYYIYWVRQA PGQGLEWMGG INPGNGGTNF     60
NEKFKIRVTM TRDTSISTAY MELSSLRSED TAVYYCARRY HGYDGGLDYW GQGTLVTVSS    120
GGGGSRTVAA PSVFIFPPSD EQLKSGTASV VCLLNNFYPR EAKVQWKVDN ALQSGNSQES   180
VTEQDSKDST YSLSSTLTLS KADYEKHKVY ACEVTHQGLS SPVTKSFNRG EC           232

SEQ ID NO: 178          moltype = AA   length = 448
FEATURE                 Location/Qualifiers
REGION                  1..448
                        note = Synthetic: VH2/HC1; TP-M14T8L8
source                  1..448
                        mol_type = protein
                        organism = synthetic construct
SEQUENCE: 178
QVQLVQSGSE LKKPGASVKV SCKASGYTFT NYGMNWVRQA PGQGLEWMGW INTYTGEPTY    60
ADDFKGRFVF SLDTSVSTAY LQISSLKAED TAVYYCARAP PYGYDVRFAY WGQGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEKMT   360
KNQVSLTCLV KGFYPSDIAV EWESNGQPEN NYKTTPPVLK SDGSFFLYSR LTVDKSRWQE   420
GNVFSCSVMH EALHNHYTQK SLSLSLGK                                      448

SEQ ID NO: 179          moltype = AA   length = 434
FEATURE                 Location/Qualifiers
REGION                  1..434
                        note = Synthetic: VL1/HC2; TP-M14T8L8
source                  1..434
                        mol_type = protein
                        organism = synthetic construct
SEQUENCE: 179
DIQMTQSPSS LSASVGDRVT ISCRASQDID NYLNWYQQKP GKAPKLLIKY TSRLHSGVPS    60
RFSGSGSGTD FTLTISSLQP EDFATYFCQQ GYTLPWTFGG GTKVEIKAST KGPSVFPLAP   120
CSRSTSESTA ALGCLVKDYF PEPVTVSWNS GALTSGVHTF PAVLQSSGLY SLSSVVTVPS   180
SSLGTKTYTC NVDHKPSNTK VDKRVESKYG PPCPPCPAPE FLGGPSVFLF PPKPKDTLMI   240
SRTPEVTCVV VDVSQEDPEV QFNWYVDGVE VHNAKTKPRE EQFNSTYRVV SVLTVLHQDW   300
LNGKEYKCKV SNKGLPSSIE KTISKAKGQP REPQVYTLPP SQEEMTKNQV SLTCLVEGFY   360
PSDIAVEWES NGQPENNYAT TPPVLDSDGS FFLYSDLTVD KSRWQEGNVF SCSVMHEALH   420
NHYTQKSLSL SLGK                                                     434

SEQ ID NO: 180          moltype = AA   length = 219
FEATURE                 Location/Qualifiers
REGION                  1..219
                        note = Synthetic: VL2/CL; TP-M14T8L8
source                  1..219
                        mol_type = protein
                        organism = synthetic construct
SEQUENCE: 180
DVVMTQSPLS LPVTLGQPAS ISCRSSQSIV HSNGNTYLEW FQQRPGQSPR VLIYKVSDRF    60
SGVPDRFSGS GSGTDFTLKI SRVEAEDVGV YYCFQGSHVP WTFGRGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 181          moltype = AA   length = 233
FEATURE                 Location/Qualifiers
REGION                  1..233
                        note = Synthetic: VH1/CL; TP-M14T8L8
source                  1..233
                        mol_type = protein
                        organism = synthetic construct
SEQUENCE: 181
QVQLVQSGAE VKKPGASVKV SCKASGYTFT SYWMHWVRQA PGQGLEWMGM IHPNSGGNNY    60
NEKFKSRVTM TRDTSISTAY MELSRLRSDD TAVYYCARSW YGSSPYYFDY WGQGTLVTVS   120
SGGGGSRTVA APSVFIFPPS DEQLKSGTAS VVCLLNNFYP REAKVQWKVD NALQSGNSQE   180
SVTEQDSKDS TYSLSSTLTL SKADYEKHKV YACEVTHQGL SSPVTKSFNR GEC          233

SEQ ID NO: 182          moltype = AA   length = 222
FEATURE                 Location/Qualifiers
REGION                  1..222
                        note = Synthetic: TIGIT
source                  1..222
                        mol_type = protein
                        organism = synthetic construct
SEQUENCE: 182
MTGTIETTGN ISAEKGGSII LQCHLSSTTA QVTQVNWEQQ DQLLAICNAD LGWHISPSFK    60
DRVAPGPGLG LTLQSLTVND TGEYFCIYHT YPDGTYTGRI FLEVLESSVA EHGARFQIPL   120
LGAMAATLVV ICTAVIVVVA LTRKKKALRI HSVEGDLRRK SAGQEEWSPS APSPPGSCVQ   180
AEAAPAGLCG EQRGEDCAEL HDYFNVLSYR SLGNCSFFTE TG                      222
```

```
SEQ ID NO: 183                  moltype = AA  length = 264
FEATURE                         Location/Qualifiers
REGION                          1..264
                                note = Synthetic: PD-1
source                          1..264
                                mol_type = protein
                                organism = synthetic construct
SEQUENCE: 183
LDSPDRPWNP PTFSPALLVV TEGDNATFTC SFSNTSESFV LNWYRMSPSN QTDKLAAFPE    60
DRSQPGQDCR FRVTQLPNGR DFHMSVVRAR RNDSGTYLCG AISLAPKAQI KESLRAELRV   120
TERRAEVPTA HPSPSPRPAG QFQTLVVGVV GGLLGSLVLL VWWLAVICSR AARGTIGARR   180
TGQPLKEDPS AVPVFSVDYG ELDFQWREKT PEPPVPCVPE QTEYATIVFP SGMGTSSPAR   240
RGSADGPRSA QPLRPEDGHC SWPL                                         264

SEQ ID NO: 184                  moltype = AA  length = 220
FEATURE                         Location/Qualifiers
REGION                          1..220
                                note = Synthetic: PD-L1
source                          1..220
                                mol_type = protein
                                organism = synthetic construct
SEQUENCE: 184
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SEHELTCQAE GYPKAEVIWT SSDHQVLSGK TTTTNSKREE KLFNVTSTLR   180
INTTTNEIFY CTFRRLDPEE NHTAELVIPE LPLAHPPNER                         220

SEQ ID NO: 185                  moltype = AA  length = 54
FEATURE                         Location/Qualifiers
REGION                          1..54
                                note = Synthetic: Tie2R-inhibitory peptide
source                          1..54
                                mol_type = protein
                                organism = synthetic construct
SEQUENCE: 185
AQQEECEWDP WTCEHMGSGS ATGGSGSTAS SGSGSATHQE ECEWDPWTCE HMLE          54

SEQ ID NO: 186                  moltype = AA  length = 286
FEATURE                         Location/Qualifiers
REGION                          1..286
                                note = Synthetic: Tie2R-inhibitory peptide-FcR fusion
source                          1..286
                                mol_type = protein
                                organism = synthetic construct
SEQUENCE: 186
DKTHTCPPCP APELLGGPSV FLFPPKPKDT LMISRTPEVT CVVVDVSHED PEVKFNWYVD    60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPGKGGG GGAQQEECEW   240
DPWTCEHMGS GSATGGSGST ASSGSGSATH QEECEWDPWT CEHMLE                  286

SEQ ID NO: 187                  moltype = AA  length = 12
FEATURE                         Location/Qualifiers
REGION                          1..12
                                note = Synthetic: Ang-2 inhibitor
source                          1..12
                                mol_type = protein
                                organism = synthetic construct
SEQUENCE: 187
ETFLSTNKLE NQ                                                       12

SEQ ID NO: 188                  moltype = AA  length = 6
FEATURE                         Location/Qualifiers
REGION                          1..6
                                note = Synthetic
source                          1..6
                                mol_type = protein
                                organism = synthetic construct
SEQUENCE: 188
ASTKGP                                                              6

SEQ ID NO: 189                  moltype = AA  length = 5
FEATURE                         Location/Qualifiers
REGION                          1..5
                                note = Synthetic
source                          1..5
                                mol_type = protein
                                organism = synthetic construct
SEQUENCE: 189
```

```
GGGGS                                                                              5

SEQ ID NO: 190         moltype = AA  length = 13
FEATURE                Location/Qualifiers
REGION                 1..13
                       note = Synthetic
source                 1..13
                       mol_type = protein
                       organism = synthetic construct
SEQUENCE: 190
RTVAAPSVFI FPP                                                                    13

SEQ ID NO: 191         moltype = AA  length = 15
FEATURE                Location/Qualifiers
REGION                 1..15
                       note = Synthetic
source                 1..15
                       mol_type = protein
                       organism = synthetic construct
SEQUENCE: 191
GGGGSGGGGS GGGGS                                                                  15

SEQ ID NO: 192         moltype = AA  length = 10
FEATURE                Location/Qualifiers
REGION                 1..10
                       note = Synthetic
source                 1..10
                       mol_type = protein
                       organism = synthetic construct
SEQUENCE: 192
GGGGSGGGGS                                                                        10
```